United States Patent
Firminger et al.

(10) Patent No.: US 9,911,165 B2
(45) Date of Patent: Mar. 6, 2018

(54) COMPUTATIONAL SYSTEMS AND METHODS FOR HEALTH SERVICES PLANNING AND MATCHING

(75) Inventors: Shawn P. Firminger, Redmond, WA (US); Jason Garms, Redmond, WA (US); Roderick A. Hyde, Redmond, WA (US); Edward K. Y. Jung, Bellevue, WA (US); Chris Demetrios Karkanias, Sammamish, WA (US); Eric C. Leuthardt, St. Louis, MO (US); Royce A. Levien, Lexington, MA (US); Richard T. Lord, Tacoma, WA (US); Robert W. Lord, Seattle, WA (US); Mark A. Malamud, Seattle, WA (US); John D. Rinaldo, Jr., Bellevue, WA (US); Clarence T. Tegreene, Bellevue, WA (US); Kristin M. Tolle, Redmond, WA (US); Lowell L. Wood, Jr., Bellevue, WA (US)

(73) Assignee: GEARBOX, LLC, Bellevue, WA (US)

( * ) Notice: Subject to any disclaimer, the term of this patent is extended or adjusted under 35 U.S.C. 154(b) by 0 days.

(21) Appl. No.: 12/657,980

(22) Filed: Jan. 29, 2010

(65) Prior Publication Data
US 2010/0268108 A1    Oct. 21, 2010

Related U.S. Application Data

(63) Continuation-in-part of application No. 12/381,377, filed on Mar. 10, 2009, now abandoned, and a continuation-in-part of application No. 12/381,680, filed on Mar. 12, 2009, now abandoned, and a continuation-in-part of application No. 12/587,239, filed on Oct. 2, 2009, now abandoned, and a continuation-in-part of application No. 12/587,313, (Continued)

(51) Int. Cl.
*G06Q 50/22* (2012.01)
*G06F 19/00* (2018.01)
*G06Q 10/06* (2012.01)

(52) U.S. Cl.
CPC ............ *G06Q 50/22* (2013.01); *G06F 19/328* (2013.01); *G06F 19/3418* (2013.01); *G06F 19/3481* (2013.01); *G06Q 10/06* (2013.01); *G16H 40/20* (2018.01); *G16H 50/20* (2018.01); *G16H 50/70* (2018.01); *G16H 80/00* (2018.01)

(58) Field of Classification Search
CPC ...... G06Q 50/22; G06Q 50/24; G06T 7/0012; G06T 2207/30004; A61B 5/4064
USPC ........................................................ 705/2–3
See application file for complete search history.

(56) References Cited

U.S. PATENT DOCUMENTS 5,106,482 A    4/1992  Milstein et al.
5,716,382 A    2/1998  Snell
(Continued)

OTHER PUBLICATIONS

MediBid; "MediBid is the Marketplace for Medicine®"; printed on Apr. 25, 2011; pp. 1-2; located at http://www.medibid.com.
(Continued)

*Primary Examiner* — Joseph D Burgess

(57) ABSTRACT

Systems and methods are described relating to detecting an indication of at least one attribute of an individual; accepting sensor data about the individual; and presenting a set of health care options at least partially based on the detecting an indication of at least one attribute of the individual and the accepting sensor data about the individual.

29 Claims, 40 Drawing Sheets

Related U.S. Application Data filed on Oct. 5, 2009, and a continuation-in-part of application No. 12/589,124, filed on Oct. 16, 2009, now abandoned, and a continuation-in-part of application No. 12/589,171, filed on Oct. 19, 2009, now abandoned, and a continuation-in-part of application No. 12/589,639, filed on Oct. 26, 2009, now abandoned, and a continuation-in-part of application No. 12/589,728, filed on Oct. 27, 2009, now abandoned, and a continuation-in-part of application No. 12/590,104, filed on Nov. 2, 2009, now abandoned, and a continuation-in-part of application No. 12/590,163, filed on Nov. 3, 2009, now abandoned, and a continuation-in-part of application No. 12/590,250, filed on Nov. 4, 2009, now abandoned, and a continuation-in-part of application No. 12/590,335, filed on Nov. 5, 2009, now abandoned, and a continuation-in-part of application No. 12/592,439, filed on Nov. 24, 2009, now abandoned, and a continuation-in-part of application No. 12/592,541, filed on Nov. 25, 2009, now abandoned, and a continuation-in-part of application No. 12/592,768, filed on Dec. 2, 2009, now Pat. No. 8,095,384, and a continuation-in-part of application No. 12/592,859, filed on Dec. 3, 2009, now abandoned, and a continuation-in-part of application No. 12/655,474, filed on Dec. 30, 2009, now abandoned, and a continuation-in-part of application No. 12/655,580, filed on Dec. 31, 2009, now abandoned, and a continuation-in-part of application No. 12/657,429, filed on Jan. 20, 2010, and a continuation-in-part of application No. 12/657,498, filed on Jan. 21, 2010, now abandoned.

(56) References Cited

U.S. PATENT DOCUMENTS

| | | | |
|---|---|---|---|
| 5,718,247 | A | 2/1998 | Frankel |
| 5,738,104 | A | 4/1998 | Lo et al. |
| 5,911,132 | A | 6/1999 | Sloane |
| 5,926,794 | A | 7/1999 | Fethe |
| 6,014,654 | A | 1/2000 | Ariyoshi |
| 6,019,507 | A | 2/2000 | Takaki |
| 6,023,685 | A | 2/2000 | Brett et al. |
| 6,067,523 | A | 5/2000 | Bair et al. |
| 6,012,053 | A | 6/2000 | Pant et al. |
| 6,155,974 | A | 12/2000 | Fish |
| 6,231,187 | B1* | 5/2001 | Munoz .................. A61B 3/113 351/209 |
| 6,315,719 | B1 | 11/2001 | Rode et al. |
| 6,334,192 | B1 | 12/2001 | Karpf |
| 6,480,730 | B2 | 11/2002 | Darrow et al. |
| 6,584,445 | B2 | 6/2003 | Papageorge |
| 6,807,531 | B1* | 10/2004 | Kanai .................. G06F 19/3443 705/2 |
| 6,829,499 | B1 | 12/2004 | Shahinpoor et al. |
| 6,915,297 | B2 | 7/2005 | Chou |
| 7,079,977 | B2 | 7/2006 | Osorio et al. |
| 7,120,486 | B2 | 10/2006 | Leuthardt et al. |
| 7,194,301 | B2 | 3/2007 | Jenkins et al. |
| 7,283,856 | B2 | 10/2007 | Boling |
| 7,387,607 | B2 | 6/2008 | Holt et al. |
| 7,406,453 | B2 | 7/2008 | Mundie et al. |
| 7,424,409 | B2 | 9/2008 | Ben-Gal et al. |
| 7,519,540 | B2 | 4/2009 | Mayaud |
| 7,711,580 | B1 | 5/2010 | Hudson |
| 7,720,708 | B1 | 5/2010 | Elkins, II et al. |
| 7,901,368 | B2* | 3/2011 | Flaherty .................. A61H 1/0255 601/33 |
| 7,941,351 | B1 | 5/2011 | Rosenfeld et al. |
| 7,949,580 | B1 | 5/2011 | Boyer et al. |
| 2002/0059132 | A1 | 5/2002 | Quay et al. |
| 2002/0065758 | A1 | 5/2002 | Henley |
| 2002/0141629 | A1* | 10/2002 | Schreck ................... 382/131 |
| 2003/0046113 | A1* | 3/2003 | Johnson .................. G06Q 10/10 705/3 |
| 2003/0091964 | A1 | 5/2003 | Yeager |
| 2003/0101086 | A1 | 5/2003 | San Miguel |
| 2003/0130927 | A1 | 7/2003 | Kellam et al. |
| 2003/0191669 | A1 | 10/2003 | Fitzgerald et al. |
| 2003/0212673 | A1 | 11/2003 | Kadayam et al. |
| 2004/0015337 | A1 | 1/2004 | Thomas et al. |
| 2004/0193529 | A1 | 9/2004 | Asher et al. |
| 2005/0125289 | A1 | 6/2005 | Beyda et al. |
| 2005/0149364 | A1 | 7/2005 | Ombrellaro |
| 2005/0177051 | A1 | 8/2005 | Almen |
| 2006/0136264 | A1* | 6/2006 | Eaton .................. G06Q 30/0206 705/2 |
| 2006/0143043 | A1 | 6/2006 | McCallie, Jr. et al. |
| 2006/0230033 | A1 | 10/2006 | Halevy et al. |
| 2006/0290885 | A1 | 12/2006 | Covannon et al. |
| 2007/0027714 | A1 | 2/2007 | Fenno |
| 2007/0087901 | A1 | 4/2007 | Brassil et al. |
| 2007/0106143 | A1 | 5/2007 | Flaherty |
| 2007/0150024 | A1* | 6/2007 | Leyde .................. A61B 5/0476 607/45 |
| 2007/0156647 | A1 | 7/2007 | Shen et al. |
| 2007/0192300 | A1 | 8/2007 | Reuther et al. |
| 2007/0214008 | A1 | 9/2007 | Jung et al. |
| 2007/0250343 | A1 | 10/2007 | Sohal |
| 2007/0265507 | A1* | 11/2007 | de Lemos .............. A61B 3/113 600/300 |
| 2007/0271119 | A1 | 11/2007 | Boerger et al. |
| 2007/0288262 | A1 | 12/2007 | Sakaue et al. |
| 2008/0065468 | A1 | 3/2008 | Berg et al. |
| 2008/0091086 | A1 | 4/2008 | Legere et al. |
| 2008/0147582 | A1 | 6/2008 | Micaelian et al. |
| 2008/0154912 | A1 | 6/2008 | Weber et al. |
| 2008/0158579 | A1 | 7/2008 | Ohga et al. |
| 2008/0172214 | A1 | 7/2008 | Col et al. |
| 2008/0215570 | A1 | 9/2008 | Maloney et al. |
| 2008/0215627 | A1 | 9/2008 | Higgins et al. |
| 2008/0287746 | A1 | 11/2008 | Reisman |
| 2009/0006419 | A1 | 1/2009 | Savitsky et al. |
| 2009/0030334 | A1 | 1/2009 | Anderson et al. |
| 2009/0036757 | A1 | 2/2009 | Brockway et al. |
| 2009/0043801 | A1 | 2/2009 | LeClair et al. |
| 2009/0083070 | A1 | 3/2009 | Giftakis et al. |
| 2009/0089084 | A1 | 4/2009 | Schoenberg |
| 2009/0105557 | A1 | 4/2009 | Najafi et al. |
| 2009/0112623 | A1 | 4/2009 | Schoenberg |
| 2009/0149778 | A1* | 6/2009 | Naujokat .............. A61B 5/0002 600/595 |
| 2009/0182667 | A1 | 7/2009 | Parkes et al. |
| 2009/0192534 | A1 | 7/2009 | Ortiz et al. |
| 2009/0240527 | A1 | 9/2009 | Bluth |
| 2009/0281835 | A1 | 11/2009 | Patwardhan et al. |
| 2010/0063830 | A1 | 3/2010 | Kenedy et al. |
| 2010/0106518 | A1 | 4/2010 | Kuo |
| 2010/0113950 | A1 | 5/2010 | Lin et al. |
| 2010/0235295 | A1 | 9/2010 | Zides et al. |

OTHER PUBLICATIONS

Medicine Online; printed on Apr. 25, 2011; pp. 1-2; located at http://www.medicineonline.com Rustad, Mitch; "Bid-For-Surgery Web Site to Launch"; Medical Tribune; bearing a date of 1999; printed on Apr. 25, 2011; pp. 1-3; 40(21):3; located at http://www.mo1.net/media/medscape-trib-/Bid-For-Surgery_Web_Site_To_Launch.htm.

"Internet Archive Wayback Machine"; bearing a date of Feb. 20, 2008; created on Jul. 9, 2015; 1 pg.; located at www.zocdoc.com.

"Quantitative Aspects of Clinical Decision Making Part 2"; bearing a date of Jun. 10, 2006; printed on Jul. 10, 2015; pp. 1-10; located at: www.what-when-how.com.

"Quantitative Aspects of Clinical Decision Making Part 3"; bearing a date of Jun. 10, 2006; printed on Jul. 10, 2015; pp. 1-5; located at: www.what-when-how.com.

(56) References Cited

OTHER PUBLICATIONS

Adams, Damon; "Web sites let patients find like-minded physicians"; amednews.com; Mar. 27, 2006; pp. 1-3; American Medical Association.
"Find a Doctor" located at https://web.archive.org/web/20080913161147/http://www.aesnet.org/go/find-a-dr/epilepsy-com; 2007; bearing a date of Jan. 20, 2016; 1 page; epilepsy.com.
"Find an Epilepsy Center" located at https://web.archive.org/web/20081206075409/http://www.naeclocator.org/find.htm; 2007; bearing a date of Jan. 20, 2016; 1 page; NAEC.
"Welcome" located at https://web.archive.org/web/20080219060742/http://www.naeclocator.org/; 2007; bearing a date of Jan. 20, 2016; 1 page; NAEC.
"Insurers Roll Out Hospital Quality Data But Hospital Grades, Cost Info Is Optional", Managed Care Week, Mar. 24, 2003, vol. 13, No. 11, p. 1 (5 total pages).
U.S. Appl. No. 12/657,498, filed Jan. 21, 2009, Firminger et al.
U.S. Appl. No. 12/657,429, filed Jan. 20, 2010, Firminger et al.
U.S. Appl. No. 12/655,580, filed Dec. 31, 2009, Firminger et al.
U.S. Appl. No. 12/655,474, filed Dec. 30, 2009, Firminger et al.
U.S. Appl. No. 12/592,859, filed Dec. 3, 2009, Firminger et al.
U.S. Appl. No. 12/592,768, filed Dec. 2, 2009, Firminger et al.
U.S. Appl. No. 12/592,541, filed Nov. 25, 2009, Firminger et al.
U.S. Appl. No. 12/592,439, filed Nov. 24, 2009, Firminger et al.
U.S. Appl. No. 12/590,335, filed Nov. 5, 2009, Firminger et al.
U.S. Appl. No. 12/590,250, filed Nov. 4, 2009, Firminger et al.
U.S. Appl. No. 12/590,163, filed Nov. 3, 2009, Firminger et al.
U.S. Appl. No. 12/590,104, filed Nov. 2, 2009, Firminger et al.
U.S. Appl. No. 12/589,728, filed Oct. 27, 2009, Firminger et al.
U.S. Appl. No. 12/589,639, filed Oct. 26, 2009, Firminger et al.
U.S. Appl. No. 12/589,171, filed Oct. 19, 2009, Firminger et al.
U.S. Appl. No. 12/589,124, filed Oct. 16, 2009, Firminger et al.
U.S. Appl. No. 12/587,313, filed Oct. 5, 2009, Firminger et al.
U.S. Appl. No. 12/587,239, filed Oct. 2, 2009, Firminger et al.
U.S. Appl. No. 12/381,680, filed Mar. 12, 2009, Firminger et al.
U.S. Appl. No. 12/381,377, filed Mar. 10, 2009, Firminger et al.
Axelrod et al., "Smoke and Mirrors: Gathering User Requirements for Emerging Affective Systems," 26th Int. Conf. Information Technology Interfaces /TI 2004, Jun. 7-10, 2004, Cavtat, Croatia, pp. 323-328.
"Cancer in Scotland: Radiotherapy Activity Planning for Scotland 2011-2015," available at http://www.scotland.gov.uk/Publications/2006/01/24131719/28, (2006).
Clarke, "IMEC has a brain wave: feed EEG emotion back into games," EE Times online, http://www.eetimes.eu/design/202801063 (Nov. 1, 2007).
Cohn, J.N., Introduction to Surrogate Markers, Circulation 109: IV20-21, American Heart Association, (2004).
Frenkel et al., "An approach for integrating complementary-alternative medicine into primary care," Fam. Pract., 20(3), pp. 324-332 (2003).
Goodman, Clifford S., "Introduction to Health Care Technology Assessment," available at http://www.nlm.nih.gov/nichsr/hta101/ta101_c1.html, (Jan. 2004).
Martinez-Sema et al., "Symptom Priority Ranking in the Care of Gastroesophageal Reflux: A Review of 1,850 Cases," Dig Dis, 17:219-224 (1999).
Nikovski, D., "Constructing Bayesian Networks for Medical Diagnosis from Incomplete and Partially Correct Statistics," IEEE Transactions on Knowledge and Data Engineering, vol. 12:4, pp. 509-516 (2000).
Physorg.com, "New mini-sensor may have biomedical and security applications," Nov. 1, 2007, http://www.physorg.com/news113151078.html.
Sanfey, "Social Decision-Making: Insights from Game Theory and Neuroscience," Science, vol. 318, pp. 598-601 (Oct. 26, 2007).
Tarricone et al., "Economic evaluation of nimesulide versus diclofenac in the treatment of osteoarthritis in France, Italy and Spain," Clin. Drug Invest. 21(7) pp. 453-464 (2001).

* cited by examiner

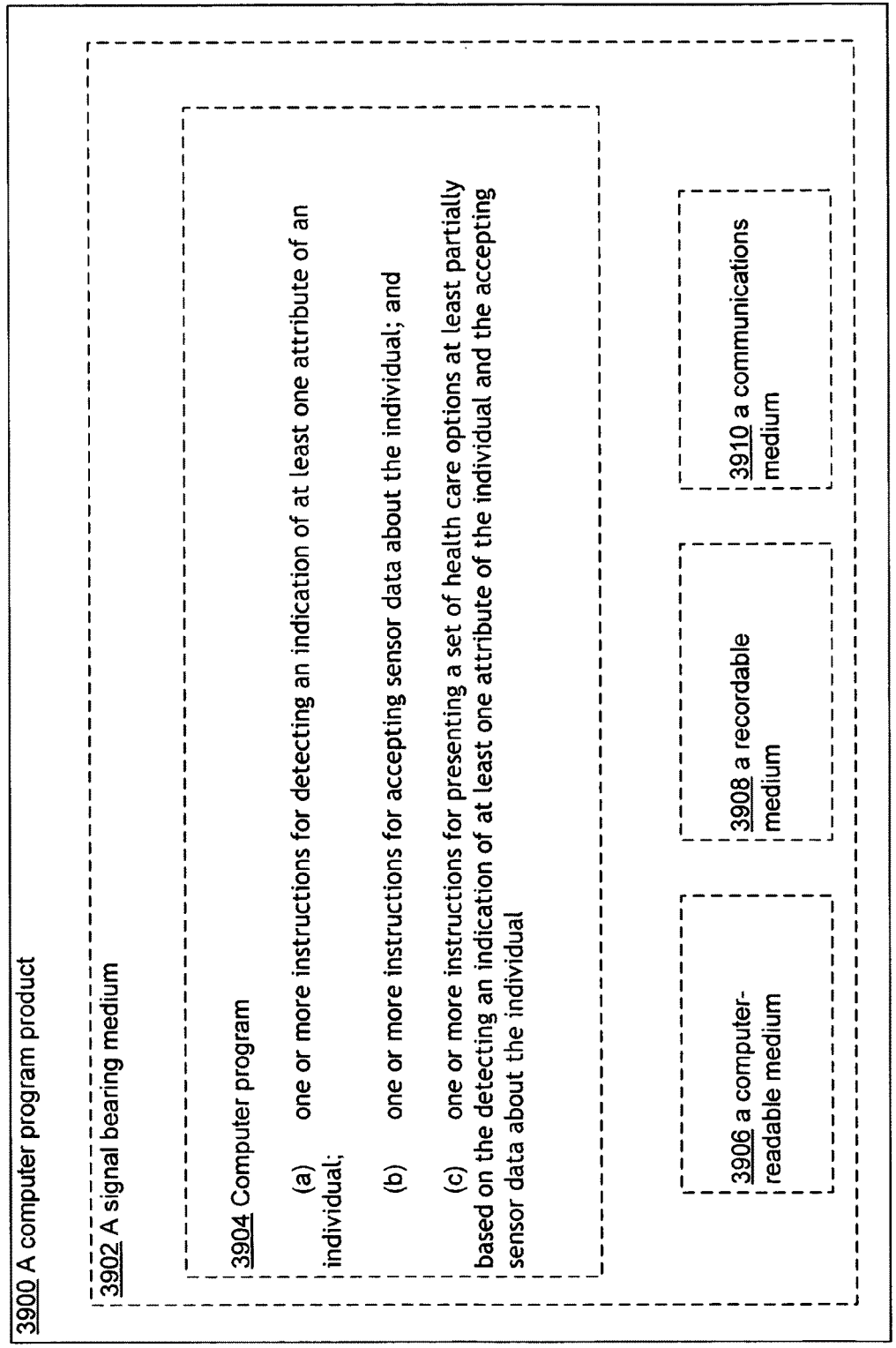

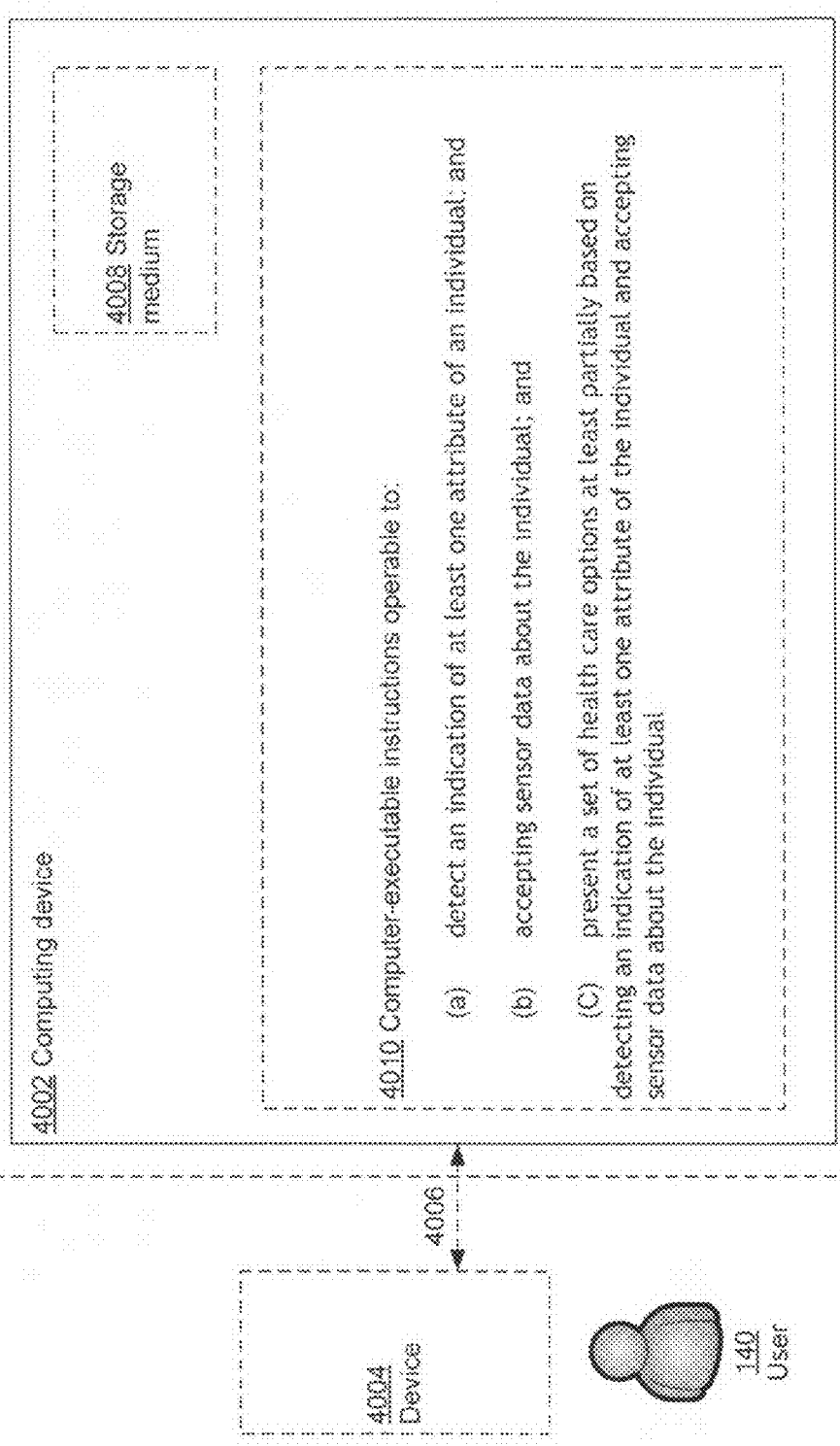

COMPUTATIONAL SYSTEMS AND METHODS FOR HEALTH SERVICES PLANNING AND MATCHING

CROSS-REFERENCE TO RELATED APPLICATIONS

The present application is related to and claims the benefit of the earliest available effective filing date(s) from the following listed application(s) (the "Related Applications") (e.g., claims earliest available priority dates for other than provisional patent applications or claims benefits under 35 USC § 119(e) for provisional patent applications, for any and all parent, grandparent, great-grandparent, etc. applications of the Related Application(s)).

RELATED APPLICATIONS

For purposes of the USPTO extra-statutory requirements, the present application constitutes a continuation-in-part of U.S. patent application Ser. No. 12/381,377, entitled COMPUTATIONAL SYSTEMS AND METHODS FOR HEALTH SERVICES PLANNING AND MATCHING, naming Shawn P. Firminger, Jason Garms, Roderick A. Hyde; Edward K. Y. Jung; Chris Demetrios Karkanias; Eric C. Leuthardt; Royce A. Levien; Richard T. Lord; Robert W. Lord; Mark A. Malamud; John D. Rinaldo, Jr.; Clarence T. Tegreene; Kristin M. Tolle; and Lowell L. Wood, Jr., as inventors, filed 10 Mar. 2009 which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/381,680, entitled COMPUTATIONAL SYSTEMS AND METHODS FOR HEALTH SERVICES PLANNING AND MATCHING, naming Shawn P. Firminger, Jason Garms, Roderick A. Hyde; Edward K. Y. Jung; Chris Demetrios Karkanias; Eric C. Leuthardt; Royce A. Levien; Richard T. Lord; Robert W. Lord; Mark A. Malamud; John D. Rinaldo, Jr.; Clarence T. Tegreene; Kristin M. Tolle; and Lowell L. Wood, Jr., as inventors, filed 12 Mar. 2009 which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/587,239, entitled COMPUTATIONAL SYSTEMS AND METHODS FOR HEALTH SERVICES PLANNING AND MATCHING, naming Shawn P. Firminger, Jason Garms, Roderick A. Hyde; Edward K. Y. Jung; Chris Demetrios Karkanias; Eric C. Leuthardt; Royce A. Levien; Richard T. Lord; Robert W. Lord; Mark A. Malamud; John D. Rinaldo, Jr.; Clarence T. Tegreene; Kristin M. Tolle; and Lowell L. Wood, Jr., as inventors, filed 2 Oct. 2009 which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/587,313, entitled COMPUTATIONAL SYSTEMS AND METHODS FOR HEALTH SERVICES PLANNING AND MATCHING, naming Shawn P. Firminger, Jason Garms, Roderick A. Hyde; Edward K. Y. Jung; Chris Demetrios Karkanias; Eric C. Leuthardt; Royce A. Levien; Richard T. Lord; Robert W. Lord; Mark A. Malamud; John D. Rinaldo, Jr.; Clarence T. Tegreene; Kristin M. Tolle; and Lowell L. Wood, Jr., as inventors, filed 5 Oct. 2009 which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/589,124, entitled COMPUTATIONAL SYSTEMS AND METHODS FOR HEALTH SERVICES PLANNING AND MATCHING, naming Shawn P. Firminger, Jason Garms, Roderick A. Hyde; Edward K. Y. Jung; Chris Demetrios Karkanias; Eric C. Leuthardt; Royce A. Levien; Richard T. Lord; Robert W. Lord; Mark A. Malamud; John D. Rinaldo, Jr.; Clarence T. Tegreene; Kristin M. Tolle; and Lowell L. Wood, Jr., as inventors, filed 16 Oct. 2009 now abandoned which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/589,171, entitled COMPUTATIONAL SYSTEMS AND METHODS FOR HEALTH SERVICES PLANNING AND MATCHING, naming Shawn P. Firminger, Jason Garms, Roderick A. Hyde; Edward K. Y. Jung; Chris Demetrios Karkanias; Eric C. Leuthardt; Royce A. Levien; Richard T. Lord; Robert W. Lord; Mark A. Malamud; John D. Rinaldo, Jr.; Clarence T. Tegreene; Kristin M. Tolle; and Lowell L. Wood, Jr., as inventors, filed 19 Oct. 2009 which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/589,639, entitled COMPUTATIONAL SYSTEMS AND METHODS FOR HEALTH SERVICES PLANNING AND MATCHING, naming Shawn P. Firminger, Jason Garms, Roderick A. Hyde; Edward K. Y. Jung; Chris Demetrios Karkanias; Eric C. Leuthardt; Royce A. Levien; Richard T. Lord; Robert W. Lord; Mark A. Malamud; John D. Rinaldo, Jr.; Clarence T. Tegreene; Kristin M. Tolle; and Lowell L. Wood, Jr., as inventors, filed 26 Oct. 2009 which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/589,728, entitled COMPUTATIONAL SYSTEMS AND METHODS FOR HEALTH SERVICES PLANNING AND MATCHING, naming Shawn P. Firminger, Jason Garms, Roderick A. Hyde; Edward K. Y. Jung; Chris Demetrios Karkanias; Eric C. Leuthardt; Royce A. Levien; Richard T. Lord; Robert W. Lord; Mark A. Malamud; John D. Rinaldo, Jr.; Clarence T. Tegreene; Kristin M. Tolle; and Lowell L. Wood, Jr., as inventors, filed 27 Oct. 2009 which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/590,104, entitled COMPUTATIONAL SYSTEMS AND METHODS FOR HEALTH SERVICES PLANNING AND MATCHING, naming Shawn P. Firminger, Jason Garms, Roderick A. Hyde; Edward K. Y. Jung; Chris Demetrios Karkanias; Eric C. Leuthardt; Royce A. Levien; Richard T. Lord; Robert W. Lord; Mark A. Malamud; John D. Rinaldo, Jr.; Clarence T. Tegreene; Kristin M. Tolle; and Lowell L. Wood, Jr., as inventors, filed 2 Nov. 2009 which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/590,163, entitled COMPUTATIONAL SYSTEMS AND METHODS FOR HEALTH SERVICES PLANNING AND MATCHING, naming Shawn P. Firminger, Jason Garms, Roderick A. Hyde; Edward K. Y. Jung; Chris Demetrios Karkanias; Eric C. Leuthardt; Royce A. Levien; Richard T. Lord; Robert W. Lord; Mark A. Malamud; John D. Rinaldo, Jr.; Clarence T. Tegreene; Kristin M. Tolle; and Lowell L. Wood, Jr., as inventors, filed 3 Nov. 2009 which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/590,250, entitled COMPUTATIONAL SYSTEMS AND METHODS FOR HEALTH SERVICES PLANNING AND MATCHING, naming Shawn P. Firminger, Jason Garms, Roderick A. Hyde; Edward K. Y. Jung; Chris Demetrios Karkanias; Eric C. Leuthardt; Royce A. Levien; Richard T. Lord; Robert W. Lord; Mark A. Malamud; John D. Rinaldo, Jr.; Clarence T. Tegreene; Kristin M. Tolle; and Lowell L. Wood, Jr., as inventors, filed 4 Nov. 2009 which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/590,335, entitled COMPUTATIONAL SYSTEMS AND METHODS FOR HEALTH SERVICES PLANNING AND MATCHING, naming Shawn P. Firminger, Jason Garms, Roderick A. Hyde; Edward K. Y. Jung; Chris Demetrios Karkanias; Eric C. Leuthardt; Royce A. Levien; Richard T. Lord; Robert W. Lord; Mark A. Malamud; John D. Rinaldo, Jr.; Clarence T. Tegreene; Kristin M. Tolle; and Lowell L. Wood, Jr., as inventors, filed 5 Nov. 2009 which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/592,439, entitled COMPUTATIONAL SYSTEMS AND METHODS FOR HEALTH SERVICES PLANNING AND MATCHING, naming Shawn P. Firminger, Jason Garms, Roderick A. Hyde; Edward K. Y. Jung; Chris Demetrios Karkanias; Eric C. Leuthardt; Royce A. Levien; Richard T. Lord; Robert W. Lord; Mark A. Malamud; John D. Rinaldo, Jr.; Clarence T. Tegreene; Kristin M. Tolle; and Lowell L. Wood, Jr., as inventors, filed 24 Nov. 2009 which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/592,541, entitled COMPUTATIONAL SYSTEMS AND METHODS FOR HEALTH SERVICES PLANNING AND MATCHING, naming Shawn P. Firminger, Jason Garms, Roderick A. Hyde; Edward K. Y. Jung; Chris Demetrios Karkanias; Eric C. Leuthardt; Royce A. Levien; Richard T. Lord; Robert W. Lord; Mark A. Malamud; John D. Rinaldo, Jr.; Clarence T. Tegreene; Kristin M. Tolle; and Lowell L. Wood, Jr., as inventors, filed 25 Nov. 2009 which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/592,768, entitled COMPUTATIONAL SYSTEMS AND METHODS FOR HEALTH SERVICES PLANNING AND MATCHING, naming Shawn P. Firminger, Jason Garms, Roderick A. Hyde; Edward K. Y. Jung; Chris Demetrios Karkanias; Eric C. Leuthardt; Royce A. Levien; Richard T. Lord; Robert W. Lord; Mark A. Malamud; John D. Rinaldo, Jr.; Clarence T. Tegreene; Kristin M. Tolle; and Lowell L. Wood, Jr., as inventors, filed 2 Dec. 2009 now U.S. Pat. No. 8,095,384 which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/592,859, entitled COMPUTATIONAL SYSTEMS AND METHODS FOR HEALTH SERVICES PLANNING AND MATCHING, naming Shawn P. Firminger, Jason Garms, Roderick A. Hyde; Edward K. Y. Jung; Chris Demetrios Karkanias; Eric C. Leuthardt; Royce A. Levien; Richard T. Lord; Robert W. Lord; Mark A. Malamud; John D. Rinaldo, Jr.; Clarence T. Tegreene; Kristin M. Tolle; and Lowell L. Wood, Jr., as inventors, filed 3 Dec. 2009 which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/655,474, entitled COMPUTATIONAL SYSTEMS AND METHODS FOR HEALTH SERVICES PLANNING AND MATCHING, naming Shawn P. Firminger, Jason Garms, Roderick A. Hyde; Edward K. Y. Jung; Chris Demetrios Karkanias; Eric C. Leuthardt; Royce A. Levien; Richard T. Lord; Robert W. Lord; Mark A. Malamud; John D. Rinaldo, Jr.; Clarence T. Tegreene; Kristin M. Tolle; and Lowell L. Wood, Jr., as inventors, filed 30 Dec. 2009 which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/655,580, entitled COMPUTATIONAL SYSTEMS AND METHODS FOR HEALTH SERVICES PLANNING AND MATCHING, naming Shawn P. Firminger, Jason Garms, Roderick A. Hyde; Edward K. Y. Jung; Chris Demetrios Karkanias; Eric C. Leuthardt; Royce A. Levien; Richard T. Lord; Robert W. Lord; Mark A. Malamud; John D. Rinaldo, Jr.; Clarence T. Tegreene; Kristin M. Tolle; and Lowell L. Wood, Jr., as inventors, filed 31 Dec. 2009 which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/657,429, entitled COMPUTATIONAL SYSTEMS AND METHODS FOR HEALTH SERVICES PLANNING AND MATCHING, naming Shawn P. Firminger, Jason Garms, Roderick A. Hyde; Edward K. Y. Jung; Chris Demetrios Karkanias; Eric C. Leuthardt; Royce A. Levien; Richard T. Lord; Robert W. Lord; Mark A. Malamud; John D. Rinaldo, Jr.; Clarence T. Tegreene; Kristin M. Tolle; and Lowell L. Wood, Jr., as inventors, filed 20 Jan. 2010 which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/657,498, entitled COMPUTATIONAL SYSTEMS AND METHODS FOR HEALTH SERVICES PLANNING AND MATCHING, naming Shawn P. Firminger, Jason Garms, Roderick A. Hyde; Edward K. Y. Jung; Chris Demetrios Karkanias; Eric C. Leuthardt; Royce A. Levien; Richard T. Lord; Robert W. Lord; Mark A. Malamud; John D. Rinaldo, Jr.; Clarence T. Tegreene; Kristin M. Tolle; and Lowell L. Wood, Jr., as inventors, filed 21 Jan. 2010 which is currently co-pending, or is an application of which a currently co-pending application is entitled to the benefit of the filing date.

The United States Patent Office (USPTO) has published a notice to the effect that the USPTO's computer programs require that patent applicants reference both a serial number and indicate whether an application is a continuation or continuation-in-part. Stephen G. Kunin, Benefit of Prior-Filed Application, USPTO Official Gazette Mar. 18, 2003, available at http://www.uspto.gov/web/offices/com/sol/og/2003/week11/patbene.htm. The present Applicant Entity (hereinafter "Applicant") has provided above a specific reference to the application(s) from which priority is being claimed as recited by statute. Applicant understands that the statute is unambiguous in its specific reference language and does not require either a serial number or any characterization, such as "continuation" or "continuation-in-part," for claiming priority to U.S. patent applications. Notwithstanding the foregoing, Applicant understands that the USPTO's computer programs have certain data entry requirements, and hence Applicant is designating the present application as a continuation-in-part of its parent applications as set forth above, but expressly points out that such designations are not to be construed in any way as any type of commentary and/or admission as to whether or not the present application contains any new matter in addition to the matter of its parent application(s).

All subject matter of the Related Applications and of any and all parent, grandparent, great-grandparent, etc. applications of the Related Applications is incorporated herein by reference to the extent such subject matter is not inconsistent herewith.

TECHNICAL FIELD

This description relates to data capture and data handling techniques.

SUMMARY

In one aspect, a method includes but is not limited to detecting an indication of at least one attribute of an individual, accepting sensor data about the individual, and presenting a set of health care options at least partially based on the detecting an indication of at least one attribute of the individual and the accepting sensor data about the individual. In addition to the foregoing, other apparatus aspects are described in the claims, drawings, and text forming a part of the present disclosure.

In one or more various aspects, related systems include but are not limited to circuitry and/or programming for effecting the herein referenced method aspects; the circuitry and/or programming can be virtually any combination of hardware, software, and/or firmware configured to effect the herein referenced method aspects depending upon the design choices of the system designer.

In one aspect, a system includes but is not limited to means for detecting an indication of at least one attribute of an individual, means for accepting sensor data about the individual, and means for presenting a set of health care options at least partially based on the detecting an indication of at least one attribute of the individual and the accepting sensor data about the individual. In addition to the foregoing, other apparatus aspects are described in the claims, drawings, and text forming a part of the present disclosure.

In one aspect, a system includes but is not limited to circuitry for detecting an indication of at least one attribute of an individual, circuitry for accepting sensor data about the individual, and circuitry for presenting a set of health care options at least partially based on the detecting an indication of at least one attribute of the individual and the accepting sensor data about the individual. In addition to the foregoing, other apparatus aspects are described in the claims, drawings, and text forming a part of the present disclosure.

In one aspect, a computer program product includes but is not limited to a signal-bearing medium bearing one or more instructions for detecting an indication of at least one attribute of an individual, one or more instructions for accepting sensor data about the individual, and one or more instructions for presenting a set of health care options at least partially based on the detecting an indication of at least one attribute of the individual and the accepting sensor data about the individual. In addition to the foregoing, other method aspects are described in the claims, drawings, and text forming a part of the present disclosure.

In one aspect, a system includes but is not limited to a computing device and instructions that when executed on the computing device cause the computing device to detect an indication of at least one attribute of an individual, accept sensor data about the individual, and present a set of health care options at least partially based on the accepting an indication of at least one attribute of the individual and the accepting sensor data about the individual. In addition to the foregoing, other method aspects are described in the claims, drawings, and text forming a part of the present disclosure.

The foregoing is a summary and thus may contain simplifications, generalizations, inclusions, and/or omissions of detail; consequently, those skilled in the art will appreciate that the summary is illustrative only and is NOT intended to be in any way limiting. Other aspects, features, and advantages of the devices and/or processes and/or other subject matter described herein will become apparent in the teachings set forth herein.

BRIEF DESCRIPTION OF THE FIGURES

FIG. 39 illustrates a partial view of an example article of manufacture including a computer program product that includes a computer program for executing a computer process on a computing device related to health services planning and matching, which may serve as a context for introducing one or more processes and/or devices described herein.

FIG. 40 illustrates an example device in which embodiments may be implemented related to health services planning and matching, which may serve as a context for introducing one or more processes and/or devices described herein.

DETAILED DESCRIPTION

Figure 1:
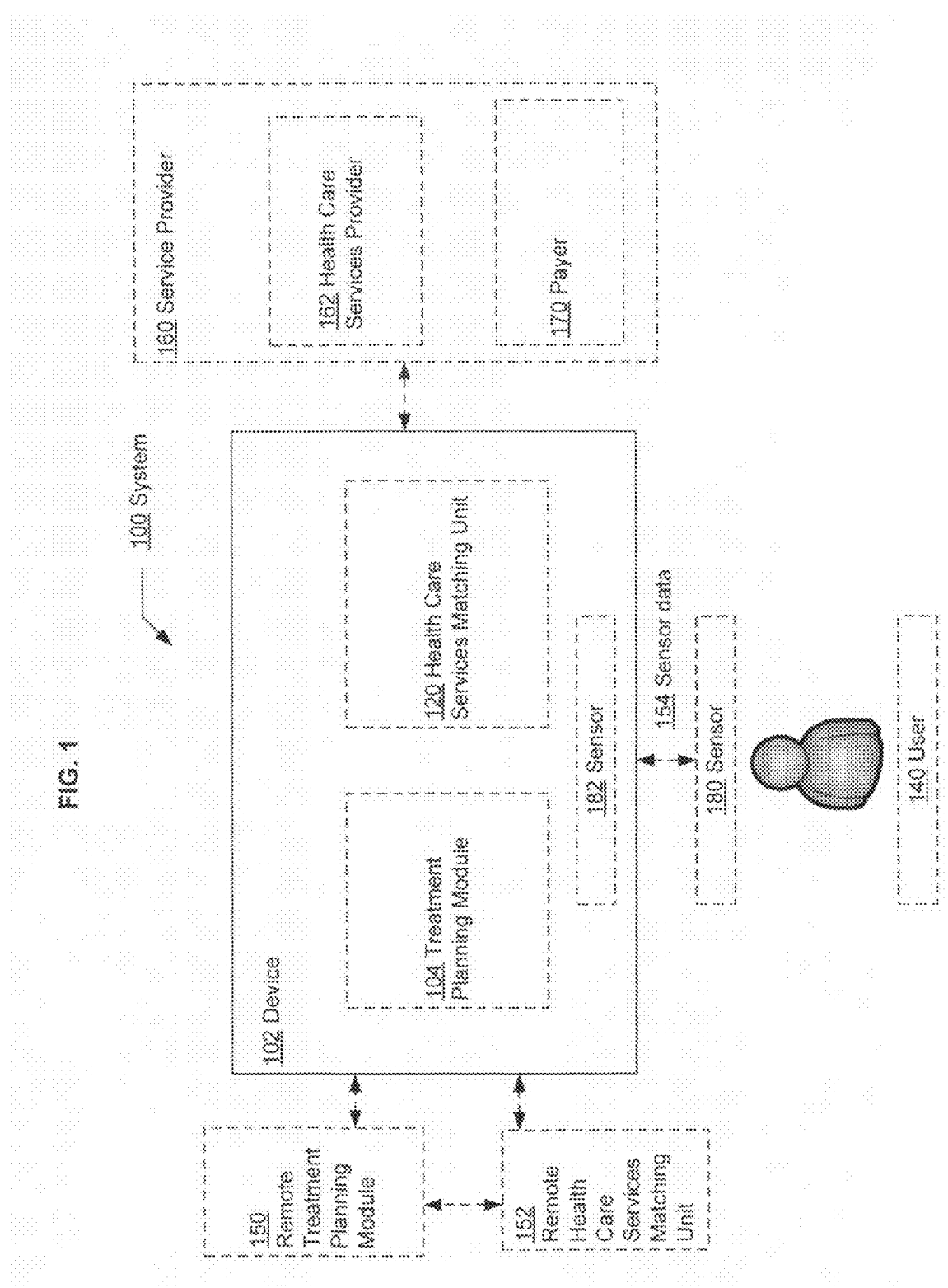
FIG. 1 illustrates an example of a health services planning and matching system in which embodiments may be implemented, perhaps in a device and/or through a network, which may serve as a context for introducing one or more processes and/or devices described herein.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

FIG. 1 illustrates an example system 100 in which embodiments may be implemented. The system 100 includes a device 102. The device 102 may contain, for example, sensor 104, and treatment planning module 104. The device 102 may communicate over a network or directly with remote treatment planning module 150 and/or remote health care services matching unit 152. User 140 may interact directly or through a user interface with device 102. Device 102 may communicate with service provider 160, which may include health care services provider 162 and/or payer 170. Device 102 may accept sensor data 154 from sensor 180 proximal to a user 140 or from remote sensor 182 to provide a plurality of health services options, for example via treatment planning module 104. Device 102 may match a selected health service option with an appropriate service provider via, for example health care services matching unit 120. Service provider 160 may include, for example, health care services provider 162 and/or payer 170.

In FIG. 1, health care services matching unit 120 may solicit a health care services option from a service provider 160. Such a solicitation may include an invitation to bid in an auction, a reverse auction, or the like. Results of such a solicitation may include matching a doctor capable of providing a chosen health care services option with the user 140 in need of the chosen health care services option, perhaps according to one or more preferences provided by the user 140. Health care services matching unit 120 may otherwise find a service provider 160 through the use of a directory or other listing of health services providers.

In FIG. 1, the device 102 is illustrated as possibly being included within a system 100. Of course, virtually any kind of computing device may be used to implement the special purpose sensor 180 and/or special purpose sensor 182, special purpose treatment planning module 104 and/or special purpose health care services matching unit 120, such as, for example, a programmed workstation, a programmed desktop computer, a programmed networked computer, a programmed server, a collection of programmed servers and/or databases, a programmed virtual machine running inside a computing device, a programmed mobile computing device, or a programmed tablet PC.

Additionally, not all of the sensor 182, sensor 180, treatment planning module 104 and/or health care services matching unit 120 need be implemented on a single computing device. For example, the sensor 182, treatment planning module 104, and/or health care services matching unit 120 may be implemented and/or operable on a remote computer, white a user interface and/or local instance of the sensor 180, treatment planning module 104, and/or health care services matching unit 120 are implemented and/or occur on a local computer. Further, aspects of the sensors 180 and 182, treatment planning module 104, and/or health care services matching unit 120 may be implemented in different combinations and implementations than that shown in FIG. 1. For example, functionality of a user interface may be incorporated into the sensor 180, treatment planning module 104, and/or health care services matching unit 120. The sensor 180, sensor 182, treatment planning module 104, and/or health care services matching unit 120 may perform simple data relay functions and/or complex data analysis, including, for example, fuzzy logic and/or traditional logic steps. Further, many methods of searching health care and/or service provider databases known in the art may be used, including, for example, unsupervised pattern discovery methods, coincidence detection methods, and/or entity relationship modeling. In some embodiments, the sensor 180, sensor 182, treatment planning module 104, and/or health care services matching unit 120 may process user input data according to health care options and/or service provider information available as updates through a network.

Treatment planning module 104 and/or health care services matching unit 120 may access data stored in virtually any type of memory that is able to store and/or provide access to information in, for example, a one-to-many, many-to-one, and/or many-to-many relationship. Such a memory may include, for example, a relational database and/or an object-oriented database, examples of which are provided in more detail herein.

Figure 2:
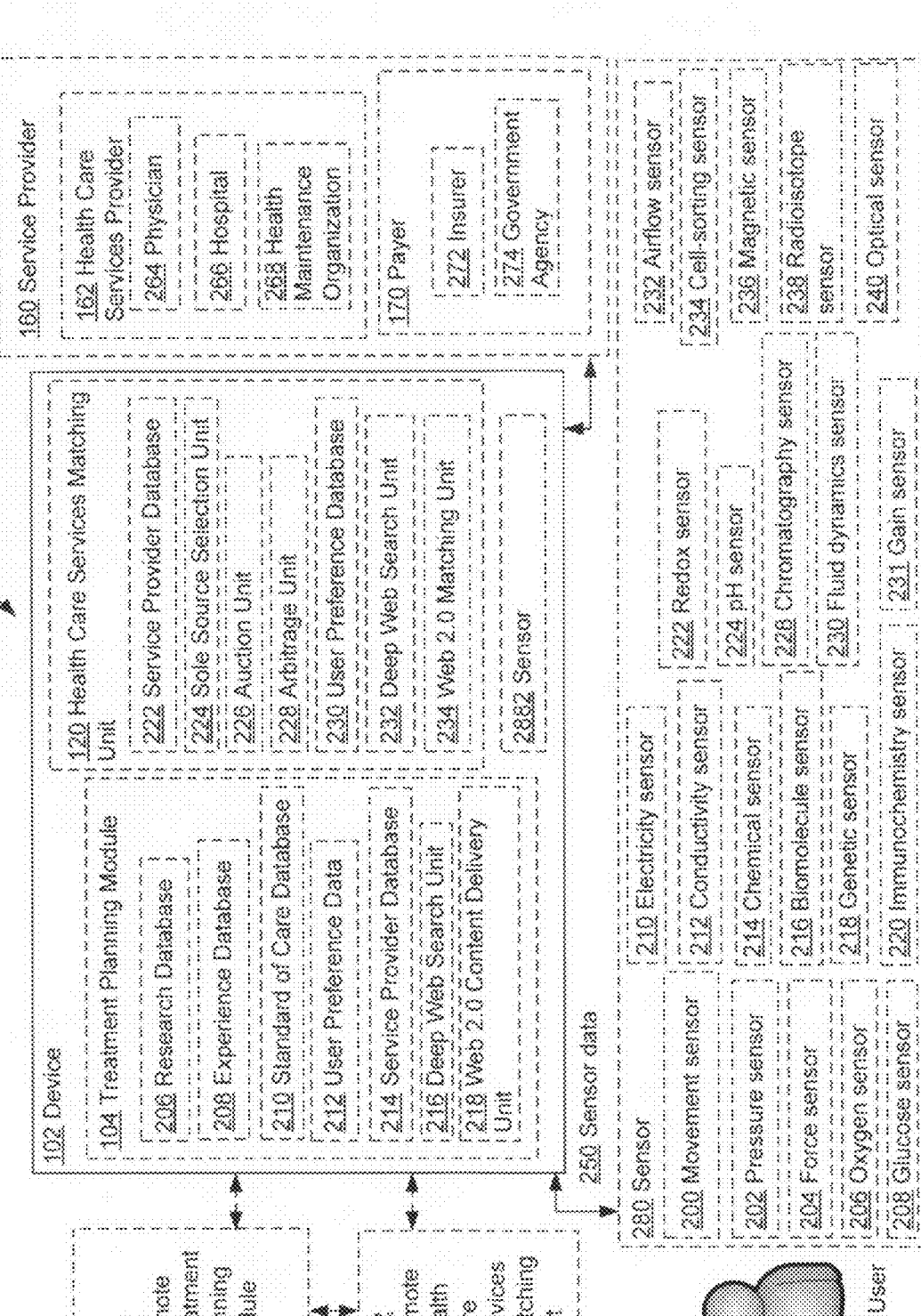
FIG. 2 illustrates certain alternative embodiments of the health services planning and matching system of FIG. 1.

FIG. 2 illustrates certain alternative embodiments of the system 100 of FIG. 1. In FIG. 2, the user 140 may interact with treatment planning module 104 and/or health care services matching unit 120 operable on the device 102. Sensor 280 may acquire sensor data 250 via movement sensor 200, pressure sensor 202, force sensor 204, oxygen sensor 206, glucose sensor 208, electricity sensor 210, conductivity sensor 212, chemical sensor 214, biomolecule sensor 216, genetic sensor 218, immunochemistry sensor 220, redox sensor 222, pH sensor 224, chromatography sensor 228, fluid dynamics sensor 230, gain sensor 231, airflow sensor 232, cell-sorting sensor 234, magnetic sensor 236, radioisotope sensor 238, and/or optical sensor 240.

Alternatively, remote sensor 282 may generate sensor data from signals received from a distance. Examples of such remote sensing include the use of signal processing algorithms for a wireless sensor that can classify different types of motion and closely monitor a person's breathing and/or heart rate. For example, this type of sensor is useful in monitoring premature babies in a neonatal intensive care unit. Premature infants have very sensitive and fragile skin, which can make it difficult to directly attach sensors to them. A remote sensor can wirelessly monitor an infant's movements, including breathing and heart rate. Similarly, the sensor can be installed in a home for elder care or other outpatient monitoring. See also U.S. Pat. No. 6,315,719; U.S. Pat. No. 7,387,607; and U.S. Pat. No. 7,424,409; each of which is incorporated herein by reference.

Sensor data 250 may be accepted by treatment planning module 104 implemented on the device 102. The device 102 can communicate over a network with remote treatment planning module 150 and/or remote health care services matching unit 152. Treatment planning module 104 may include, for example, research database 206, experience database 208, standard of care database 210, user preference data 212, service provider database 214, Deep Web search unit 216, and/or Web 2.0 content delivery unit 218. The treatment planning module 104 may access and send health-related services options 242 to user 140. User 140 may subsequently choose and send health-related services selection 244 including a desired health service option from among a plurality of health services options to device 102 including health care services matching unit 120. Health care services matching unit 120 may include, for example, service provider database 222, sole source selection unit 224, auction unit 226, 228 arbitrage unit 228, user preference database 230, Deep Web search unit 232, and/or Web 2.0 matching unit 234. Health care services matching unit 120 may communicate directly or over a network with service provider 160 to obtain a suitable health-related service according to health-related services selection 244 and any user preference contained, for example, in user preference database 230. Service provider 160 may include health care services provider 162 and/or payer 170. Health care services provider 162 may include, for example, physician 264, hospital 266, and/or health maintenance organization 268. Payer 170 may include, for example, insurer 272, and/or government agency 274. Health care services matching unit 120 may then present matched health-related service 246 to user 140.

In this way, the user 140, who may be using a mobile device that is connected through a network with the system 100 and/or device 102 (e.g., in an office, outdoors and/or in a public environment), may generate a plurality of health service options as if the user 140 were interacting locally with the device 102 and/or system 100.

As referenced herein, the treatment planning module 104 and/or health care services matching unit 120 may be used to perform various data querying and/or recall techniques with respect to sensor data 250 and/or a plurality of health service options, in order to obtain and/or present a plurality of health service options. For example, where the sensor data 250 is organized, keyed to, and/or otherwise accessible using one or more reference health-related status indicators such as symptom, disease, diagnosis, or the like, treatment planning module 104 and/or health care services matching unit 120 may employ various Boolean, statistical, and/or semi-boolean searching techniques to match sensor data 250 with one or more indications of health status and/or one or more relevant health-related services options. Similarly, for example, where user preference data is organized, keyed to, and/or otherwise accessible using one or more service provider 160 interest profiles, various Boolean, statistical, and/or semi-boolean searching techniques may be performed by health care services matching unit 120 to match a given health-related services selection 244 with a service provider 160 to present, for example, a matched health-related service 246.

Many examples of databases and database structures may be used in connection with the treatment planning module 104 and/or health care services matching unit 120. Such examples include hierarchical models (in which data is organized in a tree and/or parent-child node structure), network models (based on set theory, and in which multiparent structures per child node are supported), or object/relational models (combining the relational model with the object-oriented model).

Still other examples include various types of eXtensible Mark-up Language (XML) databases. For example, a database may be included that holds data in some format other than XML, but that is associated with an XML interface for accessing the database using XML. As another example, a database may store XML data directly. Additionally, or alternatively, virtually any semi-structured database may be used, so that context may be provided to/associated with stored data elements (either encoded with the data elements, or encoded externally to the data elements), so that data storage and/or access may be facilitated.

Such databases, and/or other memory storage techniques, may be written and/or implemented using various programming or coding languages. For example, object-oriented database management systems may be written in programming languages such as, for example, C++ or Java. Relational and/or object/relational models may make use of database languages, such as, for example, the structured query language (SQL), which may be used, for example, for interactive queries for information and/or for gathering and/or compiling data from the relational database(s).

For example, SQL or SQL-like operations over one or more reference health attribute and/or reference service provider may be performed, or Boolean operations using a reference health attribute and/or reference service provider may be performed. For example, weighted Boolean operations may be performed in which different weights or priorities are assigned to one or more of the reference health-related status attributes and/or reference service providers, including reference health conditions and/or reference service providers associated with various reference health-related status attributes, perhaps relative to one another. For example, a number-weighted, exclusive-OR operation may be performed to request specific weightings of desired (or undesired) health reference data or service providers to be included or excluded. Reference health-related status attributes may include normal physiological values for such health-related things as pain, reaction time, body or eye movement, memory, alertness, blood pressure, or the like. Such normal physiological values may be "normal" relative to the user 140, to a subpopulation to which the user 140 belongs, or to a general population. Similarly, reference service providers may be associated with, for example, the general medical community, a medical specialty, a local geographical area or the like.

Following are a series of flowcharts depicting implementations. For ease of understanding, the flowcharts are organized such that the initial flowcharts present implementations via an example implementation and thereafter the following flowcharts present alternate implementations and/or expansions of the initial flowchart(s) as either subcomponent operations or additional component operations building on one or more earlier-presented flowcharts. Those having skill in the art will appreciate that the style of presentation used herein (e.g., beginning with a presentation of a flowchart presenting an example implementation and thereafter providing additions to and/or further details in subsequent flowcharts) generally allows for a rapid and easy understanding of the various process implementations. In addition, those skilled in the art will further appreciate that the style of presentation used herein also lends itself well to modular and/or object-oriented program design paradigms.

Figure 3:
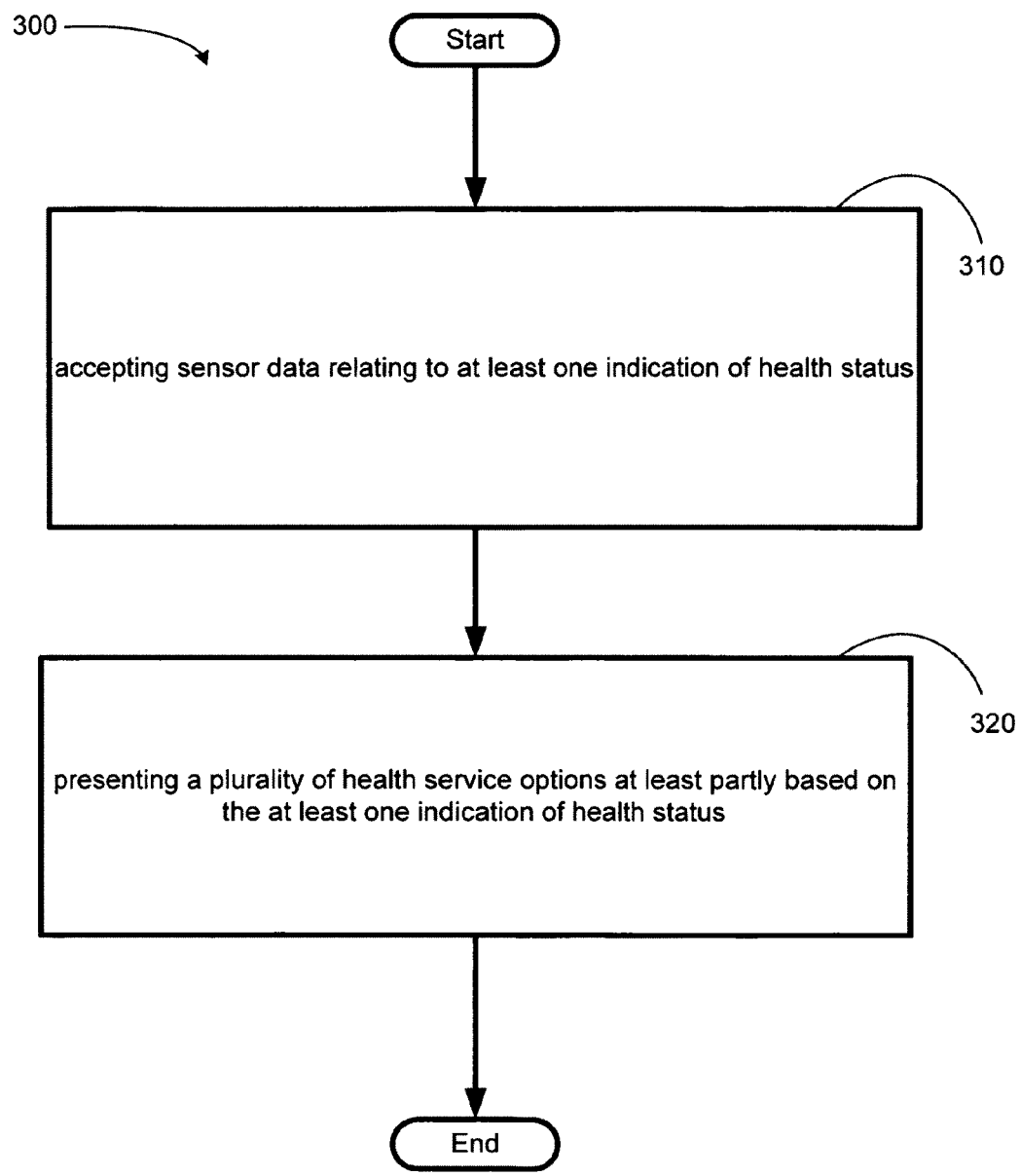
FIG. 3 illustrates an example of an operational flow representing example operations related to health services planning and matching, which may serve as a context for introducing one or more processes and/or devices described herein.

FIG. 3 illustrates an operational flow 300 representing example operations related to health services planning and matching. In FIG. 3 and in following figures that include various examples of operational flows, discussion and explanation may be provided with respect to the above-described system environments of FIGS. 1-2, and/or with respect to other examples and contexts. However, it should be understood that the operational flows may be executed in a number of other environments and contexts including that of FIGS. 17 and 18, and/or in modified versions of FIGS. 1-2. Also, although the various operational flows are presented in the sequences illustrated, it should be understood that the various operations may be performed in other orders than those which are illustrated, or may be performed concurrently.

After a start operation, operation 310 depicts accepting sensor data relating to at least one indication of health status. For example, treatment planning module 104 and/or device 102 may accept sensor data relating to at least one indication of health status. In one embodiment, sensor 280 may transmit sensor data 250 to device 102 relating to a symptom or disease. The user 140 may be a patient having a medical condition, an individual experiencing one or more symptoms, an asymptomatic individual, or the like. Sensor data relating to at least one indication of health status may also include indications for cosmetic enhancement, pregnancy, or improvement in athletic performance. In another embodiment, treatment planning module 104 accepting blood pressure sensor data indicating a sustained rise in blood pressure over time may present a plurality of health service options based on the indication of high blood pressure received from the blood pressure sensor. The user 140 may then analyze the plurality of health service options to determine whether or not to proceed in finding a health service provider for the presented options for addressing the detected high blood pressure. In one embodiment, user 140 may wish to find a health service provider to address one of a plurality of presented health service options. In this case, health care services matching unit 120 may provide, for example, an auction system by which user 140 can procure the desired health care service, for example, in a given geographic area at a competitive price.

Operation 320 depicts presenting a plurality of health service options at least partly based on the at least one indication of health status. For example, treatment planning module 104 and/or device 102 may present a plurality of health service options at least partly based on the at least one indication of health status. In one embodiment, treatment planning module 104 may, based on accepted sensor data, present a set of health service options according to one or more diagnoses or treatment paths corresponding to symptom(s) or conditions.

In one embodiment, a stochastic model can be built to describe an image, for example a medical image. The stochastic model may then be used to compare other images in the same way that it compares other data sequences. Such a system is useful in automatic screening of medical image data to identify features of interest. The system can be used to compare images of the same patient taken at different times, for example to monitor progress of a tumor, or it could be used to compare images taken from various patients with a standard image.

D. Nikovski, "Constructing Bayesian Networks for Medical Diagnosis from Incomplete and Partially Correct Statistics," IEEE Transactions on Knowledge and Data Engineering, Vol. 12:4, pp. 509-516 (2000). The paper discusses several knowledge engineering techniques for the construction of Bayesian networks for medical diagnostics when the available numerical probabilistic information is incomplete or partially correct. This situation occurs often when epidemiological studies publish only indirect statistics and when significant unmodeled conditional dependence exists in the problem domain. While nothing can replace precise and complete probabilistic information, still a useful diagnostic system can be built with imperfect data by introducing domain-dependent constraints. We propose a solution to the problem of determining the combined influences of several diseases on a single test result from specificity and sensitivity data for individual diseases. We also demonstrate two techniques for dealing with unmodeled conditional dependencies in a diagnostic network. These techniques are discussed in the context of an effort to design a portable device for cardiac diagnosis and monitoring from multimodal signals.

Figure 4:
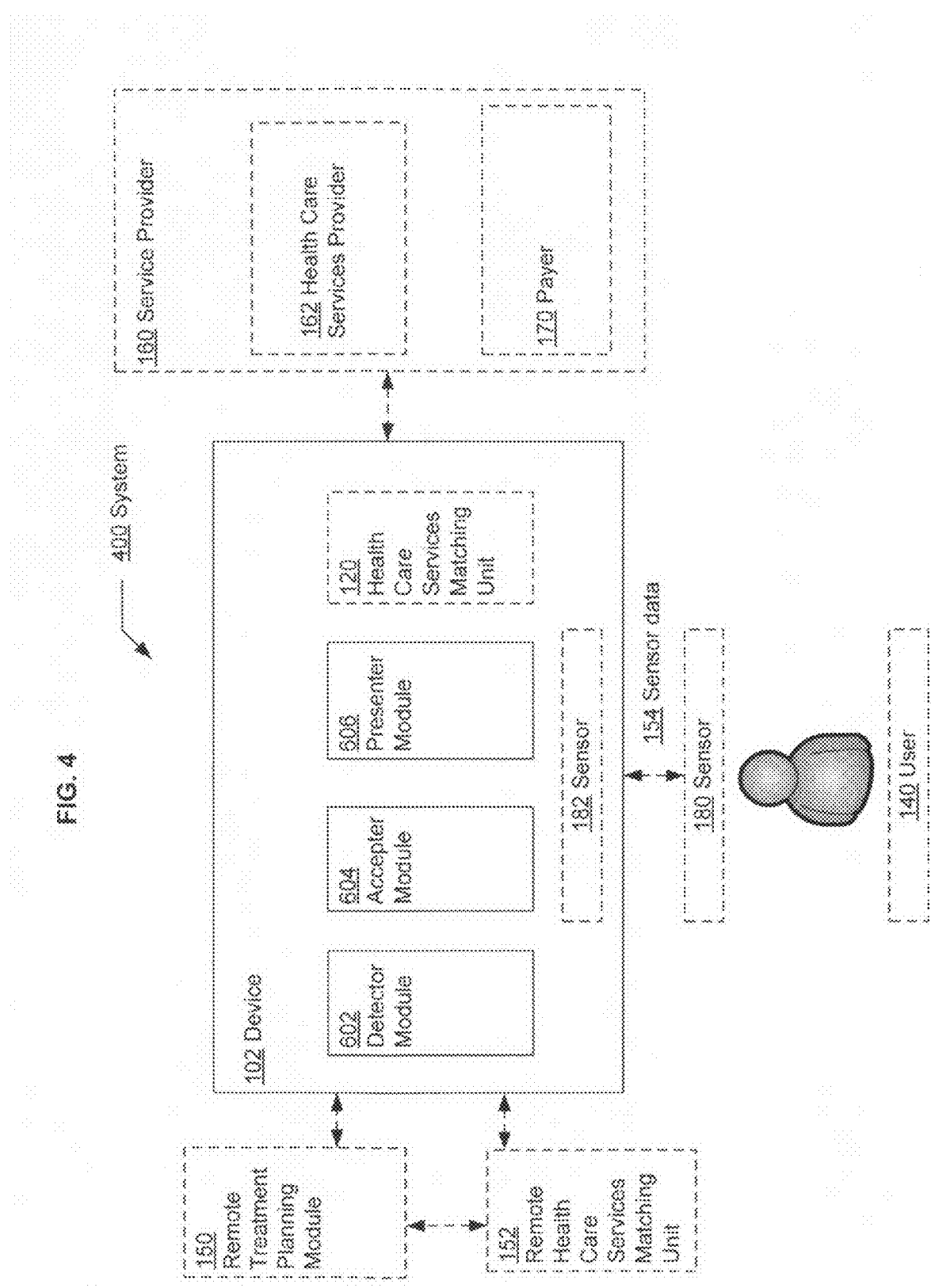
FIG. 4 illustrates an example of a health services planning and matching system in which embodiments may be implemented, perhaps in a device and/or through a network, which may serve as a context for introducing one or more processes and/or devices described herein.

FIG. 4 illustrates an example system 400 in which embodiments may be implemented. The system 400 includes a device 102. The device 102 may contain, for example, detector module 602, accepter module 604, and/or presenter module 606. The device 102 may communicate over a network or directly with remote treatment planning module 150 and/or remote health care services matching unit 152. User 140 may interact directly or through a user interface with device 102. Device 102 may communicate with service provider 160, which may include health care services provider 162 and/or payer 170. Device 102 may accept user input to provide one or more health services options, for example via detector module 602 and/or accepter module 604. Device 102 may accept a selected health service option and match it with an appropriate service provider via, for example health care services matching unit 120. Service provider 160 may include, for example, health care services provider 162 and/or payer 170.

In FIG. 4, the device 102 is illustrated as possibly being included within a system 400. Of course, virtually any kind of computing device may be used to implement the special purpose health care services matching unit 120, special purpose detector module 602, special purpose accepter module 604, and/or special purpose presenter module 606, such as, for example, a workstation, a desktop computer, a networked computer, a server, a collection of servers and/or databases, a virtual machine running inside a computing device, a mobile computing device, or a tablet PC.

Additionally, not all of the health care services matching unit 120, detector module 602, accepter module 604, and/or presenter module 606 need be implemented on a single computing device. For example, health care services matching unit 120, detector module 602, accepter module 604, and/or presenter module 606 may be implemented and/or operable on a remote computer, while a user interface and/or local instance of the health care services matching unit 120, detector module 602, accepter module 604, and/or presenter module 606 are implemented and/or occur on a local computer. Further, aspects of health care services matching unit 120, detector module 602, accepter module 604, and/or presenter module 606 may be implemented in different combinations and implementations than that shown in FIG. 4. For example, functionality of a user interface may be incorporated into the health care services matching unit 120, detector module 602, accepter module 604, and/or presenter module 606. The health care services matching unit 120, detector module 602, accepter module 604, and/or presenter module 606 may perform simple data relay functions and/or complex data analysis, including, for example, fuzzy logic and/or traditional logic steps. Further, many methods of searching health care and/or service provider databases known in the art may be used, including, for example, unsupervised pattern discovery methods, coincidence detection methods, and/or entity relationship modeling. In some embodiments, health care services matching unit 120, detector module 602, accepter module 604, and/or presenter module 606 may process user input data according to health care options and/or service provider information available as updates through a network.

Health care services matching unit 120, detector module 602, accepter module 604, and/or presenter module 606 may access data stored in virtually any type of memory that is able to store and/or provide access to information in, for example, a one-to-many, many-to-one, and/or many-to-many relationship. Such a memory may include, for example, a relational database and/or an object-oriented database, examples of which are provided in more detail herein.

Figure 5:
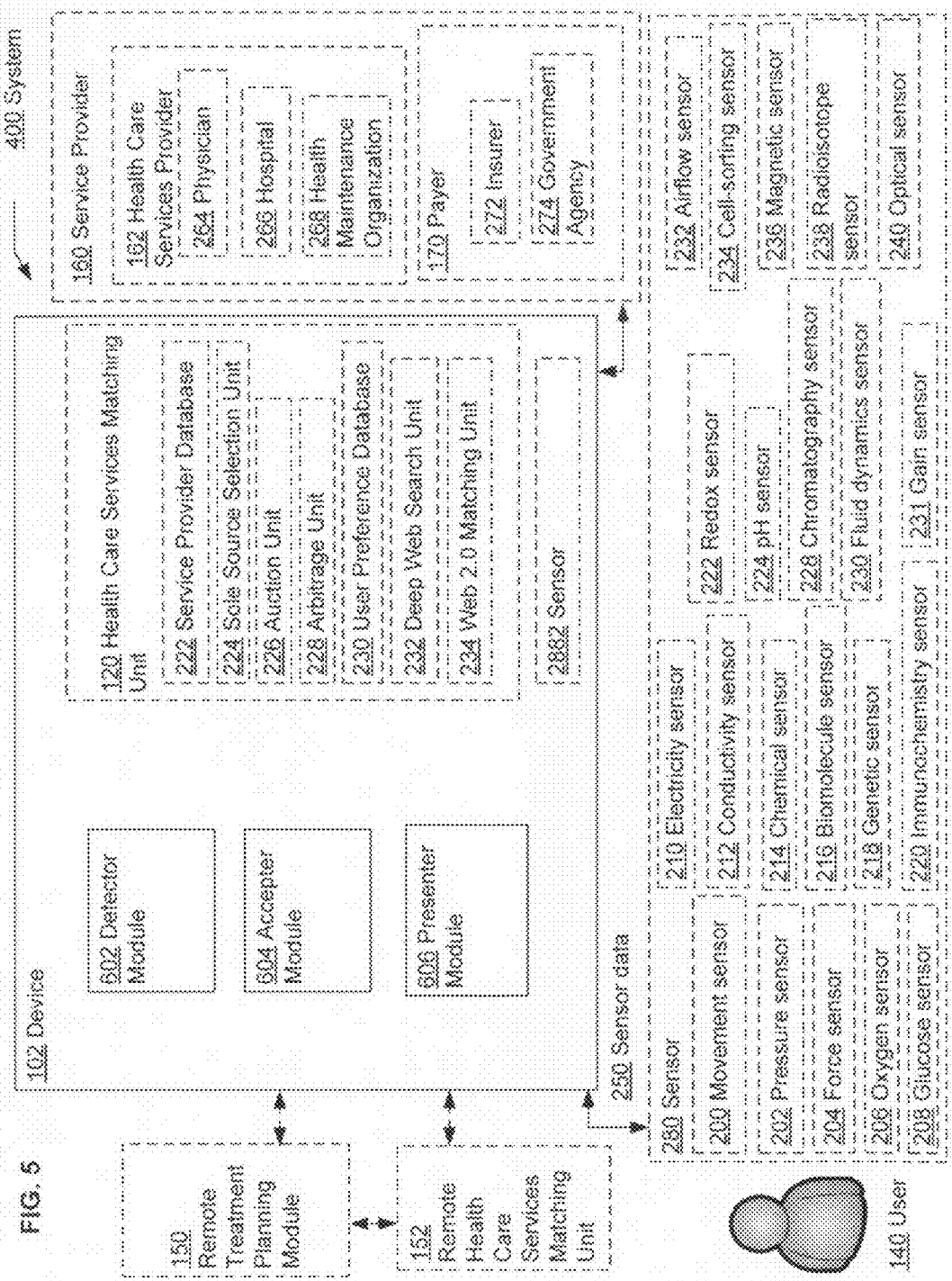
FIG. 5 illustrates certain alternative embodiments of the health services planning and matching system of FIG. 4.

FIG. 5 further illustrates system 400 including device 102, which may further include health care services matching module 120, sensor 2882, detector module 602, accepter module 604, and/or presenter module 606. Health care services matching module 120 may include service provider database 222, sole source selection unit 224, auction unit 226, arbitrage unit 228, user preference database 230, deep web search unit 232 and/or Web 2.0 matching unit 234. Device 102 may communicate with remote treatment planning module 150, remote health care services matching unit 152, and/or service provider 160. Service provider 160 may include health care services provider 162 and/or payer 170. Health care services provider 162 may include physician 264, hospital 266, and/or health maintenance organization 268. Payer 170 may include insurer 272 and/or government agency 274. Additionally, device 102 may accept sensor data 250 from and/or communicate with sensor 280. Sensor 280 may include movement sensor 200, pressure sensor 202, force sensor 204, oxygen sensor 206, glucose sensor 208, electricity sensor 210, conductivity sensor 212, chemical sensor 214, biomolecule sensor 216, genetic sensor 218, immunochemistry sensor 220, redox sensor 222, pH sensor 224, chromatography sensor 228, fluid dynamics sensor 230, gain sensor 231, airflow sensor 232, cell-sorting sensor 234, magnetic sensor 236, radioisotope sensor 238, and/or optical sensor 240.

Figure 6:
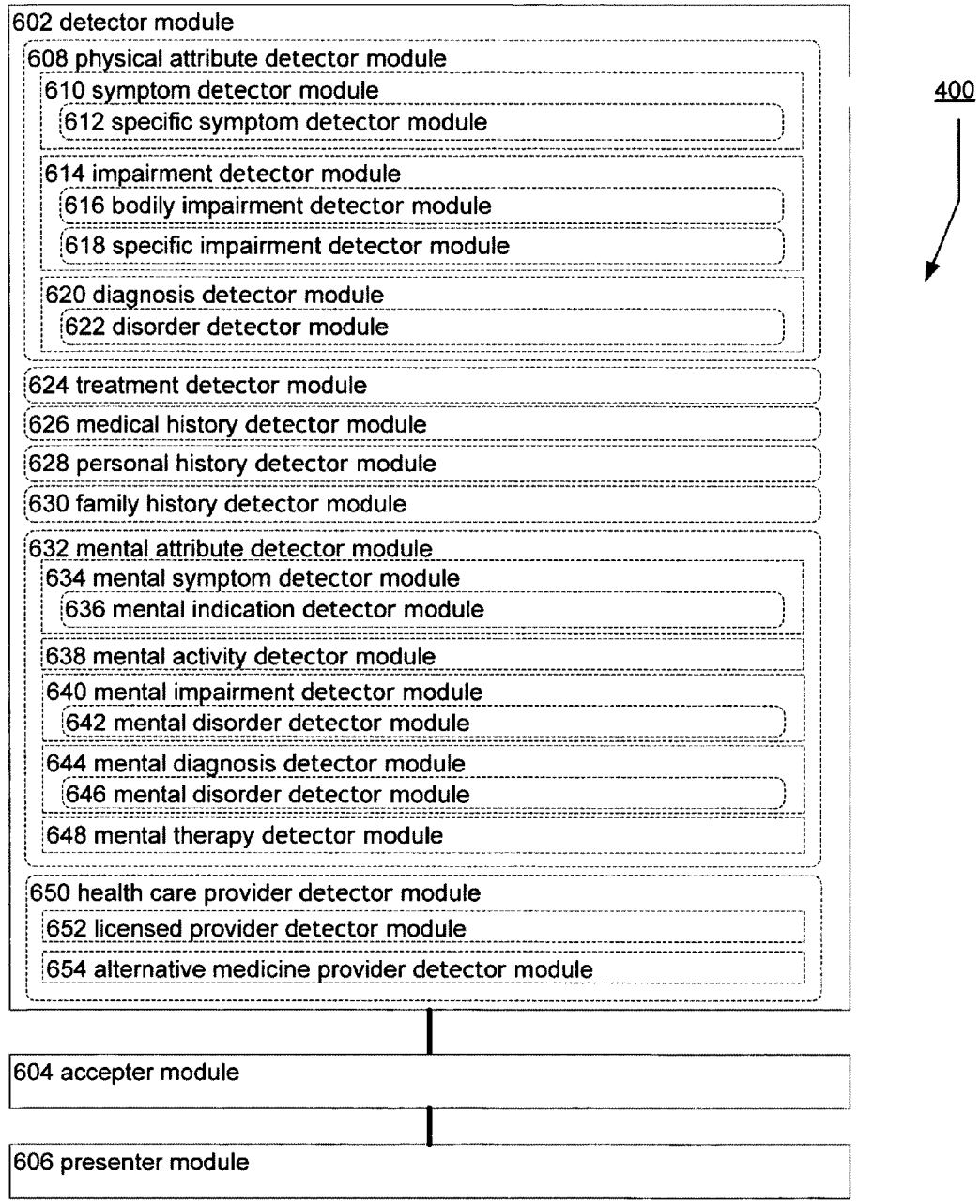
FIG. 6 illustrates certain alternative embodiments of the health services planning and matching system of FIG. 4.

FIG. 6 further illustrates system 400 including detector module 602, accepter module 604, and/or presenter module 606. Detector module 602 may include physical attribute accepter module 608, treatment accepter module 624, medical history accepter module 626, personal history accepter module 628, family history accepter module 630, mental attribute accepter module 632, and/or health care provider accepter module 650. Physical attribute accepter module 608 may include symptom accepter module 610, impairment accepter module 614, and/or diagnosis accepter module 620. Symptom accepter module 610 may include specific symptom accepter module 612. Impairment accepter module 614 may include bodily impairment accepter module 616 and/or specific impairment accepter module 618. Diagnosis accepter module 620 may include disorder accepter module 622. Mental attribute accepter module 632 may include mental symptom accepter module 634, mental activity accepter module 638, mental impairment accepter module 640, mental diagnosis accepter module 644, and/or mental therapy accepter module 648. Mental symptom accepter module 634 may include mental indication accepter module 636. Mental impairment accepter module 640 may include mental disorder accepter module 642. Mental diagnosis accepter module 644 may include mental disorder accepter module 646. Health care provider accepter module 650 may include licensed provider accepter module 652 and/or alternative medicine provider accepter module 654.

Figure 7:
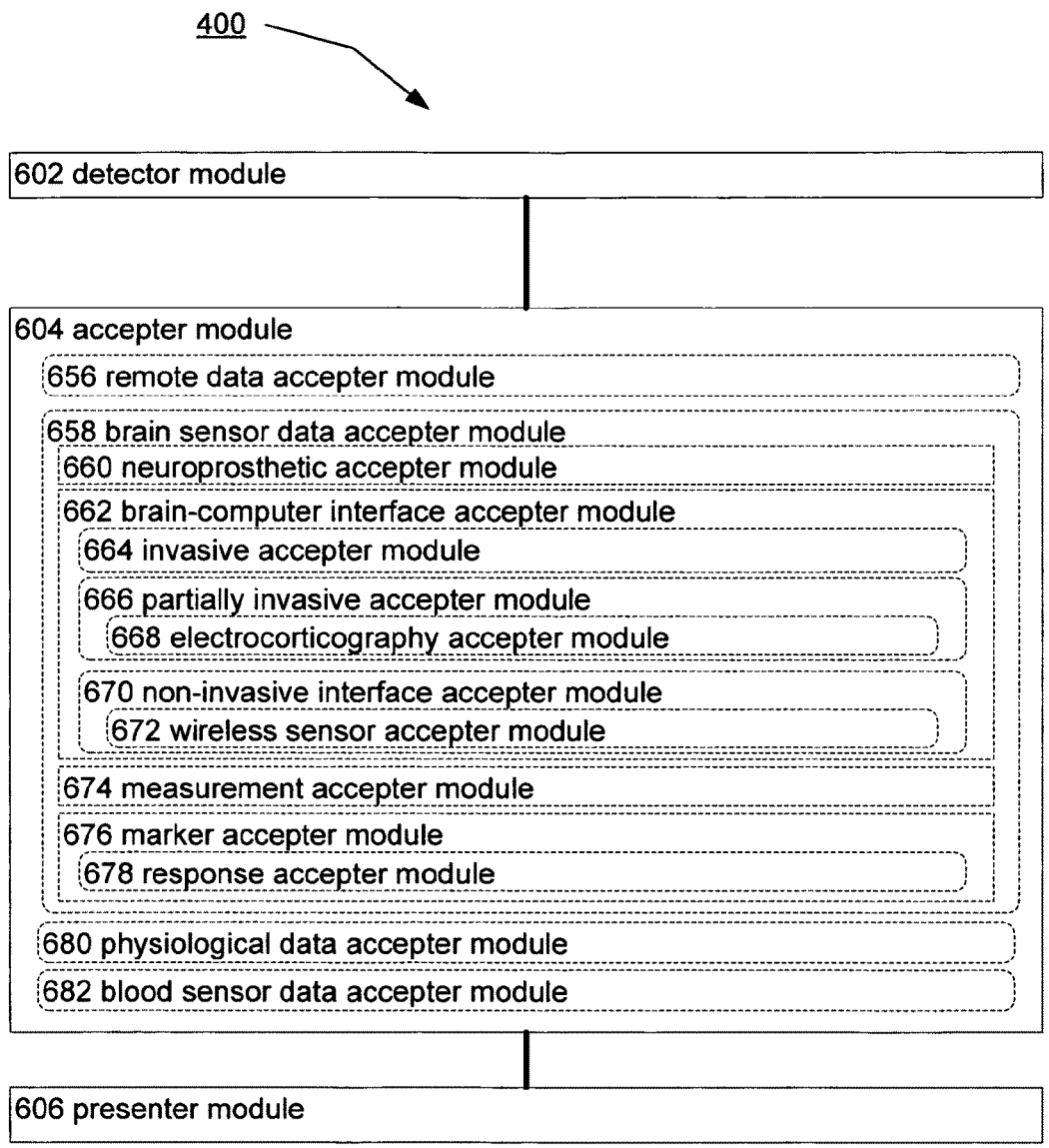
FIG. 7 illustrates certain alternative embodiments of the health services planning and matching system of FIG. 4.

FIG. 7 further illustrates system 400 including detector module 602, accepter module 604, and/or presenter module 606. Accepter module 604 may include remote data accepter module 656, brain sensor data accepter module 658, physiological data accepter module 680, and/or blood sensor data accepter module 682. Brain sensor data accepter module 658 may include neuroprosthetic accepter module 660, brain-computer interface accepter module 662, measurement accepter module 674, and/or marker accepter module 676. Brain-computer interface accepter module 662 may include invasive accepter module 664, partially invasive accepter module 666, and/or non-invasive interface accepter module 670. Partially invasive accepter module 666 may include electrocorticography accepter module 668. Non-invasive interface accepter module 670 may include wireless sensor accepter module 672. Marker accepter module 676 may include response accepter module 678.

Figure 8:
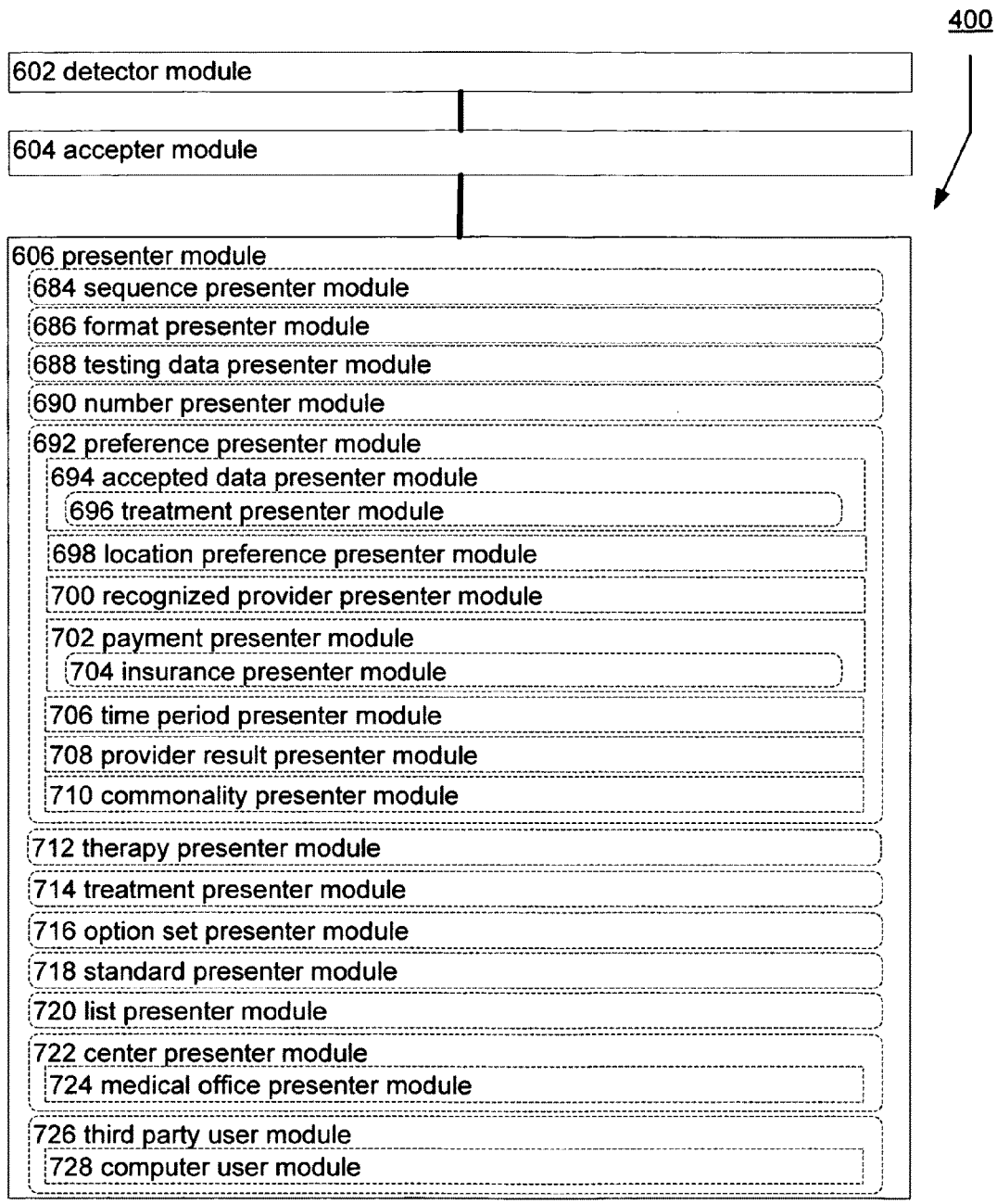
FIG. 8 illustrates certain alternative embodiments of the health services planning and matching system of FIG. 4.

FIG. 8 further illustrates system 400 including detector module 602, accepter module 604, and/or presenter module 606. Presenter module 606 may include sequence presenter module 684, format presenter module 686, testing data presenter module 688, number presenter module 690, preference presenter module 692, therapy presenter module 712, treatment presenter module 714, option set presenter module 716, standard presenter module 718, list presenter module 720, center presenter module 722, and/or third party user module 726. Preference presenter module 692 may include accepted data presenter module 694, location preference presenter module 698, recognized provider presenter module 700, payment presenter module 702, time period presenter module 706, provider result presenter module 708, and/or commonality presenter module 710. Accepted data presenter module 694 may include treatment presenter module 696. Payment presenter module 702 may include insurance presenter module 704. Center presenter module 722 may include medical office presenter module 724. Third party user module 726 may include computer user module 728.

Figure 9:
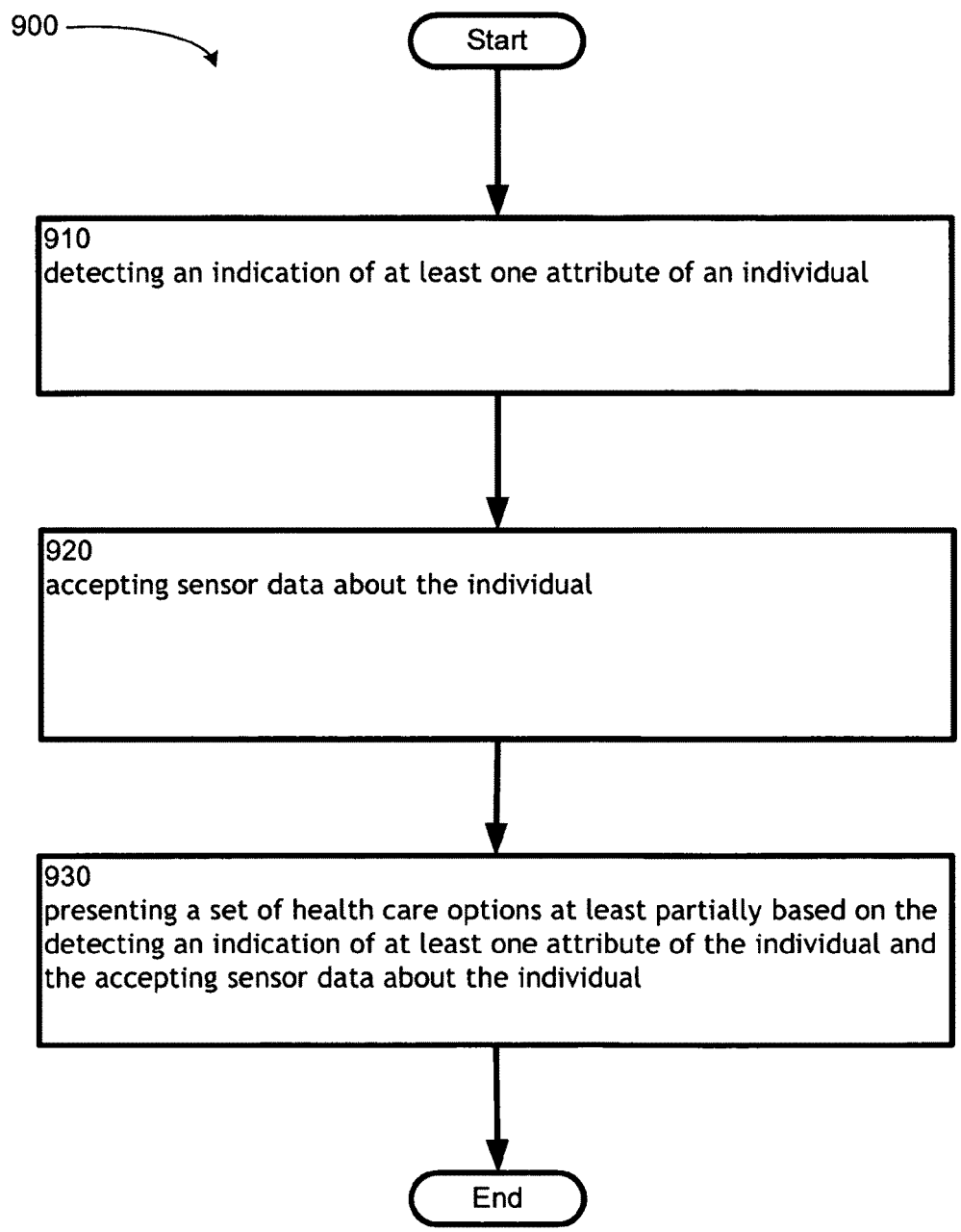
FIG. 9 illustrates an example of an operational flow representing example operations related to health services planning and matching, which may serve as a context for introducing one or more processes and/or devices described herein.

FIG. 9 illustrates an operational flow 900 representing example operations related to detecting an indication of at least one attribute of an individual, accepting sensor data about the individual, and presenting a set of health care options at least partially based on the detecting an indication of at least one attribute of the individual and the accepting sensor data about the individual. In FIG. 9 and in following figures that include various examples of operational flows, discussion and explanation may be provided with respect to the above-described examples of FIGS. 4 through 8, and/or with respect to other examples and contexts. However, it should be understood that the operational flows may be executed in a number of other environments and contexts, and/or in modified versions of FIGS. 4 through 8. Also, although the various operational flows are presented in the sequence(s) illustrated, it should be understood that the various operations may be performed in other orders than those which are illustrated, or may be performed concurrently.

After a start operation, the operational flow 900 moves to operation 910. Operation 910 depicts detecting an indication of at least one attribute of an individual. For example, as shown in FIGS. 4 through 8, detector module 602 can detect at least one attribute of an individual. In an embodiment, accepter module 602 may accept a personal medical history, for example, that includes an individual's blood pressure history. Accepting at least one attribute of an individual may serve to better indicate an individual's medical status to a health care provider, for example. Some other examples of an attribute of an individual may include results from a patient interview, results from an individual's input into, for example, a computer station, and/or a medical history. In some instances, accepter module 602 may include a computer processor.

Then, operation 920 depicts accepting sensor data about the individual. For example, as shown in FIGS. 4 through 8, accepter module 604 can accept sensor data about the individual. In an embodiment, accepter module 604 may accept data from a blood pressure cuff while measuring an individual's blood pressure. Accepting sensor data may serve further validate or invalidate the accepted indication of an individual's attribute. Some examples of a sensor may include a movement sensor, a glucose sensor, an oxygen sensor, a chemical sensor, a thermometer, an optical sensor, and/or a biochip. In some instances, accepter module 604 may include a computer processor.

Then, operation 930 depicts presenting a set of health care options at least partially based on the detecting an indication of at least one attribute of the individual and the accepting sensor data about the individual. For example, as shown in FIGS. 4 through 8, presenter module 606 may present a set of health care options at least partially based on the accepting an indication of at least one attribute of the individual and the accepting sensor data about the individual. In one embodiment, presenter module 606 may, based on at least one accepted attribute of an individual and accepted sensor data, present a set of health care options according to one or more diagnoses and/or treatment paths corresponding to symptom(s) or conditions indicated by the accepted attribute(s) of an individual and accepted sensor data. Some examples of presenting a plurality of health service options may include presenting at least one physician, medication, exercise, health care facility, and/or medical procedure. In some instances, presenter module 606 may include a computer processor.

Figure 10:
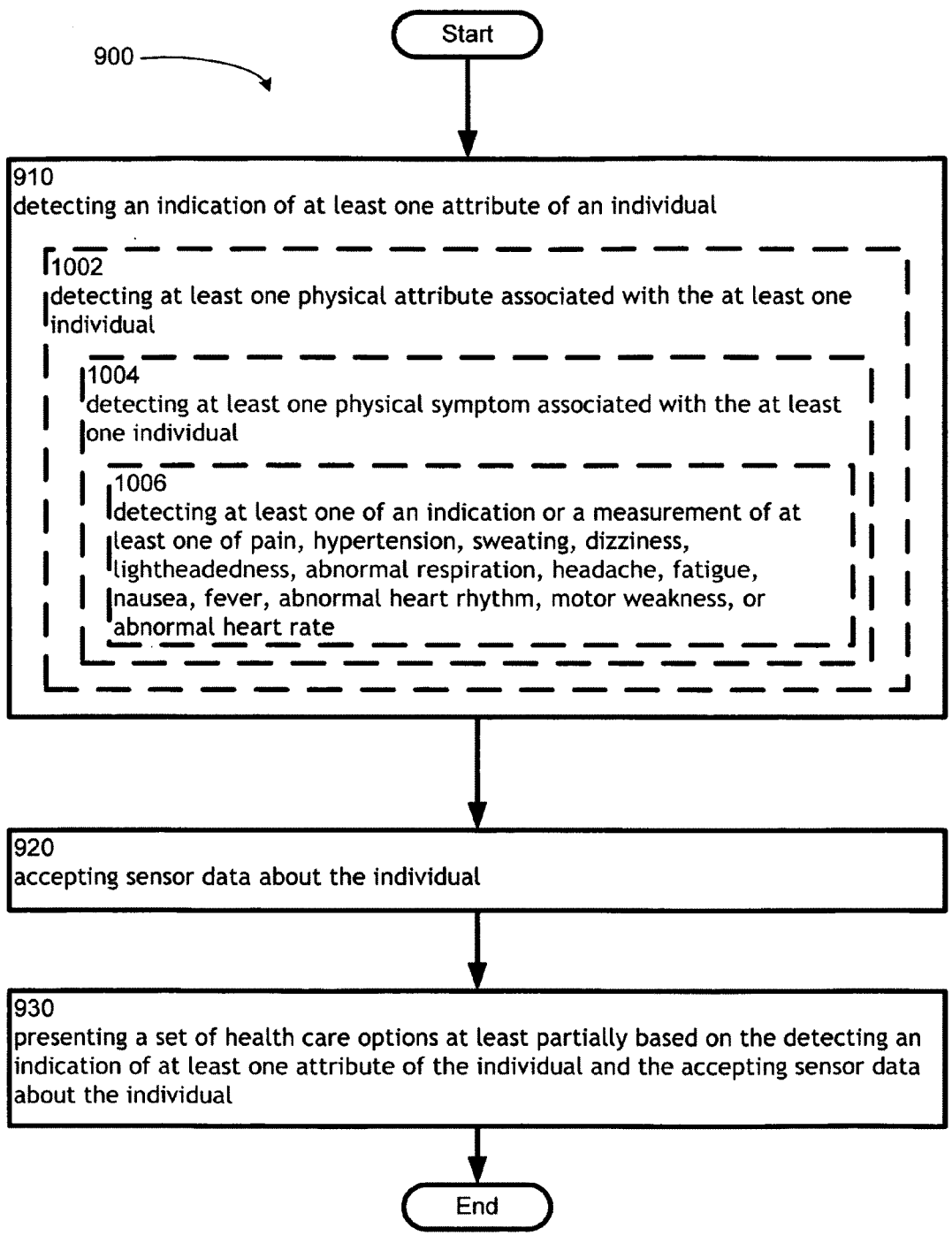
FIG. 10 illustrates an alternative embodiment of the operational flow of FIG. 9.

FIG. 10 illustrates alternative embodiments of the example operational flow 900 of FIG. 9. FIG. 10 illustrates example embodiments where operation 910 may include at least one additional operation. Additional operations may include operation 902, operation 904, and/or operation 906.

Operation 1002 illustrates detecting at least one physical attribute associated with the at least one individual. For example, as shown in FIGS. 4 through 8, physical attribute detector module 608 may detect at least one physical attribute associated with the at least one individual. In one instance, physical attribute detector module 608 can detect a physical attribute associated with an individual, for example a weight history. A physical attribute may include an attribute that may be described and/or detected using senses, that has substance and/or a material existence, and/or that may be acted upon by physical force. Some examples of a physical attribute may include a biochemical measurement such as blood sugar level, an appearance, and/or a physiological measurement such as blood pressure, and/or skin conductivity. In some instances, physical attribute detector module 608 may include a computer processor.

Further, operation 1004 illustrates detecting at least one physical symptom associated with the at least one individual. For example, as shown in FIGS. 4 through 8, symptom detector module 610 may detect at least one physical symptom associated with the at least one individual. In one example, symptom detector module 610 can detect from an individual and/or user interface a physical symptom, for example an indication of influenza (e.g., a fever). A physical symptom may include a manifestation, sign, and/or an indication of the presence of a disease and/or some other bodily disorder and/or abnormality. Some examples of a physical symptom may include pain, swelling, fever, rash, and/or discoloration. In some instances, symptom detector module 610 may include a computer processor.

Further, operation 1006 illustrates detecting at least one of an indication or a measurement of at least one of pain, hypertension, sweating, dizziness, lightheadedness, abnormal respiration, headache, fatigue, nausea, fever, abnormal heart rhythm, motor weakness, or abnormal heart rate. For example, as shown in FIGS. 4 through 8, specific symptom detector module 612 can detect at least one of an indication or a measurement of at least one of pain, hypertension, sweating, dizziness, lightheadedness, abnormal respiration, headache, fatigue, nausea, fever, abnormal heart rhythm, motor weakness, or abnormal heart rate. In one example, specific symptom detector module 612 can detect an indication of an individual's pain and a measurement of high blood pressure from a patient interview. Pain may include a sensation of somatic hurt or disorder and may include acute pain and/or chronic pain. Hypertension may include chronically elevated blood pressure and may be considered to be present when a person's systolic blood pressure is consistently about 140 mm Hg or greater and/or their diastolic blood pressure is consistently about 90 mm Hg or greater. Sweating may include the excessive production and/or evaporation of fluid excreted by the sweat glands in the skin. Dizziness may include vertigo, disequilibrium, pre-syncope, and/or other balance disorders. Lightheadedness may include a sensation of dizziness and/or fainting. Abnormal respiration may include atypical and/or pathological breathing patterns. Headache may include pain in the head, neck, and/or upper back and may be a symptom of tension, migraine, dehydration, eye strain, sinus disorders, and/or low blood sugar. Fatigue may include muscle weakness and/or lack of strength. Nausea may include the sensation of unease and/or discomfort in the stomach, often with the urge to vomit. Fever may include an increase in internal body temperature to levels above normal. Abnormal heart rhythm may include inconsistent and/or irregular rhythmic contractions in the heart such as sick sinus syndrome, atrial fibrillation, and/or atrial flutter. Motor weakness may include a lack of strength and/or function in the portion of the central nervous system involved in movement. An abnormal heart rate may include an irregular heart contraction frequency such as bradycardia, tachycardia or the like. In some instances, specific symptom detector module 612 may include a computer processor.

Figure 11:
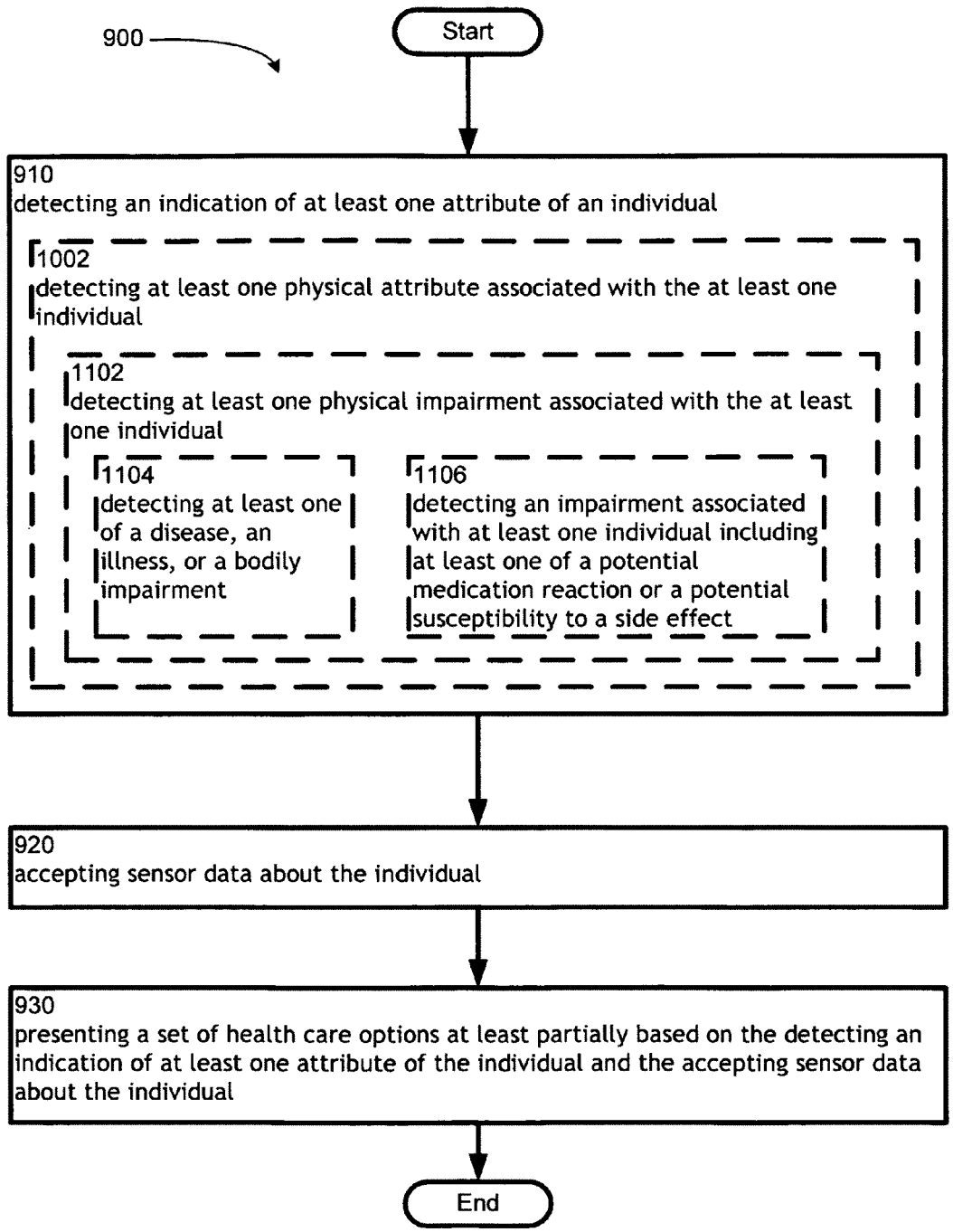
FIG. 11 illustrates an alternative embodiment of the operational flow of FIG. 9.

FIG. 11 illustrates alternative embodiments of the example operational flow 800 of FIG. 8. FIG. 10 illustrates example embodiments where operation 910 may include at least one additional operation. Additional operations may include operation 1002, operation 1004, and/or operation 1006.

Further, operation 1102 illustrates detecting at least one physical impairment associated with the at least one individual. For example, as shown in FIGS. 4 through 8, impairment detector module 614 can detect at least one physical impairment associated with the at least one individual. In one instance, impairment detector module 614 detects a physical impairment including a bodily impairment associated with an individual from the individual via a user interface. A physical impairment may include a condition or function judged to be significantly impaired relative to the usual standard of an individual of their group and may include physical impairment, sensory impairment, and/or disease. In some instances, impairment detector module 614 may include a computer processor.

Further, operation 1104 illustrates detecting at least one of a disease, an illness, or a bodily impairment. For example, as shown in FIGS. 4 through 8, bodily impairment detector module 616 can detect at least one of a disease, an illness, or a bodily impairment. In one example, bodily impairment detector module 616 may detect an indication of a disease and a bodily impairment from a database entry. A disease may include an abnormal condition of an organism that impairs bodily functions associated with one or more specific symptoms and signs and may include discomfort, distress, dysfunction, injury, a disorder, a syndrome, infection, and/or other atypical variation associated with structure and/or function of the body. An illness may include any state of poor health. Some examples of an illness may include cancer, the common cold, influenza, pneumonia, and/or high cholesterol. A bodily impairment may include a diminished ability in body function and/or structure. In some instances, bodily impairment detector module 616 may include a computer processor.

Further, operation 1106 illustrates detecting an impairment associated with at least one individual including at least one of a potential medication reaction or a potential susceptibility to a side effect. For example, as shown in FIGS. 4 through 8, specific impairment detector module 618 can detect an impairment associated with at least one individual including at least one of a potential medication reaction or a potential susceptibility to a side effect. In one example, specific impairment detector module 618 may detect from a network storage location an impairment associated with an individual including a potential medication reaction and a potential susceptibility to a side effect. A potential medication reaction may include a possible response a person may exhibit resulting from at least one drug and/or medication administered to the person. A potential medication reaction may include an allergy and/or a drug and/or medication interaction with a separate drug and/or medication. A potential susceptibility to a side effect may include the probability a certain person may be vulnerable to a side effect coupled with a specific drug and/or medication. Accepting an impairment may further assist in presenting an appropriate therapy for the individual by, for example, not presenting a therapy that may invoke and/or trigger an undesired side effect and/or reaction. In some instances, specific impairment detector module 618 may include a computer processor.

Figure 12:
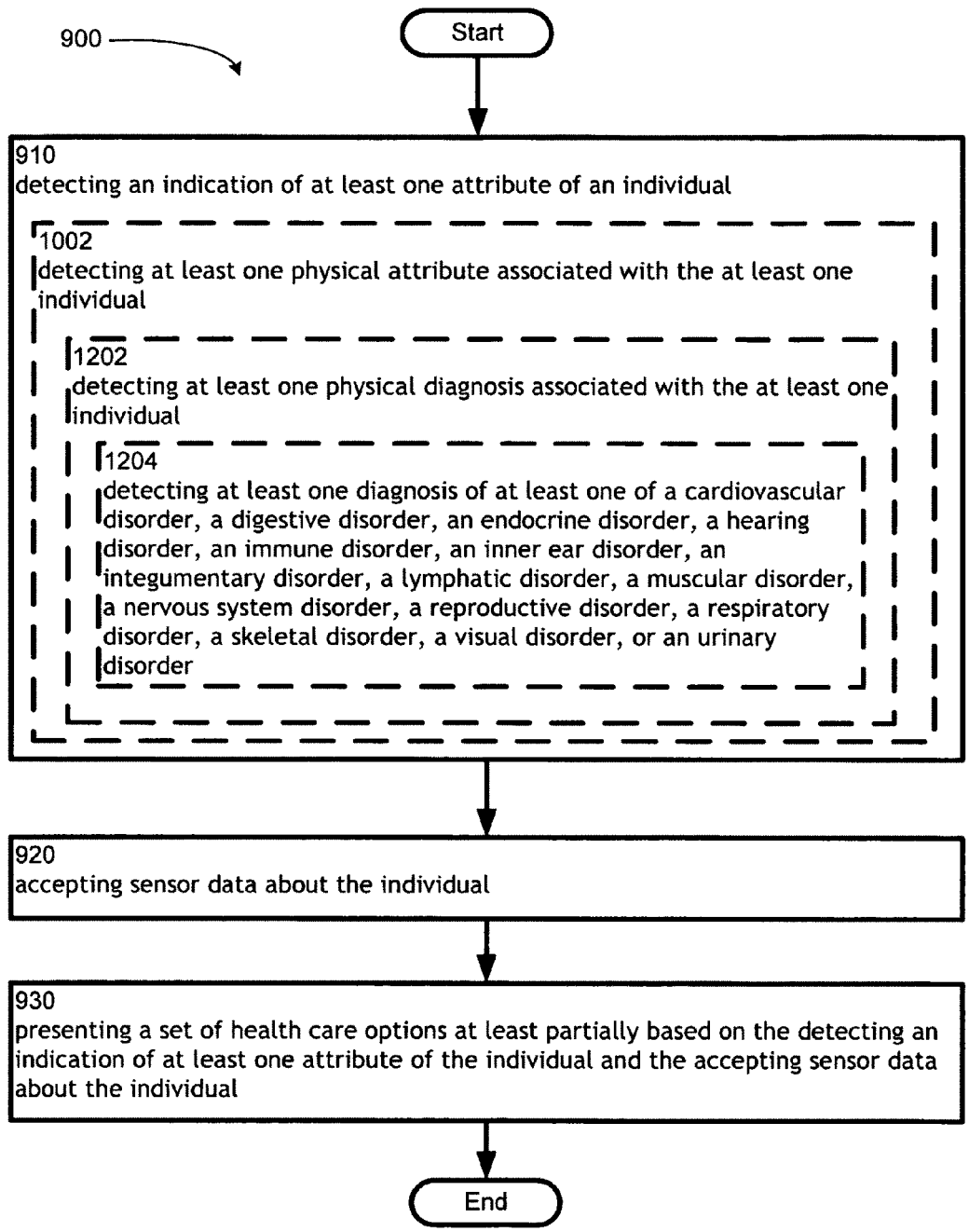
FIG. 12 illustrates an alternative embodiment of the operational flow of FIG. 9.

FIG. 12 illustrates alternative embodiments of the example operational flow 800 of FIG. 8. FIG. 12 illustrates example embodiments where operation 910 may include at least one additional operation. Additional operations may include operation 1202 and/or operation 1204.

Further, operation 1202 illustrates detecting at least one physical diagnosis associated with the at least one individual. For example, as shown in FIGS. 4 through 8, diagnosis detector module 620 can detect at least one physical diagnosis associated with the at least one individual. In a specific example, diagnosis detector module 620 may detect from a memory device a physical diagnosis of epilepsy associated with the individual. A physical diagnosis may include identifying a disease and/or condition by its outward signs and/or symptoms. Some other examples of a physical diagnosis may include identifying influenza and/or identifying Alzheimer's disease. In some instances, diagnosis detector module 620 may include a computer processor.

Further, operation 1204 illustrates detecting at least one diagnosis of at least one of a cardiovascular disorder, a digestive disorder, an endocrine disorder, a hearing disorder, an immune disorder, an inner ear disorder, an integumentary disorder, a lymphatic disorder, a muscular disorder, a nervous system disorder, a reproductive disorder, a respiratory disorder, a skeletal disorder, a visual disorder, or an urinary disorder. For example, as shown in FIGS. 4 through 8, disorder detector module 622 can detect at least one diagnosis of at least one of a cardiovascular disorder, a digestive disorder, an endocrine disorder, a hearing disorder, an immune disorder, an inner ear disorder, an integumentary disorder, a lymphatic disorder, a muscular disorder, a nervous system disorder, a reproductive disorder, a respiratory disorder, a skeletal disorder, a visual disorder, or an urinary disorder. In a specific instance, disorder detector module 622 can detect from a user interface a diagnosis of a respiratory disorder. A cardiovascular disorder may include a disorder associated with the circulatory system including the pumping and channeling of blood to and from the body and lungs with the heart, the blood, and the blood vessels. Examples of a circulatory disorder include high blood pressure, coronary heart disease, atherosclerosis, or the like. A digestive disorder may include a disorder associated with the esophagus, the stomach, the liver, the gallbladder, the pancreas, the intestines, the rectum, the anus, and/or the digestive system including digestion and processing food with salivary glands. Examples of a digestive disorder include GERD, Crohn's disease, IBS, or the like. An endocrine disorder may include a disorder associated with the endocrine system including the pancreas, the pituitary gland, the pineal body and/or the pineal gland, the thyroid, the parathyroids, the adrenal glands, and/or communication within the body using hormones made by the endocrine glands, such as the hypothalamus. Examples of an endocrine disorder include diabetes, acromegaly, or the like. A hearing disorder may include a full or partial decrease in the ability to detect or understand sounds. Some examples of a hearing disorder may include otosclerosis, deafness, and/or unilateral hearing toss. An immune disorder may include a dysfunction of the immune system. Examples of an immune disorder may include an immunodeficiency, such as malfunctioning lymphocytes; autoimmunity, such as Coeliac disease and/or autoimmune hepatitis; and/or hypersensitivity, such as asthma. An inner ear disorder may include a balance disorder, such as vertigo, disequilibrium, and/or pre-syncope. An integumentary disorder may include a disorder associated with the integumentary system including the skin, hair, and/or nails, such as psoriasis, eczema, dermatitis, or the like. A lymphatic disorder may include a disorder associated with the lymphatic system including structures involved in the transfer of lymph between tissues and the blood stream and/or the lymph and the nodes and vessels that transport lymph including the immune system, including defending against disease-causing agents with leukocytes, and/or including the tonsils, the adenoids, the thymus, and/or the spleen. Examples of a lymphatic disorder include lymphedema, lymphadenopathy, or the like. A muscle disorder may include a disorder associated with the muscular system including the structure and/or movement of muscles. Examples of a muscle disorder include muscular dystrophy, myasthenia gravis, an injury, such as a strain, or the like. A nervous system disorder may include a disorder associated with the nervous system including collecting, transferring, and/or processing information with the brain, the spinal cord, the peripheral nerves, and/or the nerves. Examples of a nervous system disorder include multiple sclerosis, fibromyalgia, carpal tunnel syndrome, or the like. A reproductive disorder may include a disorder associated with the reproductive system including the sex organs, such as ovaries, fallopian tubes, the uterus, the vagina, mammary glands, testes, the vas deferens, seminal vesicles, the prostate, and/or the penis. Examples of a reproductive disorder include erectile dysfunction, endometriosis, fibroids, or the like. A respiratory disorder may include a disorder associated with the respiratory system including the organs used for breathing, the pharynx, the larynx, the trachea, the bronchi, the lungs, and/or the diaphragm. Examples of a respiratory disorder include emphysema, asthma, or the like. A skeletal disorder may include a disorder associated with the skeletal system including the structural support and protection with bones, cartilage, ligaments, and/or tendons. Examples of a skeletal disorder include osteoporosis, arthritis, tendonitis, a skeletal injury, such as a bone fracture, or the like. A visual disorder may include a disease, impairment, and/or lack of function in the eye and/or in visual perception. Some examples of a visual disorder may include amblyopia, macular degeneration, glaucoma, and/or blindness. A urinary disorder may include a disorder associated with the urinary system including the kidneys, the ureters, the bladder and/or urethra involved in fluid balance, electrolyte balance and/or the excretion of urine. Examples of a urinary disorder include bladder dysfunction, kidney disease, bladder or urethra infection, or the like. In some instances, disorder detector module 622 may include a computer processor.

Figure 13:
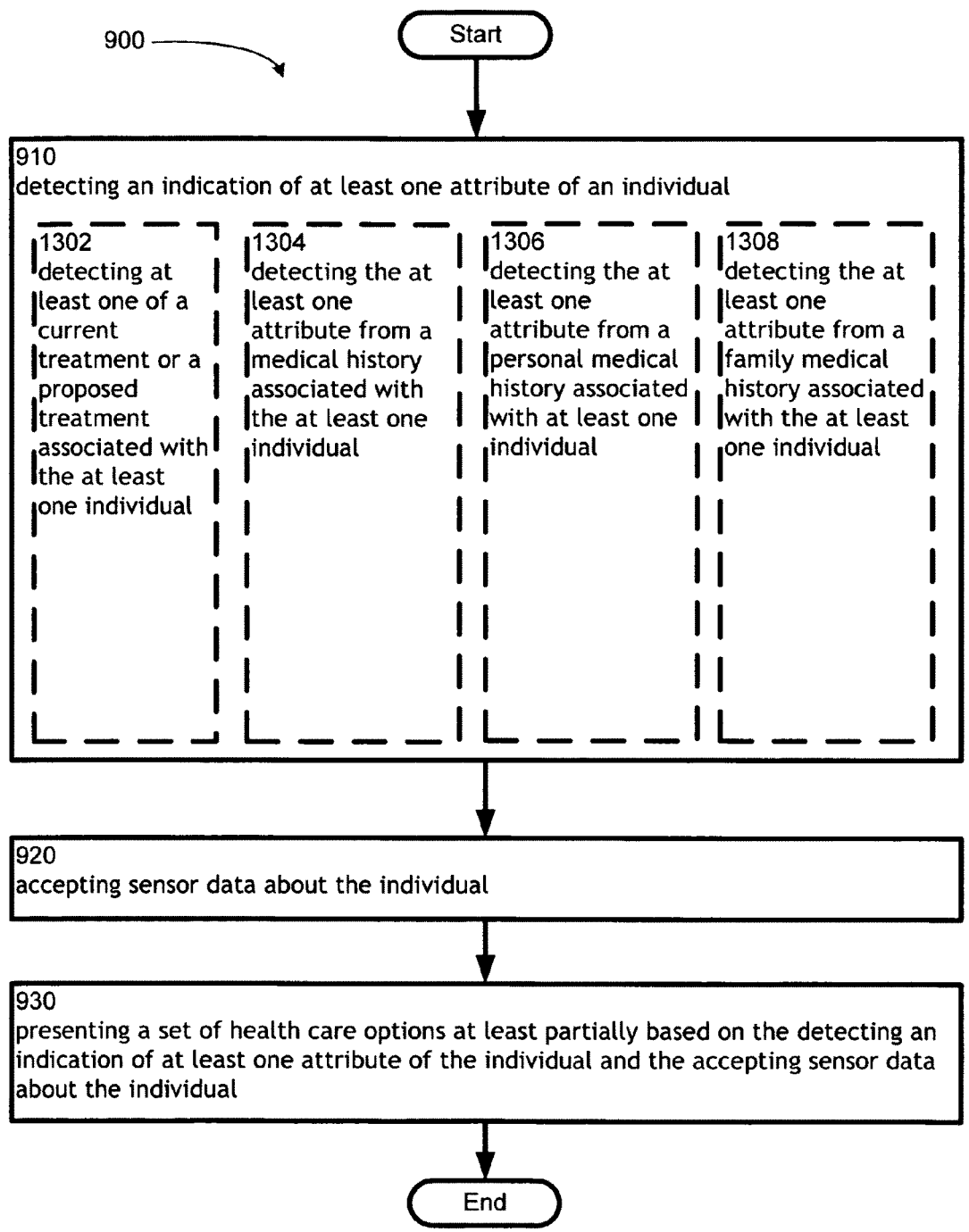
FIG. 13 illustrates an alternative embodiment of the operational flow of FIG. 9.

FIG. 13 illustrates alternative embodiments of the example operational flow 800 of FIG. 8. FIG. 13 illustrates example embodiments where operation 910 may include at least one additional operation. Additional operations may include operation 1302, operation 1304, operation 1306, and/or operation 1308.

Operation 1302 illustrates detecting at least one of a current treatment or a proposed treatment associated with the at least one individual. For example, as shown in FIGS. 4 through 8, treatment detector module 624 can detect at least one of a current treatment or a proposed treatment associated with the at least one individual. In one instance, treatment detector module 624 may detect a current treatment regime associated with a certain individual. A current treatment may include one or a series of treatments recommended, administered, and/or prescribed for a certain individual. A proposed treatment may include one or a series of treatments recommended, prescribed, and/or not currently administered to a certain individual. In some instances, treatment detector module 624 may include a computer processor.

Operation 1304 illustrates detecting the at least one attribute from a medical history associated with the at least one individual. For example, as shown in FIGS. 4 through 8, medical history detector module 626 can detect the at least one attribute from a medical history associated with the at least one individual. In one example, medical history detector module 626 may detect an attribute from a medical history including a record of diabetes therapy associated with a specific individual. A medical history may include a list of previous illnesses, symptoms, medicines, treatments, health risk factors, operations, and/or doctor visits for an individual and/or a relation of an individual. In some instances, medical history detector module 626 may include a computer processor.

Operation 1306 illustrates detecting the at least one attribute from a personal medical history associated with at least one individual. For example, as shown in FIGS. 4 through 8, personal history detector module 628 can detect the at least one attribute from a personal medical history associated with at least one individual. In an embodiment, personal history detector module 628 may detect an attribute including, for example, a list of surgeries from a personal medical history associated with a specific individual. A personal medical history may include a list of previous illnesses, symptoms, medicines, treatments, health risk factors, operations, and/or doctor visits associated with at least one individual. A personal and/or a family medical history may include life history and/or social history characteristics such as smoking, drinking, drug use, sexual history, exercise history, eating history, nutraceutical history, or the like. In some instances, personal history detector module 628 may include a computer processor.

Operation 1308 illustrates detecting the at least one attribute from a family medical history associated with the at least one individual. For example, as shown in FIGS. 4 through 8, family history detector module 630 can detect the at least one attribute from a family medical history associated with the at least one individual. In an example, family history detector module 630 may detect an attribute including a list of family members that have had epilepsy from a family medical history associated with a specific individual. A family medical history may include a list of previous illnesses, symptoms, medicines, treatments, health risk factors, operations, and/or doctor visits associated with family members related to the at least one individual. In some instances, family history detector module 630 may include a computer processor.

Figure 14:
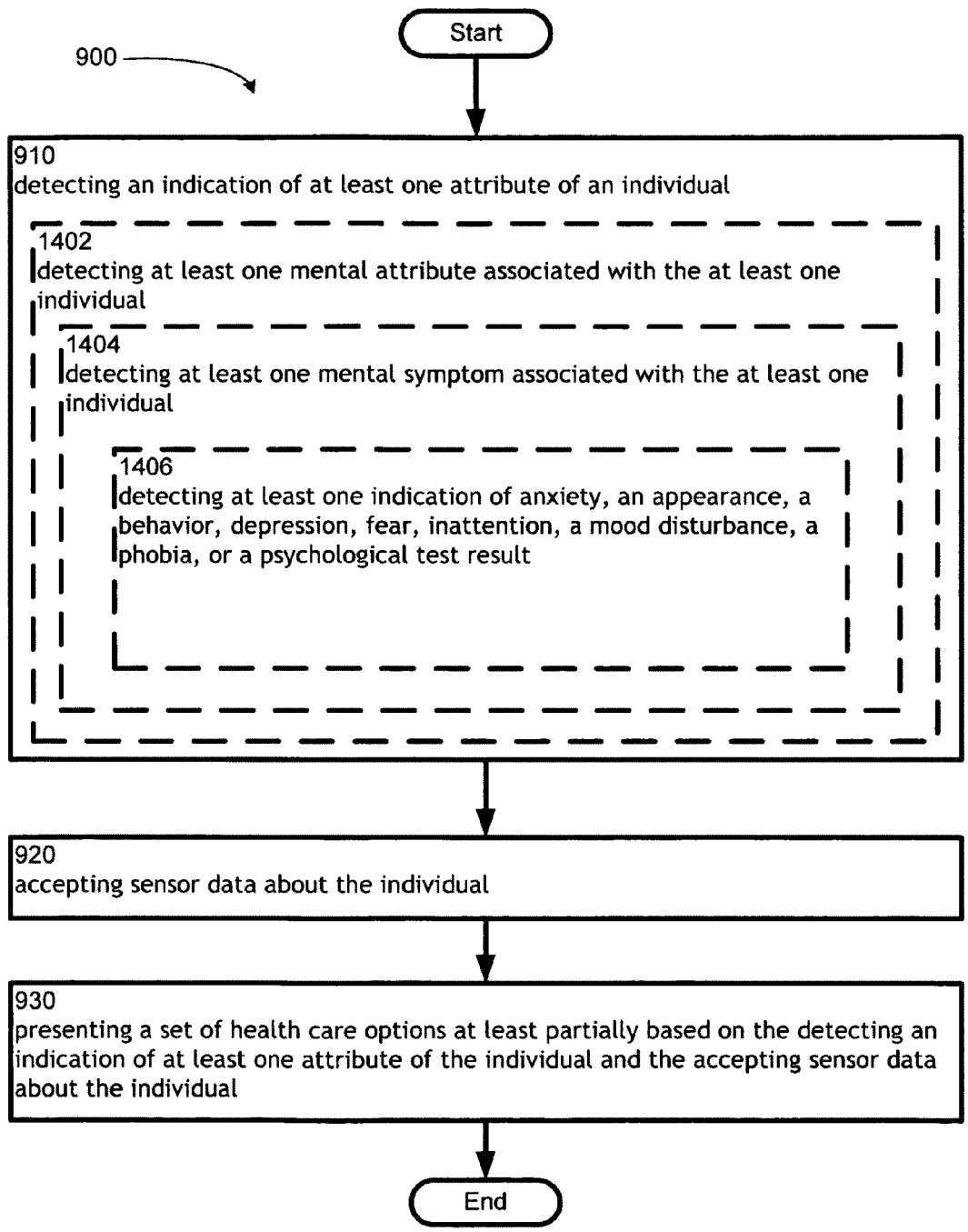
FIG. 14 illustrates an alternative embodiment of the operational flow of FIG. 9.

FIG. 14 illustrates alternative embodiments of the example operational flow 800 of FIG. 8. FIG. 14 illustrates example embodiments where operation 910 may include at least one additional operation. Additional operations may include operation 1402, operation 1404, operation 1406, and/or operation 1408.

Operation 1402 illustrates detecting at least one mental attribute associated with the at least one individual. For example, as shown in FIGS. 4 through 8, mental attribute detector module 632 can detect at least one mental attribute associated with the at least one individual. In one example, mental attribute detector module 632 may detect a mental attribute including, for example, an indication of a learning disability associated with a specific individual. A mental attribute may include an attribute that may be related to and/or associated with basic mental function and/or high-level brain function. Some examples of a mental attribute may include an indication of cognitive disability, measurements of brain activity, for example using functional MRI or near infra-red technology, and/or measurements of mental development. In some instances, mental attribute detector module 632 may include a computer processor.

Further, operation 1404 illustrates detecting at least one mental symptom associated with the at least one individual. For example, as shown in FIGS. 4 through 8, mental symptom detector module 634 can detect at least one mental symptom associated with the at least one individual. In one example, mental symptom detector module 634 may detect a mental symptom including a stress level measurement associated with a specific individual. A mental symptom may include a manifestation, sign, and/or an indication of the presence of a disease and/or some other mental disorder and/or abnormality. Some examples of a mental symptom may include lack of attention, indication of stress, hyperactivity, nervousness, and/or lack of responsiveness. In some instances, mental symptom detector module 634 may include a computer processor.

Further, operation 1406 illustrates detecting at least one indication of anxiety, an appearance, a behavior, depression, fear, inattention, a mood disturbance, a phobia, or a psychological test result. For example, as shown in FIGS. 4 through 8, mental indication detector module 636 can detect at least one indication of anxiety, an appearance, a behavior, depression, fear, inattention, a mood disturbance, a phobia, or a psychological test result. In one example, mental indication detector module 636 can detect from a user interface an indication of anxiety and depression. Anxiety may include feelings of fear, apprehension, and/or worry and may be accompanied by physical sensations. An appearance may include an outward, audible, and/or visible aspect of a person and/or thing associated with a person. A behavior may include the manner in which a person and/or thing associated with a person acts and/or reacts. Depression may include a mental state characterized by pessimism, a sense of inadequacy, despondence, despair, a low level of energy, and/or a lack of activity. Fear may be caused by impending danger, perceived evil, and/or pain, whether real or imagined. Inattention may include the failure of a person to focus attention. A mood disturbance may include a change in emotional state. A phobia may include an irrational, and/or persistent fear of certain situations, objects, activities, and/or people. A psychological test result may include a sample behavior for inferring a certain generalization about a person. For example, a personality test result may indicate that person has obsessive/compulsive characteristics. In some instances, mental indication detector module 636 may include a computer processor.

Figure 15:
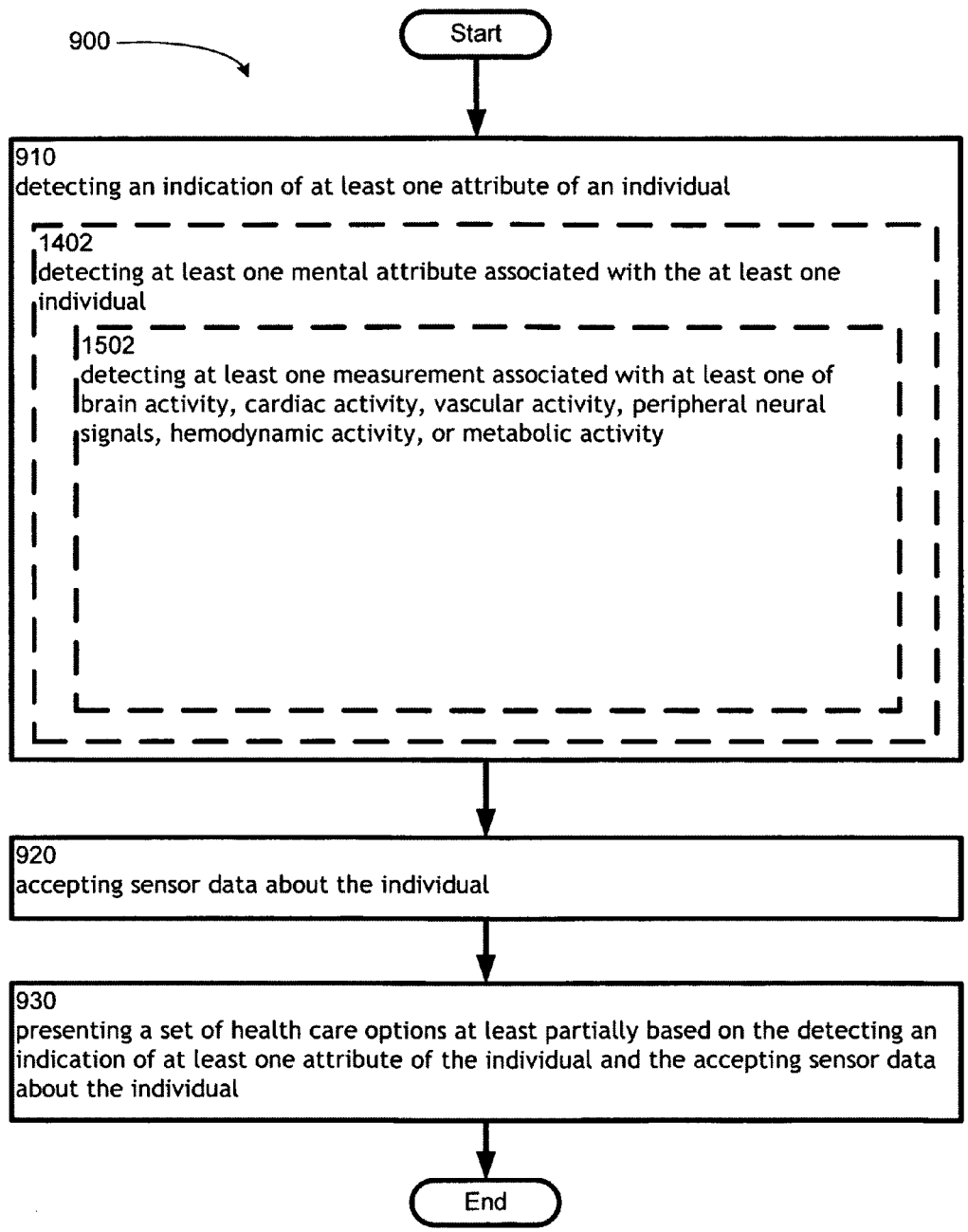
FIG. 15 illustrates an alternative embodiment of the operational flow of FIG. 9.

FIG. 15 illustrates alternative embodiments of the example operational flow 800 of FIG. 8. FIG. 15 illustrates example embodiments where operation 910 may include at least one additional operation. Additional operations may include operation 1502.

Further, operation 1502 illustrates detecting at least one measurement associated with at least one of brain activity, cardiac activity, vascular activity, peripheral neural signals, hemodynamic activity, or metabolic activity. For example, as shown in FIGS. 4 through 8, mental activity detector module 638 may detect at least one measurement associated with at least one of brain activity, cardiac activity, vascular activity, peripheral neural signals, hemodynamic activity, or metabolic activity. In one instance, mental activity detector module 638 can detect a measurement associated with brain activity. Brain activity may include the electrical activity of the brain, such as that measured by EEG, MEG, or the like. Other brain activity measurements may include functional MRI imaging, near infra-red imaging, PET scanning, or the like. Cardiac activity may include electrical activity in the heart, such as that measured by EKG or visual imaging. Vascular activity may include any activity and/or function of the circulatory system. Peripheral neural signals may include neural signals sent through the peripheral nervous system. Hemodynamic activity may include any activity associated with the circulatory system. Metabolic activity may include any activity associated with the biochemical reactions occurring in a living organism. In some instances, mental activity detector module 638 may include a computer processor.

Figure 16:
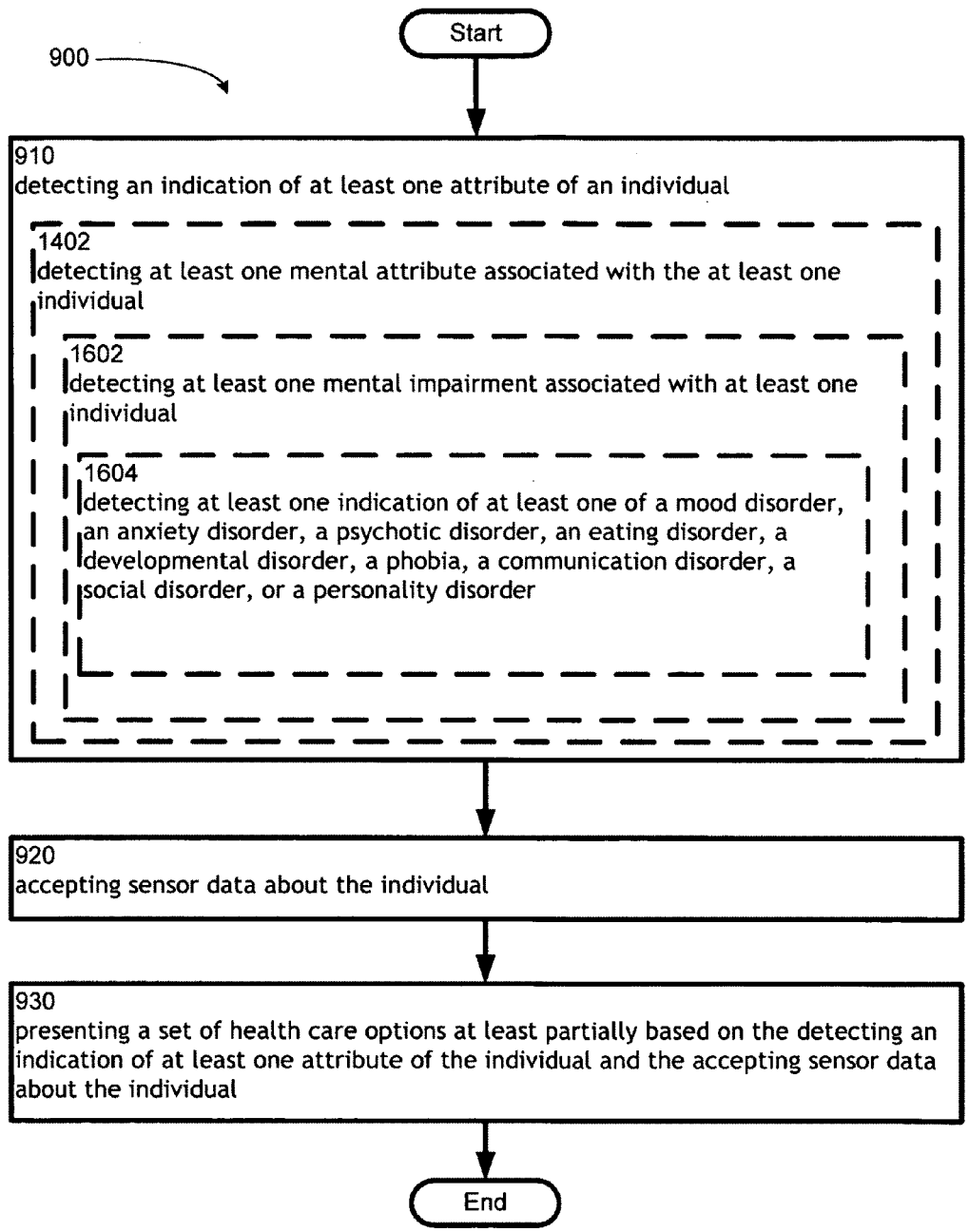
FIG. 16 illustrates an alternative embodiment of the operational flow of FIG. 9.

FIG. 16 illustrates alternative embodiments of the example operational flow 800 of FIG. 8. FIG. 16 illustrates example embodiments where operation 910 may include at least one additional operation. Additional operations may include operation 1602 and/or operation 1604.

Further, operation 1602 illustrates detecting at least one mental impairment associated with at least one individual. For example, as shown in FIGS. 4 through 8, mental impairment detector module 640 can detect at least one mental impairment associated with at least one individual. In one example, mental impairment detector module 640 can detect a mental impairment associated with a specific individual. A mental impairment may include a condition or function judged by a health care provider to be significantly impaired relative to the usual standard of an individual of their group, and may include mental impairment, sensory impairment, and/or mental disease. In some instances, mental impairment detector module 640 may include a computer processor.

Further, operation 1604 illustrates detecting at least one indication of at least one of a mood disorder, an anxiety disorder, a psychotic disorder, an eating disorder, a developmental disorder, a phobia, a communication disorder, a social disorder, or a personality disorder. For example, as shown in FIGS. 4 through 8, mental disorder detector module 642 may detect at least one indication of at least one of a mood disorder, an anxiety disorder, a psychotic disorder, an eating disorder, a developmental disorder, a phobia, a communication disorder, a social disorder, or a personality disorder. In one instance, mental disorder detector module 642 can detect from a user interface an indication of a mood disorder in a specific individual. A mood disorder may include a condition whereby the prevailing emotional mood is distorted or inappropriate to the circumstances, and may include examples such as bipolar disorder, an alteration in mood, and/or depression. An anxiety disorder may include nervous system disorders such as irrationality, illogical worry not based on fact, fear, and/or phobia. A psychotic disorder may include a state of mind in which thinking becomes irrational and/or disturbed and may include hallucinations, abnormal perception, mania, dementia, delusions and/or delusional beliefs, delirium, depression, psychosis personality disorder, personality changes, and/or disorganized thinking. An eating disorder may include a compulsion to eat and/or avoid eating that negatively affects physical and/or mental health. Some examples of an eating disorder may include anorexia nervosa and bulimia nervosa. A developmental disorder may include a disorder occurring in a child's development, which may retard development. Some examples of a developmental disorder may include an emotional disorder, a cognitive disorder, and/or a mental disorder accompanied by physical traits, such as Down syndrome. A phobia may include an irrational, intense, and/or persistent fear of certain situations, objects, activities, and/or persons. Examples of phobias include social phobias, arachnophobia, xenophobia, and/or claustrophobia. A communication disorder may include a disease and/or a condition partially or totally preventing human communication. Some examples of a communication disorder may include autism, stuttering, and/or aphasia. A social disorder may include a condition characterized by a difficulty in human interaction and/or emotional discomfort in social situations. Some examples of a social disorder may include stage fright, social anxiety disorder, and/or shyness. A personality disorder may include a disorder characterized by pathological trends in personality structure. Some examples of a personality disorder may include a paranoid personality disorder, a narcissistic personality disorder, and/or an obsessive-compulsive personality disorder. In some instances, mental disorder detector module 642 may include a computer processor.

Figure 17:
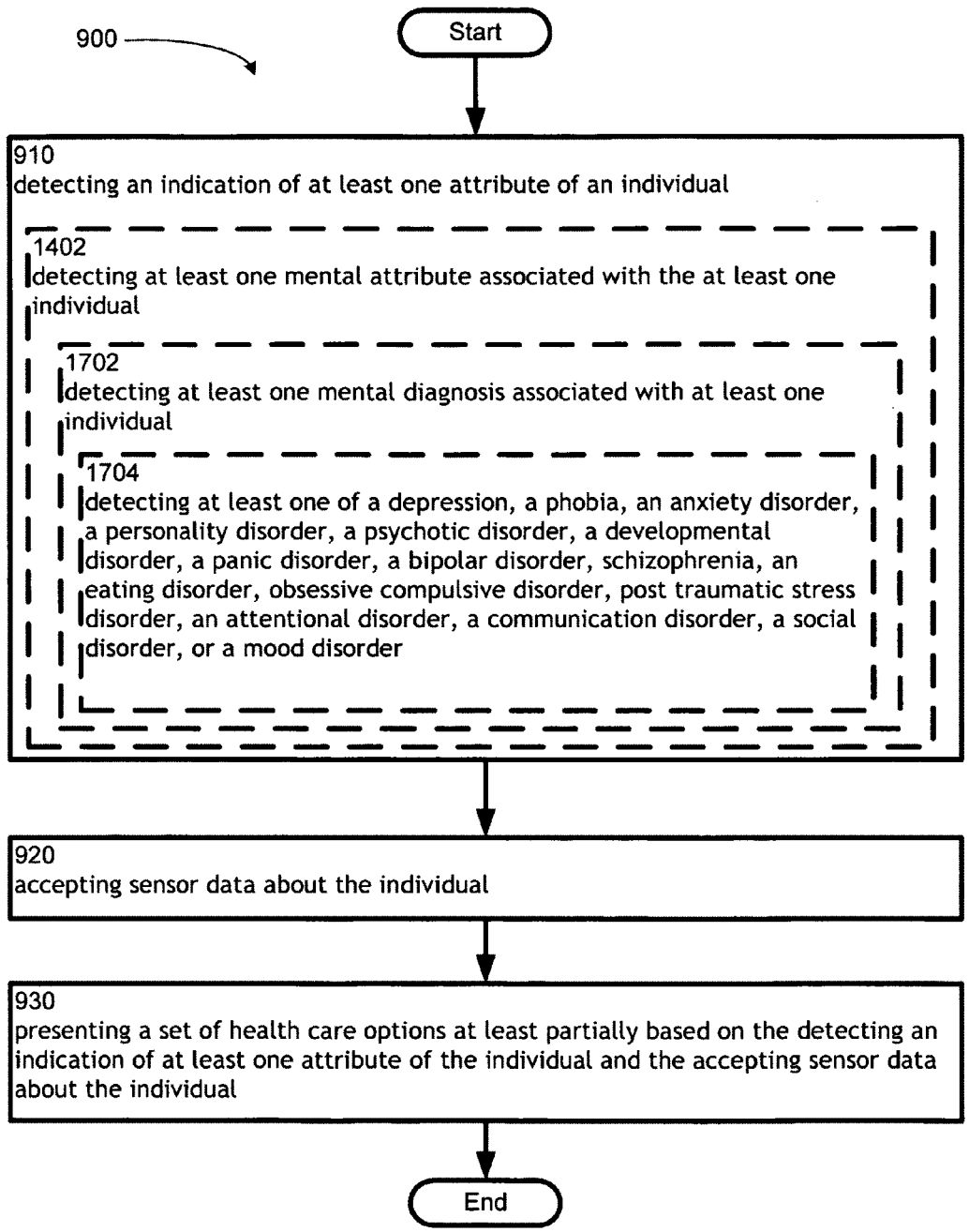
FIG. 17 illustrates an alternative embodiment of the operational flow of FIG. 9.

FIG. 17 illustrates alternative embodiments of the example operational flow 800 of FIG. 8. FIG. 17 illustrates example embodiments where operation 910 may include at least one additional operation. Additional operations may include operation 1702 and/or operation 1704.

Further, operation 1702 illustrates detecting at least one mental diagnosis associated with at least one individual. For example, as shown in FIGS. 4 through 8, mental diagnosis detector module 644 can detect at least one mental diagnosis associated with at least one individual. In a specific instance, mental diagnosis detector module 644 may detect a mental diagnosis including a phobia associated with a specific individual. A mental diagnosis may include identifying a mental disorder and/or condition by its symptoms. Some examples of a mental diagnosis may include a mood disorder such as depression, an anxiety disorder such as PTSD, a behavioral disorder such as ADHD, a personality disorder such as borderline personality disorder, and/or a phobia. Mental disorders may include those listed in the Diagnostic and Statistical Manual of Mental Disorders (DSM). In some instances, mental diagnosis detector module 644 may include a computer processor.

Further, operation 1704 illustrates detecting at least one of a depression, a phobia, an anxiety disorder, a personality disorder, a psychotic disorder, a developmental disorder, a panic disorder, a bipolar disorder, schizophrenia, an eating disorder, obsessive compulsive disorder, post traumatic stress disorder, an attentional disorder, a communication disorder, a social disorder, or a mood disorder. For example, as shown in FIGS. 4 through 8, mental disorder detector module 646 can detect at least one of a depression, a phobia, an anxiety disorder, a personality disorder, a psychotic disorder, a developmental disorder, a panic disorder, a bipolar disorder, schizophrenia, an eating disorder, obsessive compulsive disorder, post traumatic stress disorder, an attentional disorder, a communication disorder, a social disorder, or a mood disorder. In one example, mental disorder detector module 646 may detect a diagnosis of depression. Depression may include a mental state characterized by a pessimistic sense of inadequacy and/or a despondent lack of activity. A phobia may include an irrational, intense, and/or persistent fear of certain situations, objects, activities, and/or persons. Some phobias may include social phobias, arachnophobia, xenophobia, and/or claustrophobia. An anxiety disorder may include nervous system disorders such as irrationality, illogical worry not based on fact, fears, and/or phobias. A personality disorder may include a disorder characterized by pathological trends in personality structure. Some examples of a personality disorder may include a paranoid personality disorder, a narcissistic personality disorder, and/or an obsessive-compulsive personality disorder. A psychotic disorder may include a state of mind in which thinking becomes irrational and/or disturbed and may include hallucinations, delusional beliefs, personality changes, and/or disorganized thinking. A developmental disorder may include a disorder occurring in a child's development, which may often retard development. Some examples of a developmental disorder may include psychological or physical disorders. A panic disorder may include a condition characterized by recurring panic attacks in combination with significant behavioral change. A bipolar disorder may include a mood disorder characterized by the presence of one or more episodes of abnormally elevated mood, such as Bipolar I disorder, Bipolar II disorder, cyclothymia, and/or Bipolar-NOS. Schizophrenia may include a mental illness characterized by impairments in the perception or expression of reality, most commonly manifesting as auditory hallucinations, paranoid or bizarre delusions or disorganized speech and thinking in the context of significant social or occupational dysfunction. An eating disorder may include a compulsion to eat or avoid eating, such as anorexia nervosa and/or bulimia nervosa. Obsessive compulsive disorder may include a psychiatric anxiety disorder characterized by obsessive, distressing, intrusive thoughts and related compulsions which attempt to neutralize the obsessions. Post traumatic stress disorder may include an anxiety disorder that can develop after exposure to one or more terrifying events in which grave physical harm occurred or was threatened. An attentional disorder may include a persistent pattern of inattention and/or hyperactivity, as well as forgetfulness, poor impulse control or impulsivity, and distractibility, such as attention-deficit hyperactivity disorder (ADHD). A communication disorder may include a disease and/or a condition partially or totally preventing human communication. Some examples of a communication disorder may include autism, stuttering, and/or aphasia. A social disorder may include a condition characterized by a difficulty in human interaction and/or emotional discomfort in social situations. Some examples of a social disorder may include stage fright, social anxiety disorder, and/or shyness. A mood disorder may include a condition whereby the prevailing emotional mood is distorted or inappropriate to the circumstances and may include examples such as bipolar disorder and/or depression. In some instances, mental disorder detector module 646 may include a computer processor.

Figure 18:
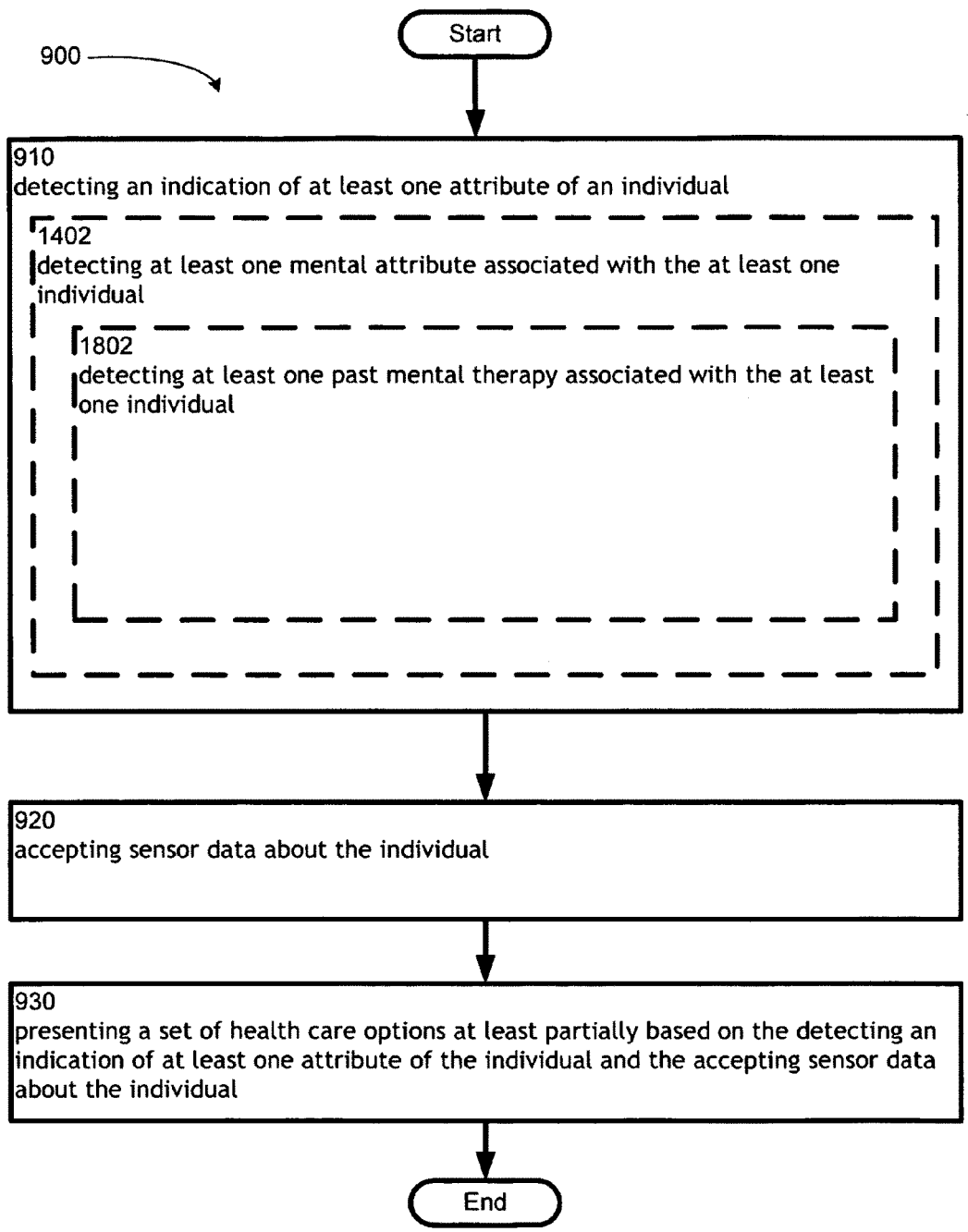
FIG. 18 illustrates an alternative embodiment of the operational flow of FIG. 9.

FIG. 18 illustrates alternative embodiments of the example operational flow 800 of FIG. 8. FIG. 18 illustrates example embodiments where operation 910 may include at least one additional operation. Additional operations may include operation 1802.

Further, operation 1802 illustrates detecting at least one past mental therapy associated with the at least one individual. For example, as shown in FIGS. 4 through 8, mental therapy detector module 648 can detect at least one past mental therapy associated with the at least one individual. In one instance, mental therapy detector module 648 can detect an indication of a past mental therapy associated with a specific individual. A past mental therapy may include a list and/or a record of at least one mental therapy, such as an anti-depressant medication, administered to at least one individual. In some instances, mental therapy detector module 648 may include a computer processor.

Figure 19:
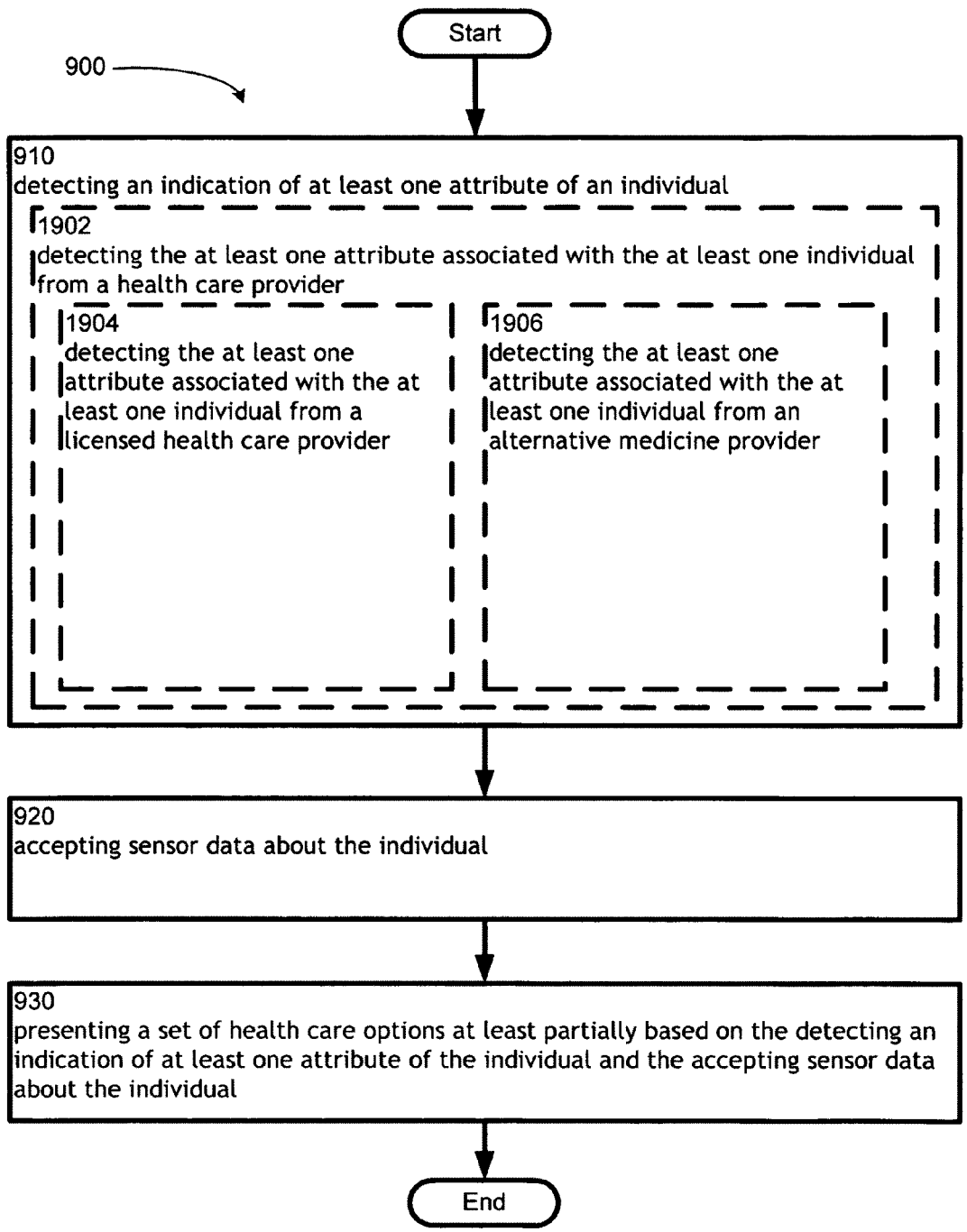
FIG. 19 illustrates an alternative embodiment of the operational flow of FIG. 9.

FIG. 19 illustrates alternative embodiments of the example operational flow 800 of FIG. 8. FIG. 19 illustrates example embodiments where operation 910 may include at least one additional operation. Additional operations may include operation 1902, operation 1904, and/or operation 1906.

Operation 1902 illustrates detecting the at least one attribute associated with the at least one individual from a health care provider. For example, as shown in FIGS. 4 through 8, health care provider detector module 650 can detect the at least one attribute associated with the at least one individual from a health care provider. In one example, health care provider detector module 650 can detect from a health care provider an attribute associated with a specific individual including a medication history. A health care provider may include a hospital, a doctor, a nurse, a medical clinic, a dentist, and/or any provider of preventive, diagnostic, therapeutic, rehabilitative, maintenance, or palliative care and/or counseling. A healthcare provider may include a seller and/or dispenser of prescription drugs or medical devices. In some instances, health care provider detector module 650 may include a computer processor.

Further, operation 1904 illustrates detecting the at least one attribute associated with the at least one individual from a licensed health care provider. For example, as shown in FIGS. 4 through 8, licensed provider detector module 652 can detect the at least one attribute associated with the at least one individual from a licensed health care provider. In one instance, licensed provider detector module 652 detects an attribute including a symptom indicating a phobia associated with a specific individual from a licensed health care provider. A licensed health care provider may include a person licensed by a governing authority, such as a state, to provide medical and/or health care. Some examples of a licensed health care provider may include a licensed medical doctor or physician, a licensed physician's assistant, and/or a licensed nurse practitioner. In some instances, licensed provider detector module 652 may include a computer processor.

Further, operation 1906 illustrates detecting the at least one attribute associated with the at least one individual from an alternative medicine provider. For example, as shown in FIGS. 4 through 8, alternative medicine provider detector module 654 can detect the at least one attribute associated with the at least one individual from an alternative medicine provider. In one instance, alternative medicine provider detector module 654 may detect a record of bioactive agent administration associated with a specific individual from an alternative medicine provider. An alternative medicine provider may include a provider of folk medicine, herbal medicine, diet fads, homeopathy, faith healing, new age healing, chiropractic, acupuncture, aromatherapy, naturopathy, massage, reflexology, hypnotism, and/or music therapy. In some instances, alternative medicine provider detector module 654 may include a computer processor.

Figure 20:
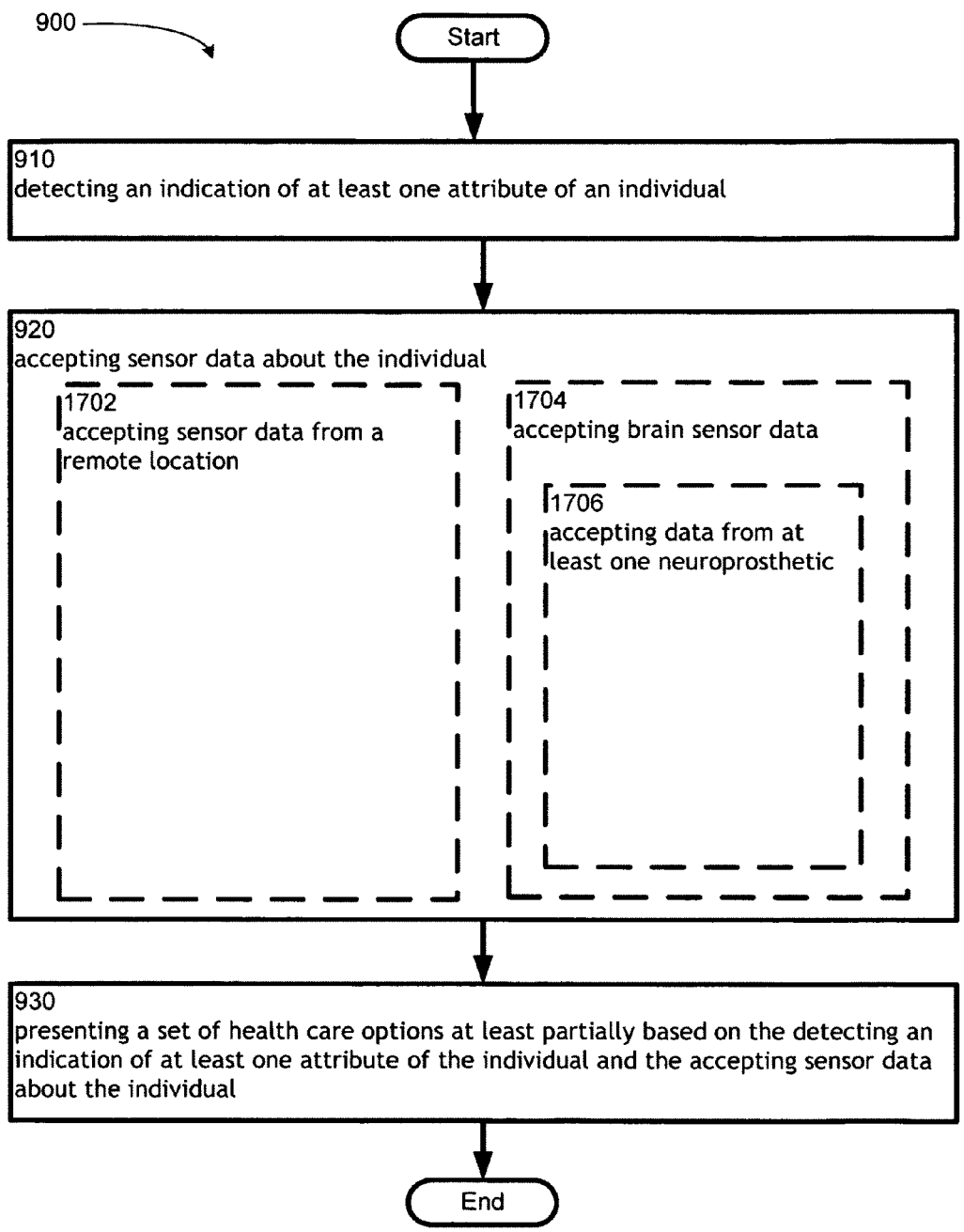
FIG. 20 illustrates an alternative embodiment of the operational flow of FIG. 9.

FIG. 20 illustrates alternative embodiments of the example operational flow 800 of FIG. 8. FIG. 20 illustrates example embodiments where operation 920 may include at least one additional operation. Additional operations may include operation 2002, operation 2004, and/or operation 2006.

Operation 2002 illustrates accepting sensor data from a remote location. For example, as shown in FIGS. 4 through 8, remote data accepter module 656 can detect sensor data from a remote location. For example, remote data accepter module 656 may receive one or more results from at least one sensor from a remote location. In one embodiment, remote data accepter module 656 may receive data from a brain sensor from a remote location, such as from a research hospital in California when the remote data accepter module 656 is located in Massachusetts. In some instances, remote data accepter module 656 may include a computer processor and/or a communication device, for example a network modem and corresponding network circuitry.

Operation 2004 illustrates accepting brain sensor data. For example, as shown in FIGS. 4 through 8, brain sensor data accepter module 658 can accept brain sensor data. In an embodiment, brain sensor data accepter module 658 may accept from a brain sensor electrode array. One example of an electrode array may be found in Flaherty, U.S. Patent Publication No. 2007/0106143, which is incorporated herein by reference. In an embodiment, brain sensor data accepter module 658 may accept data detected by an electrode sensor that senses electrical signals generated by, for example, a patient while imagining movement. In this embodiment, the sensor may generate electrical signals that may be processed and/or accepted by, for example, brain sensor data accepter module 658. Some examples of a brain sensor may include non-invasive sensors, such as electroencephalogram (EEG) sensors, partially invasive sensors, such as electrocorticography sensors, and/or invasive sensors, such as implanted electrodes. A user 140 of a brain sensor may include a patient having a medical condition, an individual experiencing one or more symptoms, an asymptomatic individual, or the like. Brain sensor data may include an indication of physiological impairment, for example for cosmetic enhancement, pregnancy, or improvement in athletic performance. In an embodiment, brain sensor data accepter module 658 may accept brain sensor data from an array of wireless sensors attached to the outside of a user's 140 head. In this embodiment, the array of wireless sensors may wirelessly detect electrical signals in the user's 140 brain and wirelessly relay the information to brain sensor data accepter module 658. The electrical signals produced by the brain may indicate a certain condition of the brain and/or body, such as physical damage, disability, and/or cognitive dysfunction, and may additionally indicate the success of and/or the degree of success of a previously prescribed therapy. In some instances, brain sensor data accepter module 658 may include a computer processor.

Further, operation 2006 illustrates accepting data from at least one neuroprosthetic. For example, as shown in FIGS. 4 through 8, neuroprosthetic accepter module 660 can accept data from at least one neuroprosthetic. A neuroprosthetic may include a device or a series of devices that may function as a substitute for a motor, sensory, and/or cognitive modality that may have been damaged and/or may otherwise not function properly. For example, a neuroprosthetic may include a cochlear implant. A cochlear implant may serve to substitute the functions performed by an ear drum. In an embodiment, neuroprosthetic accepter module 660 may accept data from a cochlear implant. In this embodiment, the data accepted from the cochlear implant may serve to indicate, for example, that the cochlear implant is malfunctioning and a surgery for replacement is needed. In some instances, neuroprosthetic accepter module 660 may include a computer processor.

Figure 21:
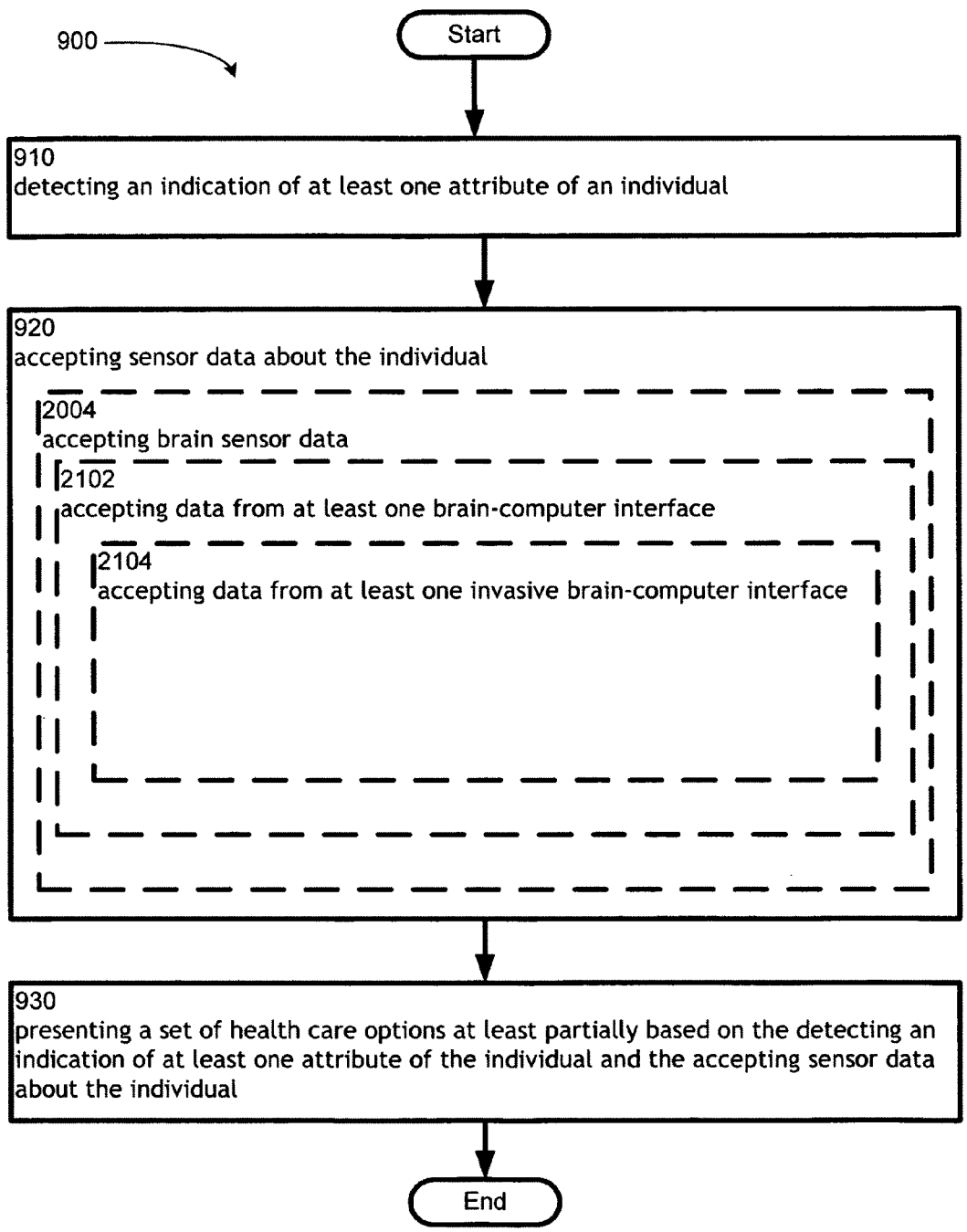
FIG. 21 illustrates an alternative embodiment of the operational flow of FIG. 9.

FIG. 21 illustrates alternative embodiments of the example operational flow 800 of FIG. 8. FIG. 21 illustrates example embodiments where operation 920 may include at least one additional operation. Additional operations may include operation 2102 and/or operation 2104.

Further, operation 2102 illustrates accepting data from at least one brain-computer interface. For example, as shown in FIGS. 4 through 8, brain-computer interface accepter module 662 can accept data from at least one brain-computer interface. A brain-computer interface may include a direct communication pathway between a brain and an external device, such as a neuroprosthetic and/or an array of electrodes. In an embodiment, brain-computer interface accepter module 662 may accept data from an electrocorticography device. Some brain-computer interface devices may be intrusive, partially intrusive, and/or non-intrusive. In some instances, brain-computer interface accepter module 662 may include a computer processor.

Further, operation 2104 illustrates accepting data from at least one invasive brain-computer interface. For example, as shown in FIGS. 4 through 8, invasive accepter module 664 can accept data from at least one invasive brain-computer interface. An invasive brain-computer interface device may include a device implanted directly into the grey matter of the brain during a neurosurgery. In an embodiment, invasive accepter module 664 may accept data from an array of electrodes implanted into a user's 140 visual cortex designed to detect electrical signals and/or the absence of electrical signals and analyzing a user's 140 visual perception. This may serve to assist in diagnosis of, for example, a visual disability. Another example of an invasive brain-computer interface may be found in Boling, U.S. Pat. No. 7,283,856, which is incorporated herein by reference. In some instances, invasive accepter module 664 may include a computer processor.

Figure 22:
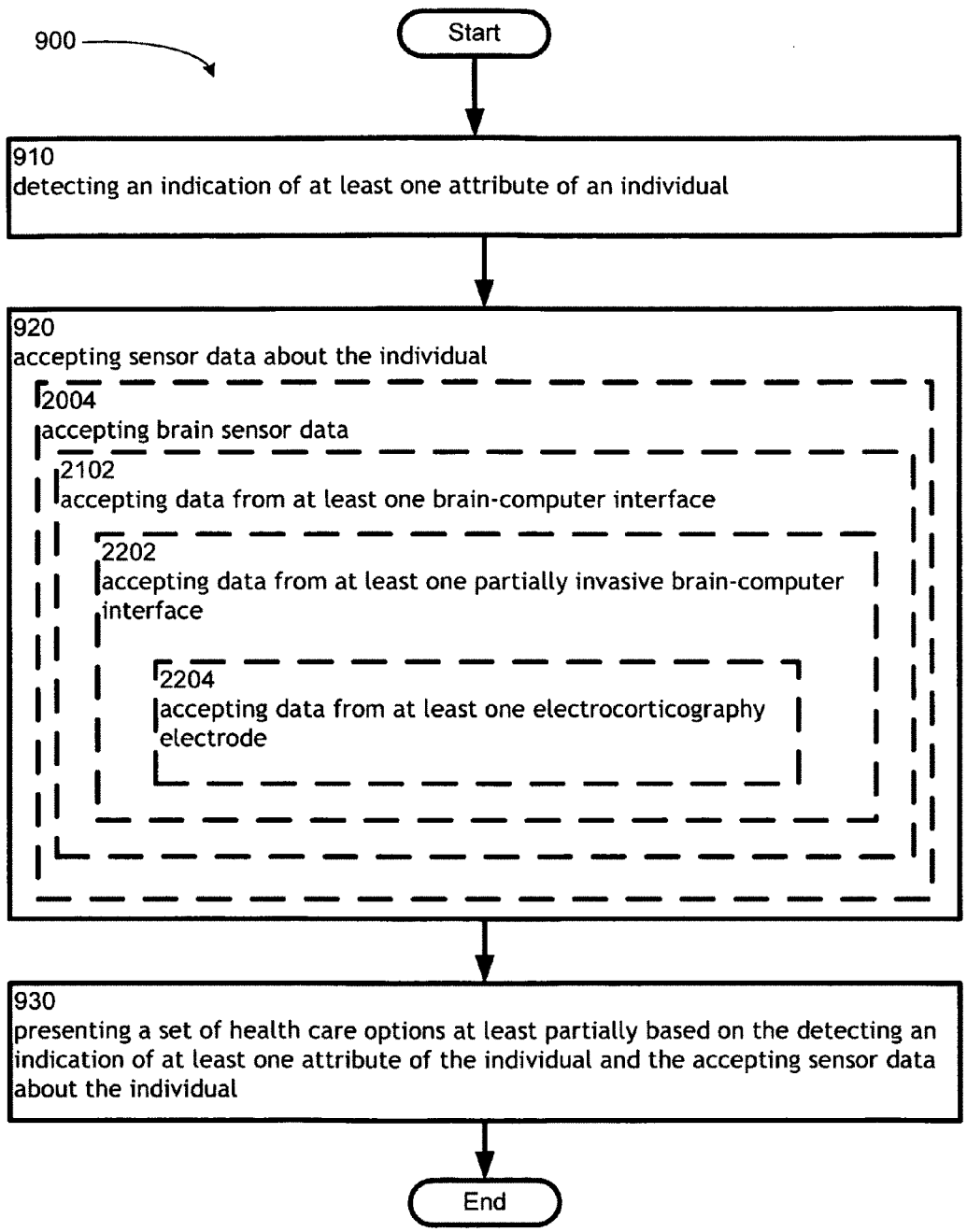
FIG. 22 illustrates an alternative embodiment of the operational flow of FIG. 9.

FIG. 22 illustrates alternative embodiments of the example operational flow 800 of FIG. 8. FIG. 22 illustrates example embodiments where operation 920 may include at least one additional operation. Additional operations may include operation 2202 and/or operation 2204.

Further, operation 2202 illustrates accepting data from at least one partially invasive brain-computer interface. For example, as shown in FIGS. 4 through 8, partially invasive accepter module 666 can accept data from at least one partially invasive brain-computer interface. A partially invasive brain-computer interface may include a device implanted inside a person's skull but outside the brain. Some examples of a partially invasive brain-computer interface may include an electrocorticography device and/or a light reactive imaging device. In an embodiment, partially invasive accepter module 666 may accept data from at least one partially invasive brain-computer interface, such as an electrode implanted between an individual's brain and skull. In some instances, partially invasive accepter module 666 may include a computer processor.

Further, operation 2204 illustrates accepting data from at least one electrocorticography electrode. For example, as shown in FIGS. 4 through 8, electrocorticography accepter module 668 can accept data from at least one electrocorticography electrode. An electrocorticography device may include at least one electrode configured to measure electrical activity of the brain where, for example, the electrodes are embedded in a thin plastic pad that is placed above the cortex and beneath the dura matter. In an embodiment, electrocorticography accepter module 668 may accept data from at least one electrocorticography electrode configured to measure electrical signals in the brain of a patient that suffers from epilepsy. In this example, measuring the electrical signals may assist in determining the timing and/or intensity of an epileptic seizure and may help determine a suitable therapy for the patient. Another example of an electrocorticography device may be found in Leuthardt, U.S. Pat. No. 7,120,486, which is incorporated herein by reference. In some instances, electrocorticography accepter module 668 may include a computer processor and/or accepting circuitry, such as a modem.

Figure 23:
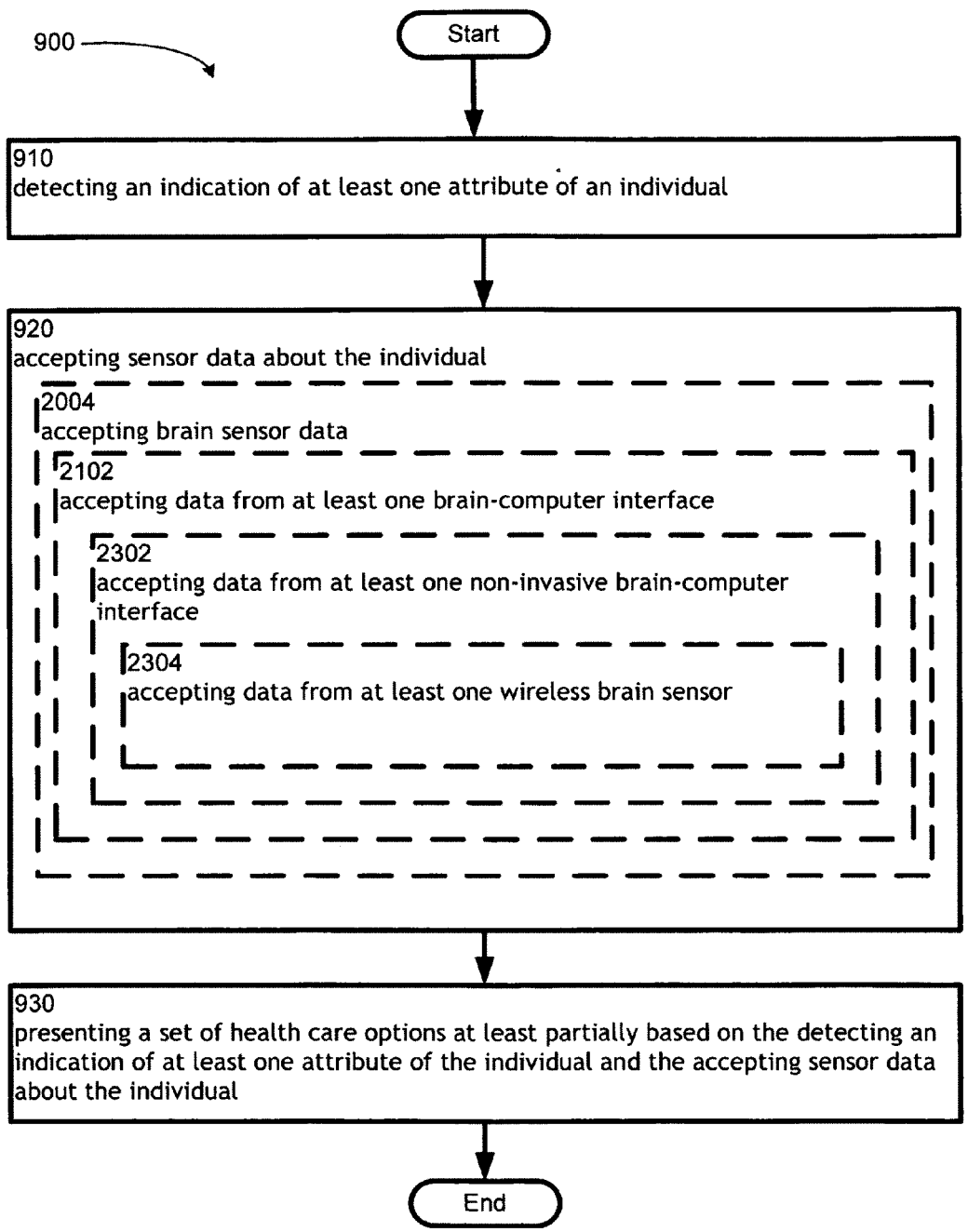
FIG. 23 illustrates an alternative embodiment of the operational flow of FIG. 9.

FIG. 23 illustrates alternative embodiments of the example operational flow 800 of FIG. 8. FIG. 23 illustrates example embodiments where operation 920 may include at least one additional operation. Additional operations may include operation 2302 and/or operation 2304.

Further, operation 2302 illustrates accepting data from at least one non-invasive brain-computer interface. For example, as shown in FIGS. 4 through 8, non-invasive interface accepter module 670 can accept data from at least one non-invasive brain-computer interface. A non-invasive brain-computer interface may include a device that is able to measure signals from the brain without substantially interfering with and/or disturbing body tissue. In one embodiment, non-invasive interface accepter module 670 may accept information from wireless brain sensors that are placed on an individual's head. Another example of a non-invasive brain-computer interface may include an electroencephalography sensor. In some instances, non-invasive interface accepter module 670 may include a computer processor.

Further, operation 2304 illustrates accepting data from at least one wireless brain sensor. For example, as shown in FIGS. 4 through 8, wireless sensor accepter module 672 can accept data from at least one wireless brain sensor. In an embodiment, wireless sensor accepter module 672 may accept data from an array of brain sensors placed on the outside of an individual's head. In this embodiment, the array of brain sensors may detect electromagnetic waves created by neurons. The wireless brain sensor may be wirelessly connected to the wireless sensor accepter module 672. Additional examples of a wireless brain sensor may include Fish, U.S. Pat. No. 6,155,974, and Najafi, et al., U.S. Patent Publication No. 2009/0105557, both of which are incorporated herein by reference. In some instances, wireless sensor accepter module 672 may include a computer processor.

Figure 24:
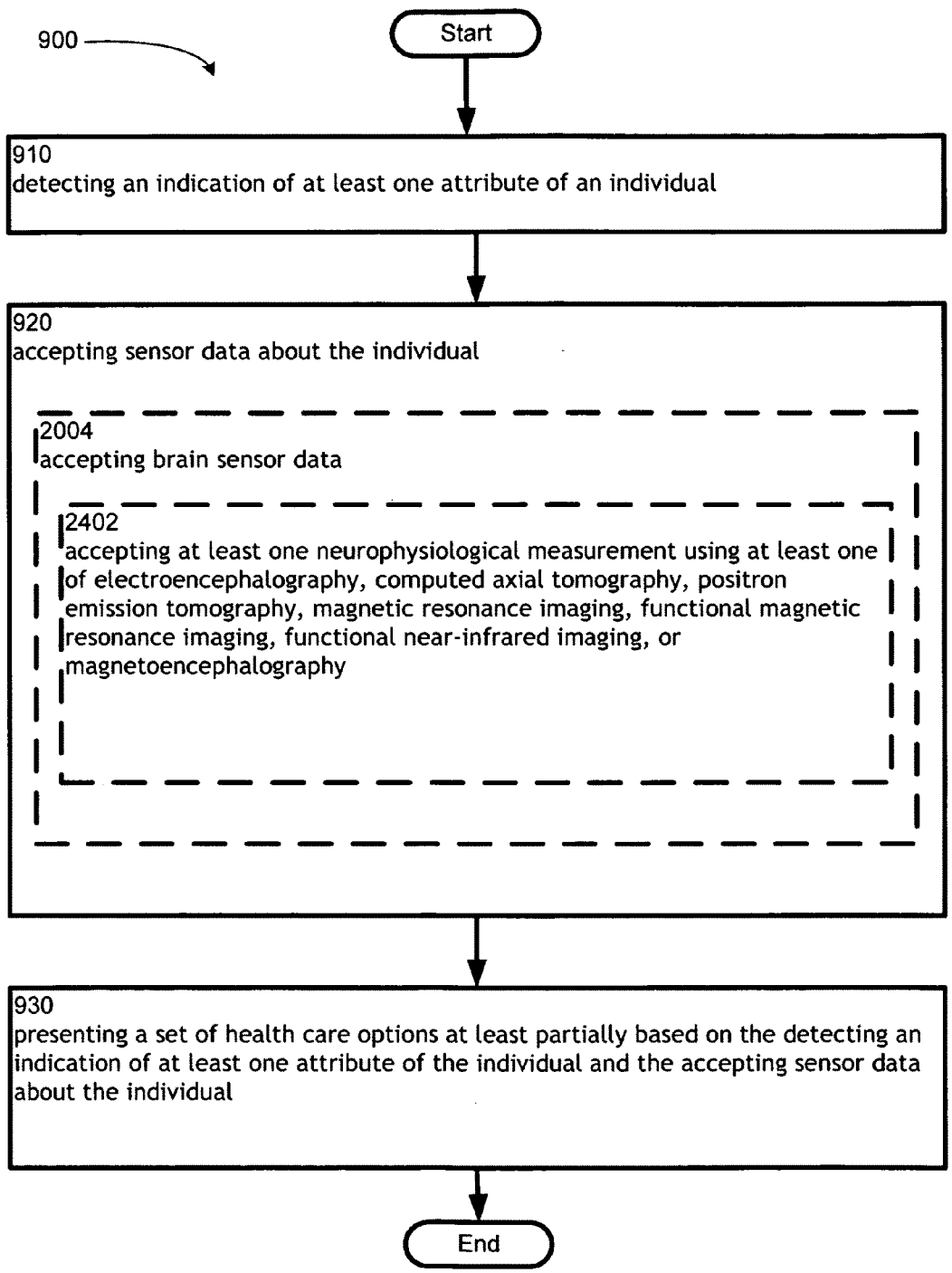
FIG. 24 illustrates an alternative embodiment of the operational flow of FIG. 9.

FIG. 24 illustrates alternative embodiments of the example operational flow 800 of FIG. 8. FIG. 24 illustrates example embodiments where operation 920 may include at least one additional operation. Additional operations may include operation 2402.

Further, operation 2402 illustrates accepting at least one neurophysiological measurement using at least one of electroencephalography, computed axial tomography, positron emission tomography, magnetic resonance imaging, functional magnetic resonance imaging, functional near-infrared imaging, or magnetoencephalography. For example, as shown in FIGS. 4 through 8, measurement accepter module 674 can accept at least one neurophysiological measurement using at least one of electroencephalography, computed axial tomography, positron emission tomography, magnetic resonance imaging, functional magnetic resonance imaging, functional near-infrared imaging, or magnetoencephalography. In some instances, measurement accepter module 674 may include a computer processor, and/or a medical device, such as an apparatus configured to perform a computed axial tomography scan.

Electroencephalography may include measuring the electrical activity of the brain by recording from electrodes placed on the scalp or, in special cases, subdurally, or in the cerebral cortex, or from remote sensors. The resulting traces are known as an electroencephalogram (EEG) and represent a summation of post-synaptic potentials from a large number of neurons. EEG is most sensitive to a particular set of post-synaptic potentials: those which are generated in superficial layers of the cortex, on the crests of gyri directly abutting the skull and radial to the skull. Dendrites that are deeper in the cortex, inside sulci, are in midline or deep structures (such as the cingulate gyrus or hippocampus) or that produce currents that are tangential to the skull make a smaller contribution to the EEG signal.

One application of EEG is event-related potential (ERP) analysis. An ERP is any measured brain response that is directly the result of a thought or perception. ERPs can be reliably measured using electroencephalography (EEG), a procedure that measures electrical activity of the brain, typically through the skull and scalp. As the EEG reflects thousands of simultaneously ongoing brain processes, the brain response to a certain stimulus or event of interest is usually not visible in the EEG. One of the most robust features of the ERP response is a response to unpredictable stimuli. This response is known as the P300 (P3) and manifests as a positive deflection in voltage approximately 300 milliseconds after the stimulus is presented.

A two-channel wireless brain wave monitoring system powered by a thermo-electric generator has been developed by IMEC (Interuniversity Microelectronics Centre, Leuven, Belgium). This device uses the body heat dissipated naturally from the forehead as a means to generate its electrical power. The wearable EEG system operates autonomously with no need to change or recharge batteries. The EEG monitor prototype is wearable and integrated into a headband where it consumes 0.8 milliwatts. A digital signal processing block encodes extracted EEG data, which is sent to a PC via a 2.4-GHz wireless radio link. The thermoelectric generator is mounted on the forehead and converts the heat flow between the skin and air into electrical power. The generator is composed of 10 thermoelectric units interconnected in a flexible way. At room temperature, the generated power is about 2 to 2.5-mW or 0.03-mW per square centimeter, which is the theoretical limit of power generation from the human skin. Such a device is proposed to associate emotion with EEG signals. See Clarke, "IMEC has a brain wave: feed EEG emotion back into games," EE Times online, http://www.eetimes.eu/design/202801063 (Nov. 1, 2007).

Computed axial tomography may include medical imaging employing tomography and digital geometry processing for generating a three-dimensional image of the inside of an object from a large series of two-dimensional X-ray images taken around a single axis of rotation. Positron emission tomography may include a nuclear medicine imaging technique, which produces a three-dimensional image and/or map of at least one functional process in the body. The system detects pairs of gamma rays emitted indirectly by a positron-emitting radionuclide (a tracer), which is introduced into the body on a biologically active molecule. Images of tracer concentration in 3-dimensional space within the body may then be reconstructed by computer analysis. Magnetic resonance imaging may include a medical imaging technique using a magnetic field to align the nuclear magnetization of hydrogen atoms in water in the body, resulting in an image of the body. Functional magnetic resonance imaging may include and imaging method for measuring haemodynamic response related to neural activity in the brain or spinal cord. Functional near-infrared imaging (fNIR) may include a spectroscopic neuro-imaging method for measuring the level of neuronal activity in the brain. Functional near-infrared imaging (fNIR) is based on neurovascular coupling, or the relationship between metabolic activity and oxygen level (oxygenated hemoglobin) in feeding blood vessels.

Magnetoencephalography includes measuring the magnetic fields produced by electrical activity in the brain using magnetometers such as superconducting quantum interference devices (SQUIDs) or other devices. Smaller magnetometers are in development, including a mini-magnetometer that uses a single milliwatt infrared laser to excite rubidium in the context of an applied perpendicular magnetic field. The amount of laser light absorbed by the rubidium atoms varies predictably with the magnetic field, providing a reference scale for measuring the field. The stronger the magnetic field, the more light is absorbed. Such a system is currently sensitive to the 70 fT range, and is expected to increase in sensitivity to the 10 fT range. See Physorg.com, "New mini-sensor may have biomedical and security applications," Nov. 1, 2007, http://www.physorg.com/news113151078.html, which is incorporated herein by reference.

Figure 25:
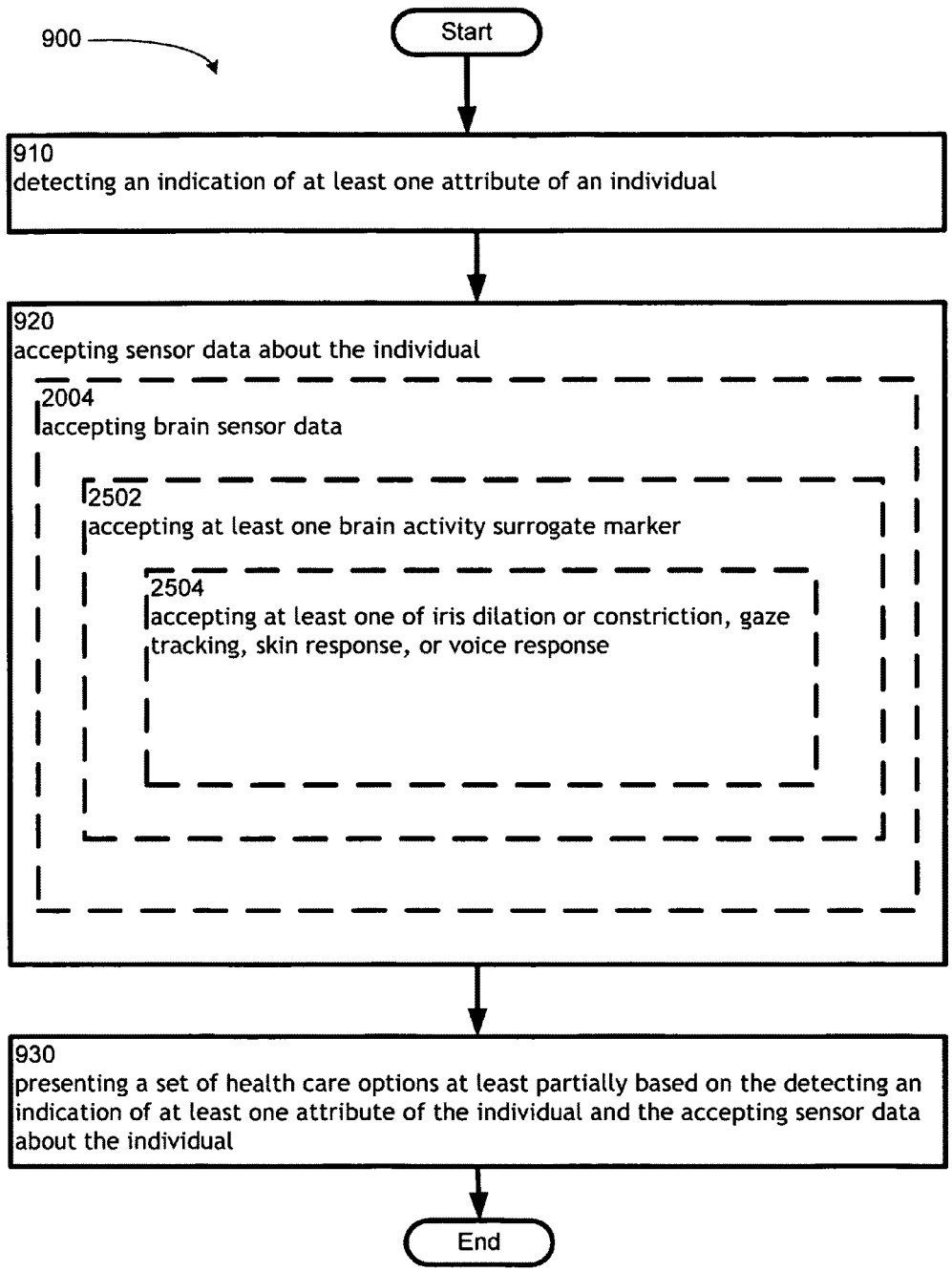
FIG. 25 illustrates an alternative embodiment of the operational flow of FIG. 9.

FIG. 25 illustrates alternative embodiments of the example operational flow 800 of FIG. 8. FIG. 25 illustrates example embodiments where operation 920 may include at least one additional operation. Additional operations may include operation 2502 and/or operation 2504.

Further, operation 2502 illustrates accepting at least one brain activity surrogate marker. For example, as shown in FIGS. 4 through 8, marker accepter module 676 can accept at least one brain activity surrogate marker. In some instances, marker accepter module 676 may include a computer processor and/or medical instrumentality configured to measure a surrogate marker, such as a stethoscope, a face recognition system, and/or a sphygmomanometer. Brain activity surrogate markers may include indicators of attention, approval, disapproval, recognition, cognition, memory, trust, or the like in response to a stimulus, other than measurement of brain activity associated with the stimulus. Some examples of surrogate markers may include a skin response to a stimulus; a face pattern indicative of approval, disapproval, or emotional state; eye movements or pupil movements indicating visual attention to an object; voice stress patterns indicative of a mental state, or the like. Surrogate markers may be used in conjunction with brain activity measurements for higher confidence in a predictive or interpretational outcome. For example, brain activation of the caudate nucleus in combination with calm voice patterns may increase confidence in a predictor of trust between a subject and a stimulus. Additional discussion regarding surrogate markers may be found in Cohn, J. N., *Introduction to Surrogate Markers*, CIRCULATION 109: IV20-21, American Heart Association, (2004), which is incorporated herein by reference.

For example, emotion links to cognition, motivation, memory, consciousness, and learning and developmental systems. Affective communication depends on complex, rule-based systems with multiple channels and redundancy built into the exchange system, in order to compensate if one channel fails. Channels can include all five senses: for example, increased heart-rate or sweating may show tension or agitation and can be heard, seen, touched, smelt or tasted. Emotional exchanges may be visible displays of body tension or movement, gestures, posture, facial expressions or use of personal space; or audible displays such as tone of voice, choice of pitch contour, choice of words, speech rate, etc. Humans also use touch, smell, adornment, fashion, architecture, mass media, and consumer products to communicate our emotional state. Universals of emotion that cross cultural boundaries have been identified, and cultural differences have also been identified. For example 'love' is generally categorized as a positive emotion in Western societies, but in certain Eastern cultures there is also a concept for 'sad love.' Accordingly, universal emotional triggers may be used to transcend cultural barriers.

When communicating with computers, people often treat new media as if they were dealing with real people. They often follow complex social rules for interaction and modify their communication to suit their perceived conversation partner. Much research has focused on the use of facial actions and ways of coding them. Speech recognition systems have also attracted attention as they grow in capability and reliability, and can recognize both verbal messages conveyed by spoken words, and non verbal messages, such as those conveyed by pitch contours.

System responses and means of expressing emotions also vary. Innovative prototypes are emerging designed to respond indirectly, so the user is relatively unaware of the response: for example by adaptation of material, such as changing pace or simplifying or expanding content. Other systems use text, voice technology, visual agents, or avatars to communicate. See Axelrod et al., "Smoke and Mirrors: Gathering User Requirements for Emerging Affective Systems," 26th Int. Conf. Information Technology Interfaces/TI 2004, Jun. 7-10, 2004, Cavtat, Croatia, pp. 323-328, which is incorporated herein by reference.

Further, operation 2504 illustrates accepting at least one of iris dilation or constriction, gaze tracking, skin response, or voice response. For example, as shown in FIGS. 4 through 8, response accepter module 678 can accept at least one of iris dilation or constriction, gaze tracking, skin response, or voice response. In some instances, response accepter module 678 may include a computer processor and/or medical instrumentality, such as a stethoscope and/or a sphygmomanometer. In one embodiment, response accepter module 678 may record changes in the movement of an individual's iris (with corresponding changes in the size of the pupil) before, during, and/or after administration of a bioactive agent and/or an artificial sensory experience. Such measurements of physiologic activity that indicate brain activity and/or mental state may be carried out at a time that is proximate to administration of a bioactive agent and/or an artificial sensory experience.

In one embodiment, response accepter module 678 may measure and/or record gaze tracking. In some instances, response accepter module 678 may include a camera that can monitor a subject's eye movements in order to determine whether the subject looks at a presented characteristic, for example, during a certain time period. For example, a camera may include a smart camera that can capture images, process them and issue control commands within a millisecond time frame. Such smart cameras are commercially available (e.g., Hamamatsu's Intelligent Vision System; http://jp.hamamatsu.com/en/product_info/index.html). Such image capture systems may include dedicated processing elements for each pixel image sensor. Other camera systems may include, for example, a pair of infrared charge coupled device cameras to continuously monitor pupil size and position as a user watches a visual target moving forward and backward. This can provide real-time data relating to pupil accommodation relative to objects on, for example, a user interface, such as a display. (e.g., http://jp.hamamatsu.com/en/rd/publication/scientific_american/common/pdf/scientific_0608.pdf).

Eye movement and/or iris movement may also be measured by video-based eye trackers. In these systems, a camera focuses on one or both eyes and records eye movement as the viewer looks at a stimulus. Contrast may be used to locate the center of the pupil, and infrared and near-infrared non-collumnated light may be used to create a corneal reflection. The vector between these two features can be used to compute gaze intersection with a surface after a calibration for an individual.

In one embodiment, response accepter module 678 may measure and/or record skin response. Brain activity may be determined by detection of a skin response associated with a stimulus. One skin response that may correlate with mental state and/or brain activity is galvanic skin response (GSR), also known as electrodermal response (EDR), psychogalvanic reflex (PGR), or skin conductance response (SCR). This is a change in the electrical resistance of the skin. There is a relationship between sympathetic nerve activity and emotional arousal, although one may not be able to identify the specific emotion being elicited. The GSR is highly sensitive to emotions in some people. Fear, anger, startle response, orienting response, and sexual feelings are all among the emotions which may produce similar GSR responses. GSR is typically measured using electrodes to measure skin electrical signals.

For example, an Ultimate Game study measured skin-conductance responses as a surrogate marker or autonomic index for affective state, and found higher skin conductance activity for unfair offers, and as with insular activation in the brain, this measure discriminated between acceptances and rejections of these offers. See Sanfey, "Social Decision-Making: Insights from Game Theory and Neuroscience," Science, vol. 318, pp. 598-601 (26 Oct. 2007), which is incorporated herein by reference. Other skin responses may include flushing, blushing, goose bumps, sweating, or the like.

In one embodiment, response accepter module 678 may measure and/or record voice response. Voice response may include speech captured by a microphone during presentation of a characteristic. Speech or voice can be measured, for example, by examining voice, song, and/or other vocal utterances of a subject before, during, and/or after administration of a bioactive agent and/or an artificial sensory experience to an individual. Such measurements may include, for example, as discussed above, layered voice analysis, voice stress analysis, or the like.

The reaction of an individual to an administered bioactive agent and/or an artificial sensory experience, such as an event in a virtual world may be a recognizable vocal exclamation such as "Wow, that's nice!" that may be detectable by a response accepter module 678, such as a microphone monitoring the subject while being administered an artificial sensory experience. A response accepter module 678 may include a voice response module and/or a speech recognition function, such as a software program or computational device that can identify and/or record an utterance of a subject as speech or voice data.

Figure 26:
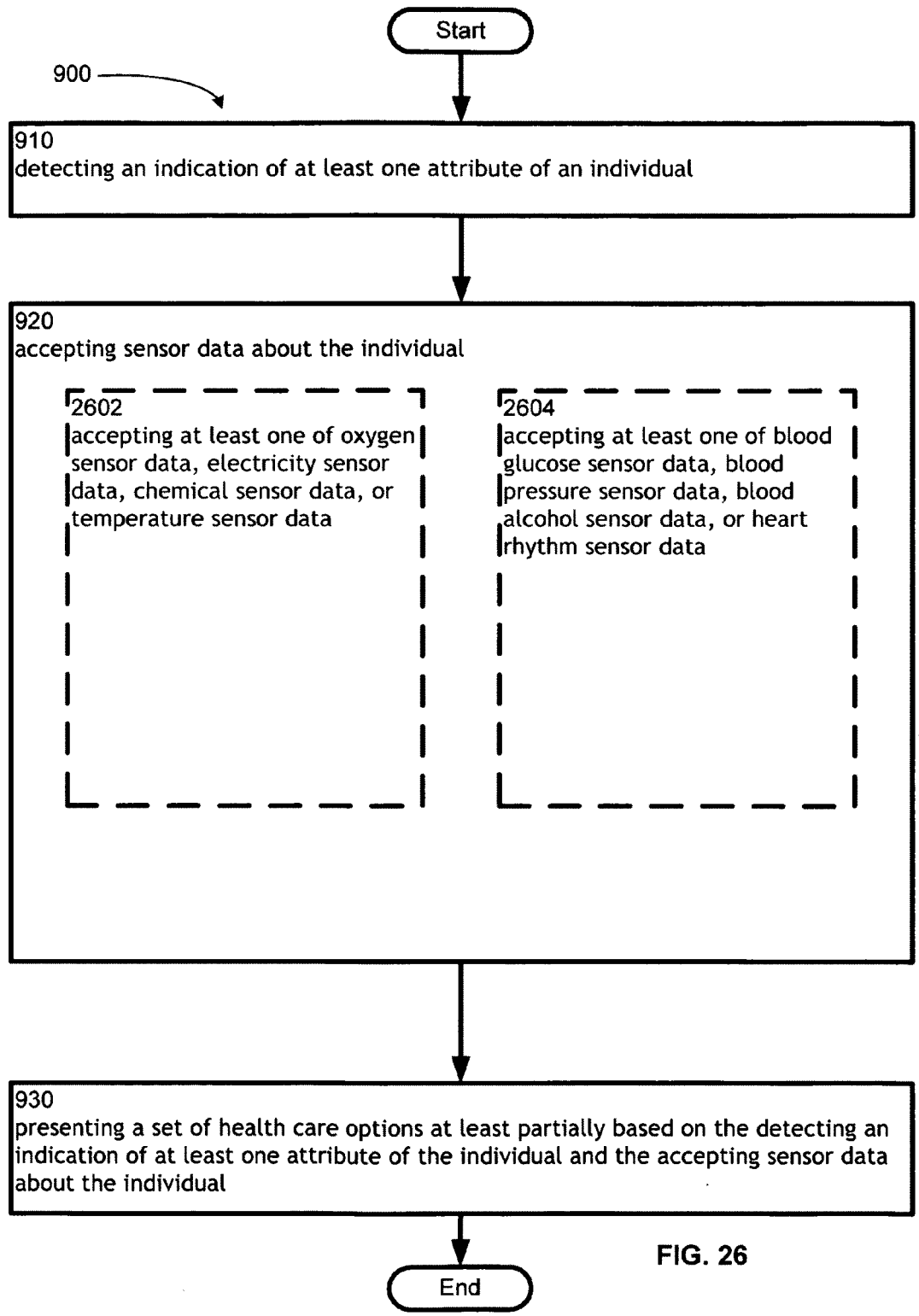
FIG. 26 illustrates an alternative embodiment of the operational flow of FIG. 9.

FIG. 26 illustrates alternative embodiments of the example operational flow 800 of FIG. 8. FIG. 26 illustrates example embodiments where operation 920 may include at least one additional operation. Additional operations may include operation 2602 and/or operation 2604.

Operation 2602 illustrates accepting at least one of oxygen sensor data, electricity sensor data, chemical sensor data, or temperature sensor data. For example, as shown in FIGS. 4 through 8, physiological data accepter module 680 can accept at least one of oxygen sensor data, electricity sensor data, chemical sensor data, or temperature sensor data. In an embodiment, physiological data accepter module 680 may accept temperature sensor data from an infrared thermometer. One example of an oxygen sensor may include a pulse oximeter. Another example of an oxygen sensor may be found in Milstein et al., U.S. Pat. No. 5,106,482. Some examples of an electricity sensor may include an electroencephalography sensor and/or a piezoelectric ultrasound transducer. An additional example of an electricity sensor may include the bio-electric sensor found in Shahinpoor et al., U.S. Pat. No. 6,829,499, which is incorporated herein by reference. A chemical sensor may include, for example, a pH meter and/or a blood glucose sensor. An additional chemical sensor system may be found in Darrow et al., U.S. Pat. No. 6,480,730, which is incorporated herein by reference. Some examples of a temperature sensor may include a thermocouple and/or a thermometer. An additional example of a temperature system may be found in Takaki, U.S. Pat. No. 6,019,507, which is incorporated herein by reference. In some instances, physiological data accepter module 680 may include a computer processor and/or connecting circuitry, such as wired connections or a keyboard.

Operation 2604 illustrates accepting at least one of blood glucose sensor data, blood pressure sensor data, blood alcohol sensor data, or heart rhythm sensor data. For example, as shown in FIGS. 4 through 8, blood sensor data accepter module 682 can accept at least one of blood glucose sensor data, blood pressure sensor data, blood alcohol sensor data, or heart rhythm sensor data. In an embodiment, blood sensor data accepter module 682 may accept blood glucose sensor data. One example of a blood glucose meter may include the ACCU-CHEK Aviva Blood Glucose Meter available from Roche, Basel, Switzerland. An example of a blood pressure sensor may include a blood pressure cuff and/or a sphygmomanometer. An example of a blood alcohol sensor may include a breathalyzer such as the BACtrack S50 Breathalyzer, available from KHN Solutions LLC, San Francisco, Calif. An example of a heart rhythm sensor may include an EKG based heart rate monitor, such as the monitor found in Lo et al., U.S. Pat. No. 5,738,104, or the heart sound sensor found in Anderson et al., U.S. Patent Publication No. 2009/0030334, both of which are incorporated herein by reference. In some instances, blood sensor data accepter module 682 may include a computer processor.

Figure 27:
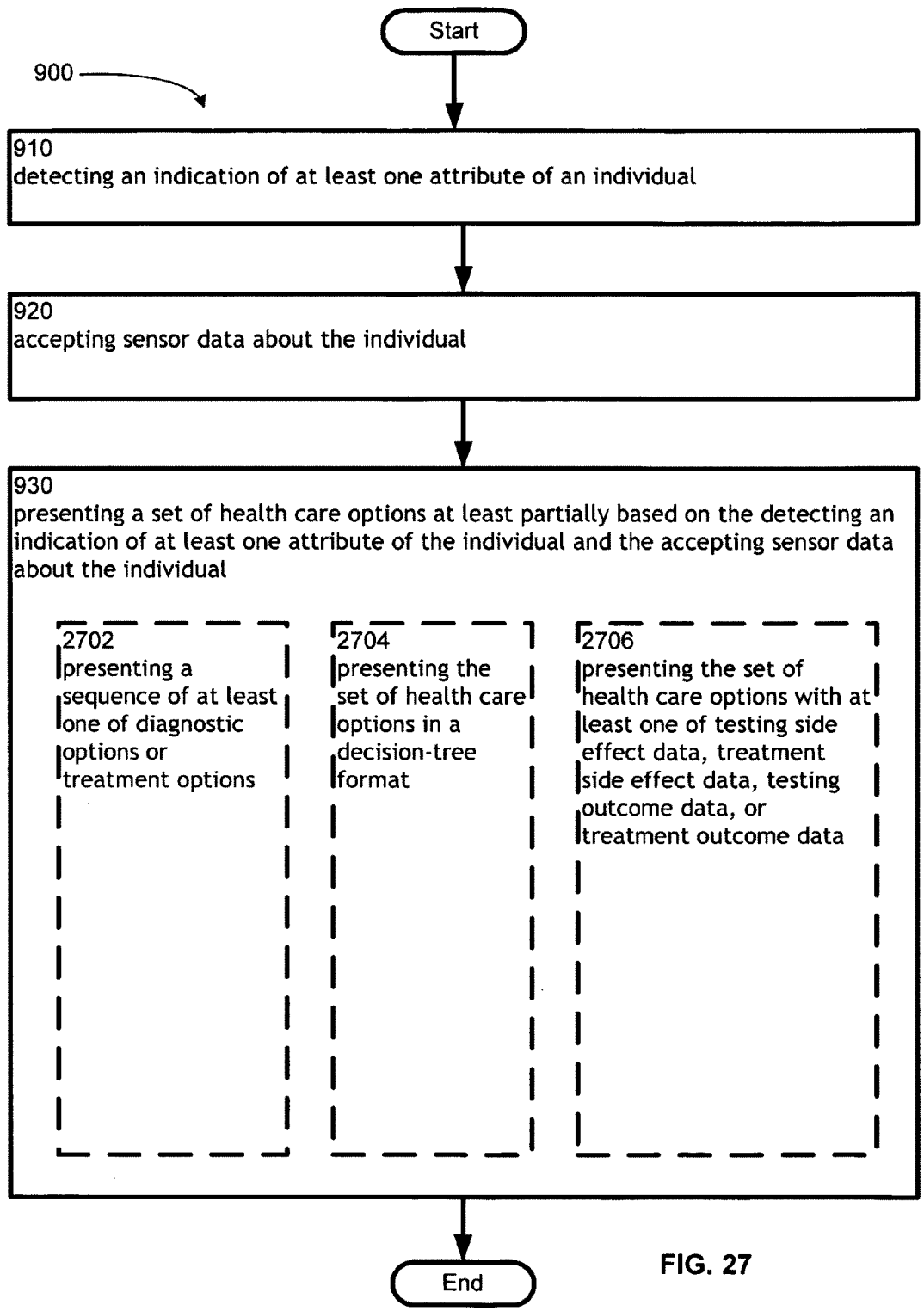
FIG. 27 illustrates an alternative embodiment of the operational flow of FIG. 9.

FIG. 27 illustrates alternative embodiments of the example operational flow 800 of FIG. 8. FIG. 27 illustrates example embodiments where operation 930 may include at least one additional operation. Additional operations may include operation 2702, operation 2704, and/or operation 2706.

Operation 2702 illustrates presenting a sequence of at least one of diagnostic options or treatment options. For example, as shown in FIGS. 4 through 8, sequence presenter module 684 can present a sequence of at least one of diagnostic options or treatment options. In one embodiment, sequence presenter module 684 can present a sequence of treatment options for obesity. A flow diagram may be determined and presented based on accepted weight sensor data, including a sequence of examinations and eventual treatment options. The list of sequential options may include service providers where appropriate, such as a weight specialist consult and a surgeon consult. This may serve to identify for the user potential service providers who may be required for providing care. In some instances, sequence presenter module 684 may include a computer processor.

Operation 2704 illustrates presenting the set of health care options in a decision-tree format. For example, as shown in FIGS. 4 through 8, format presenter module 686 can present the set of health care options in a decision-tree format. In one embodiment, format presenter module 686 may present options to address "epilepsy" as a health-related status. In this embodiment, two treatment paths may be depicted (e.g., pharmaceutical therapy (Path A) and surgery (Path B)). Such a depiction may show the treatment paths from the general to the specific, including the kinds of service provider available for each path, specific interventions typically offered by the service providers, such as types and specific drugs available by prescription in the case of Path A. In the example of Path A, the information provided by format presenter module 686 can inform a user considering pharmaceutical therapy for epilepsy. That user may use the information to contact a physician with questions about the various drugs listed/approved for treating epilepsy. In some embodiments, further information may be provided, for example, costs associated with various treatments, side effects associated with various treatments, success rates, or the like. In one embodiment, format presenter module 686 may determine a decision tree showing medical treatments. Other examples of medical treatment decision trees can be found in U.S. Pat. No. 6,807,531, which is incorporated herein in its entirety. In some instances, format presenter module 686 may include a computer processor.

Evaluation of health services options is discussed in depth in Goodman, Clifford S., "Introduction to Health Care Technology Assessment," available at http://www.nlm.nih- .gov/nichsr/hta101/ta101_c1.html, (January 2004), which is incorporated by reference herein in its entirety. An example of evaluation of health services options including a specific decision tree can be found in "Cancer in Scotland: Radiotherapy Activity Planning for Scotland 2011-2015," available at http://www.scotland.gov.uk/Publications/2006/01/24131719/28, (2006), which is incorporated by reference herein in its entirety. An example of a decision tree in the alternative medicine context can be found at http://cam.utmb.edu/curriculum/cam-decision-tree.asp and in Frenkel et al., "An approach for integrating complementary-alternative medicine into primary care," Fam. Pract., 20(3), pp. 324-332 (2003).

Operation 2706 illustrates presenting the set of health care options with at least one of testing side effect data, treatment side effect data, testing outcome data, or treatment outcome data. For example, as shown in FIGS. 4 through 8, testing data presenter module 688 can present the set of health care options with at least one of testing side effect data, treatment side effect data, or testing outcome data, treatment outcome data. In one embodiment, testing data presenter module 688 can present efficacy and/or side effect data for a given treatment option. In this embodiment, for each surgery option shown, outcome and efficacy data may be provided as well as complication and side effect data. In this embodiment, efficacy data may include improvement in long-term mortality rates, reduction in comorbidities, the rate of occurrence of epileptic episodes, or the like. Complication and side effect data may include incidence of infection, nausea, pain, or the like. In some instances, testing data presenter module 688 may include a computer processor.

Figure 28:
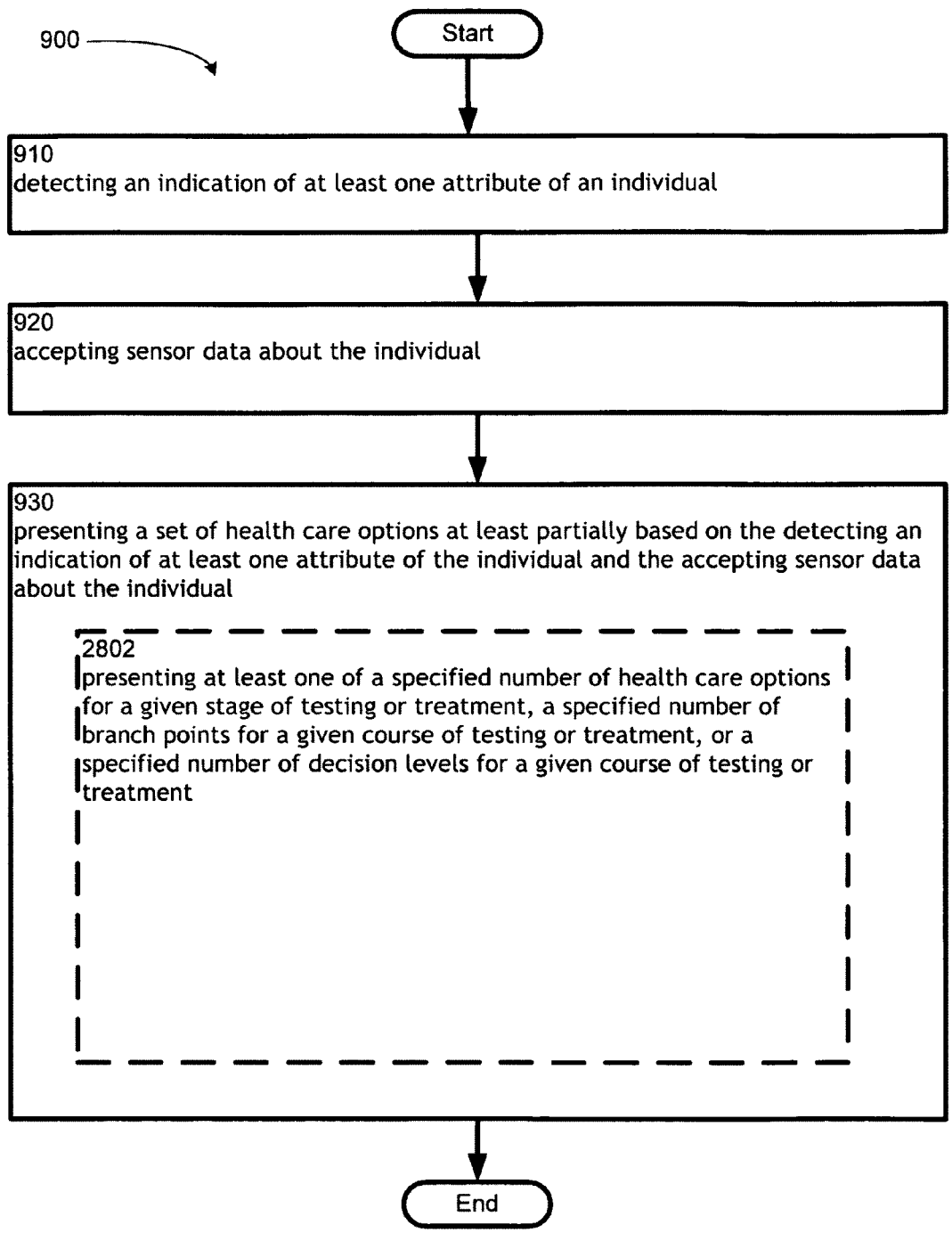
FIG. 28 illustrates an alternative embodiment of the operational flow of FIG. 9.

FIG. 28 illustrates alternative embodiments of the example operational flow 800 of FIG. 8. FIG. 28 illustrates example embodiments where operation 930 may include at least one additional operation. Additional operations may include operation 2802.

Operation 2802 illustrates presenting at least one of a specified number of health care options for a given stage of testing or treatment, a specified number of branch points for a given course of testing or treatment, or a specified number of decision levels for a given course of testing or treatment. For example, as shown in FIGS. 4 through 8, number presenter module 690 can present at least one of a specified number of health care options for a given stage of testing or treatment, a specified number of branch points for a given course of testing or treatment, or a specified number of decision levels for a given course of testing or treatment. In one embodiment, number presenter module 690 may present a maximum of two treatment options for a given stage of treatment (e.g., Paths A and B in the above example. In another embodiment, one testing/treatment option may be shown at each stage of testing/treatment. In this embodiment, several options are collapsed into one option box. For example, a surgery option box may include several options such as resection of lesions, palliative surgery, and hemispherectomy. These additional options may be shown if the user so chooses. Benefits of limiting the number of options at each stage include making the decision tree more manageable to digest and understand in terms of presenting a big picture of a prospective course of testing and/or treatment. Conversely, expanding the number of options provides more information about the options available at each stage. In some instances, number presenter module 690 may include a computer processor.

Figure 29:
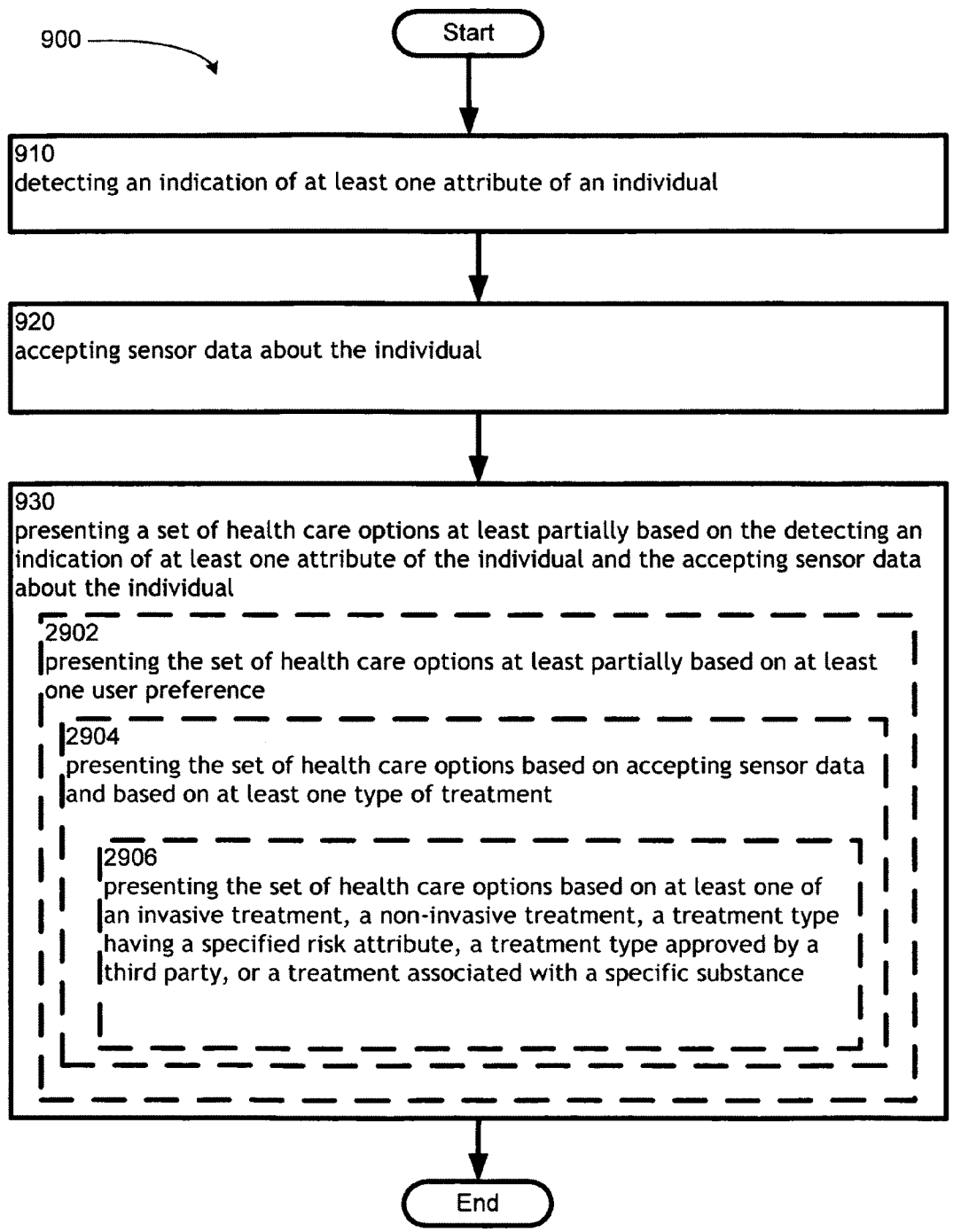
FIG. 29 illustrates an alternative embodiment of the operational flow of FIG. 9.

FIG. 29 illustrates alternative embodiments of the example operational flow 800 of FIG. 8. FIG. 29 illustrates example embodiments where operation 930 may include at least one additional operation. Additional operations may include operation 2902, operation 2904, and/or operation 2906.

Operation 2902 illustrates presenting the set of health care options at least partially based on at least one user preference. For example, as shown in FIGS. 4 through 8, preference presenter module 692 can present the set of health care options at least partially based on at least one user preference. In one embodiment, preference presenter module 692 may present, for example, a course of testing and/or treatment that takes into account one or more preferences or sensitivities of the individual, such as "treatments other than surgery," "local treatment options," "non-narcotic treatment options," or the like. In some instances, preference presenter module 692 may include a computer processor.

Further, operation 2904 illustrates presenting the set of health care options based on accepting sensor data and based on at least one type of treatment. For example, as shown in FIGS. 4 through 8, accepted data presenter module 694 can present the set of health care options based on accepting sensor data and based on at least one type of treatment. In one embodiment, accepted data presenter module 694 may present a set of health service options for an individual based on brain sensor data that indicates a likelihood of epilepsy and an individual's preference of treatment type. In this example, a user may specify a preference that excludes alternative medicine options, and/or that includes surgery options. In some instances, accepted data presenter module 694 may include a computer processor.

Further, operation 2906 illustrates presenting the set of health care options based on at least one of an invasive treatment, a non-invasive treatment, a treatment type having a specified risk attribute, a treatment type approved by a third party, or a treatment associated with a specific substance. For example, as shown in FIGS. 4 through 8, treatment presenter module 696 can present the set of health care options based on at least one of an invasive treatment, a non-invasive treatment, a treatment type having a specified risk attribute, a treatment type approved by a third party, or a treatment associated with a specific substance. In one embodiment, treatment presenter module 696 may access user preference data in order to present a health service option for the individual. For example, a user preference against surgery as an option for epilepsy may lead to a determination of Paths A and B in the above example. In another example, treatment presenter module 696 may access a standard of care database in order to determine health care options for treating epilepsy that are approved by, for example, the American Medical Association as a third party. In some instances, treatment presenter module 696 may include a computer processor.

Figure 30:
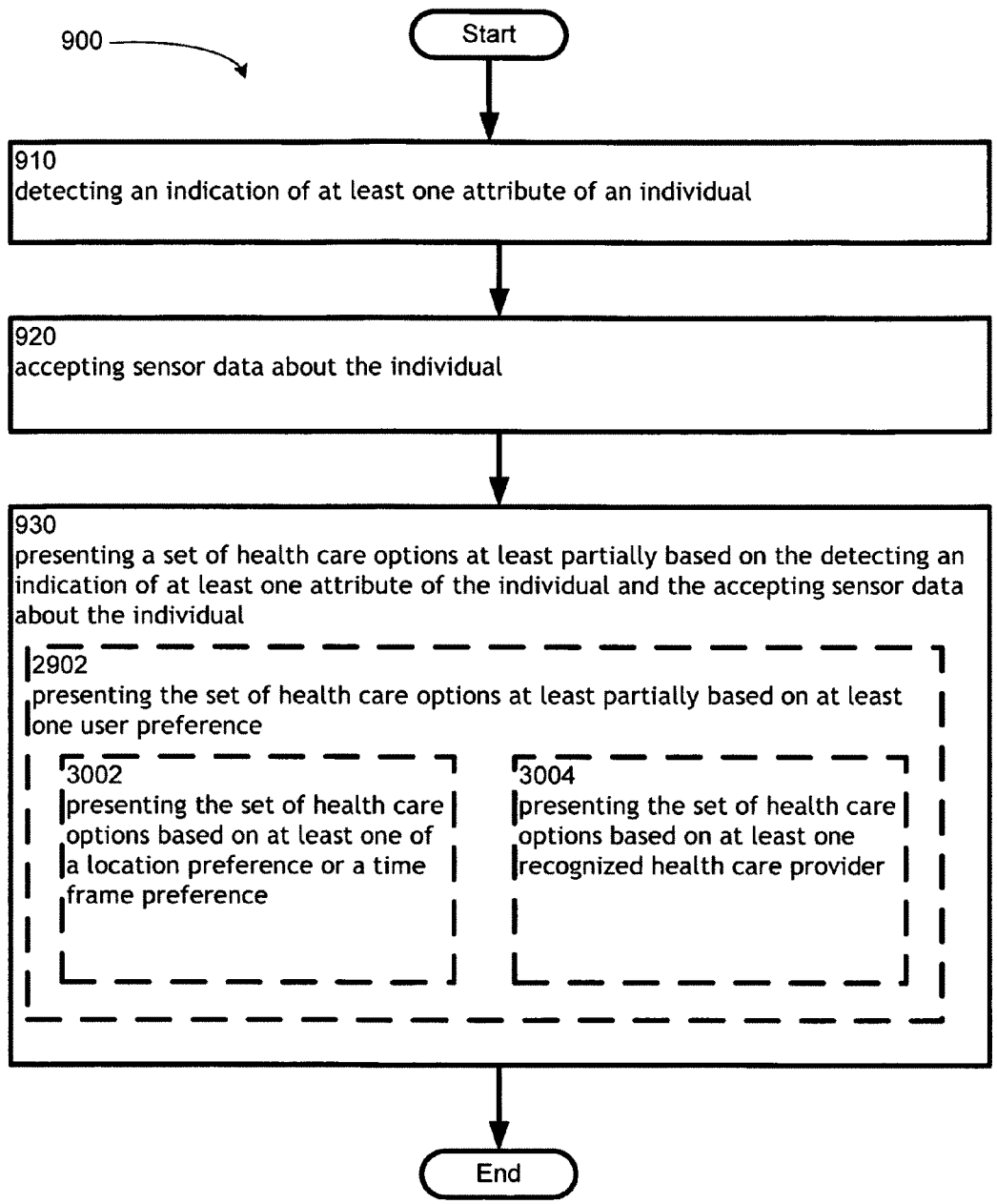
FIG. 30 illustrates an alternative embodiment of the operational flow of FIG. 9.

FIG. 30 illustrates alternative embodiments of the example operational flow 800 of FIG. 8. FIG. 30 illustrates example embodiments where operation 930 may include at least one additional operation. Additional operations may include operation 3002 and/or operation 3004.

Further, operation 3002 illustrates presenting the set of health care options based on at least one of a location preference or a time frame preference. For example, as shown in FIGS. 4 through 8, location preference module 698 can present the set of health care options based on at least one of a location preference or a time frame preference. In one embodiment, location preference module 698 may present at least one health service option based on brain sensor data indicating a likelihood of epileptic seizure and a location such as "Miami-Dade County, Fla." A database of relevant service providers may contain, inter alia, location information allowing location preference module 698 to present or determine, in this example, only relevant surgeons located in Miami-Dade County, Fla. Additionally, location preference module 698 may filter out database results that include surgeons with, for example, less than five years of experience in practice and/or located outside of a specified geographic area, in some cases resulting in zero options being listed for a given therapy. In a case where no options are returned, other treatment options may be selected and a new search carried out. In some instances, location preference module 698 may include a computer processor.

Further, operation 3004 illustrates presenting the set of health care options based on at least one recognized health care provider. For example, as shown in FIGS. 4 through 8, recognized provider presenter module 700 can present the set of health care options based on at least one recognized health care provider. In one embodiment, recognized provider presenter module 700 may present a surgeon as a health service option based on the key phrase "epileptic surgery" and certified by the "American Board of Surgery" as the recognized health care provider. Some other examples of recognized health care providers may include ranked doctors, ranked hospitals, health care providers having an award for quality of care, or the like. In some instances, recognized provider presenter module 700 may include a computer processor.

Figure 31:
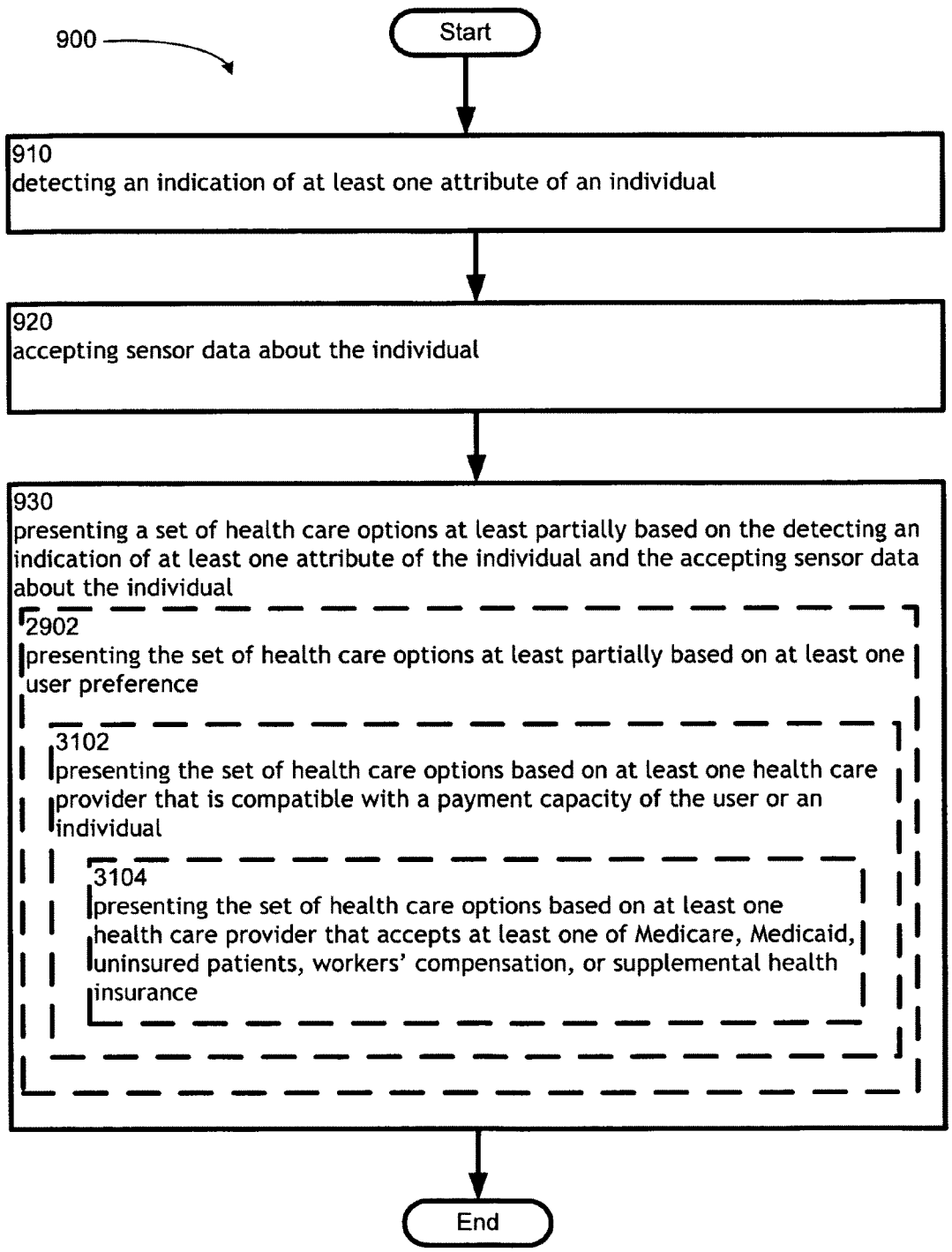
FIG. 31 illustrates an alternative embodiment of the operational flow of FIG. 9.

FIG. 31 illustrates alternative embodiments of the example operational flow 800 of FIG. 8. FIG. 31 illustrates example embodiments where operation 930 may include at least one additional operation. Additional operations may include operation 3102 and/or operation 3104.

Further, operation 3102 illustrates presenting the set of health care options based on at least one health care provider that is compatible with a payment capacity of the user or an individual. For example, as shown in FIGS. 4 through 8, payment presenter module 702 can present the set of health care options based on at least one health care provider that is compatible with a payment capacity of the user or an individual. In one embodiment, payment presenter module 702 may present treatment options based on the key phrase "Alzheimer's" (determined by utilizing brain sensor data) and "Medicaid" as the payment capacity of the individual. In this example, treatment options available for payment with Medicaid may be determined and presented to the user. These treatment options will be limited to those approved by the United States Food and Drug Administration, while others, such as Aricept®, may be omitted as incompatible with Medicaid coverage. Conversely, if the payment capacity for the individual is high, off-label treatments and those with experimental status may be included as treatment options. Examples of other payment capacities include specific private insurance plans such as Premera, Blue Cross/Blue Shield, or the like. Other examples include Medicare, fee-for-service, point-of-service, preferred provider organizations, or health maintenance organizations. In some instances, payment presenter module 702 may include a computer processor.

Further, operation 3104 illustrates presenting the set of health care options based on at least one health care provider that accepts at least one of Medicare, Medicaid, uninsured patients, workers' compensation, or supplemental health insurance. For example, as shown in FIGS. 4 through 8, insurance presenter module 704 can present the set of health care options based on at least one health care provider that accepts at least one of Medicare, Medicaid, uninsured patients, workers' compensation, or supplemental health insurance. In one embodiment, insurance presenter module 704 may present at least one health service option based on an accepted key phrase such as "Cerebral palsy" and "no insurance" as indications of at least one health-related status of an individual. In this example, insurance presenter module 704 may determine care options that are available to an uninsured individual, such as services provided by Denver Health, Denver's public health system, or the Seton System in Central Texas. In some instances, insurance presenter module 704 may include a computer processor.

Figure 32:
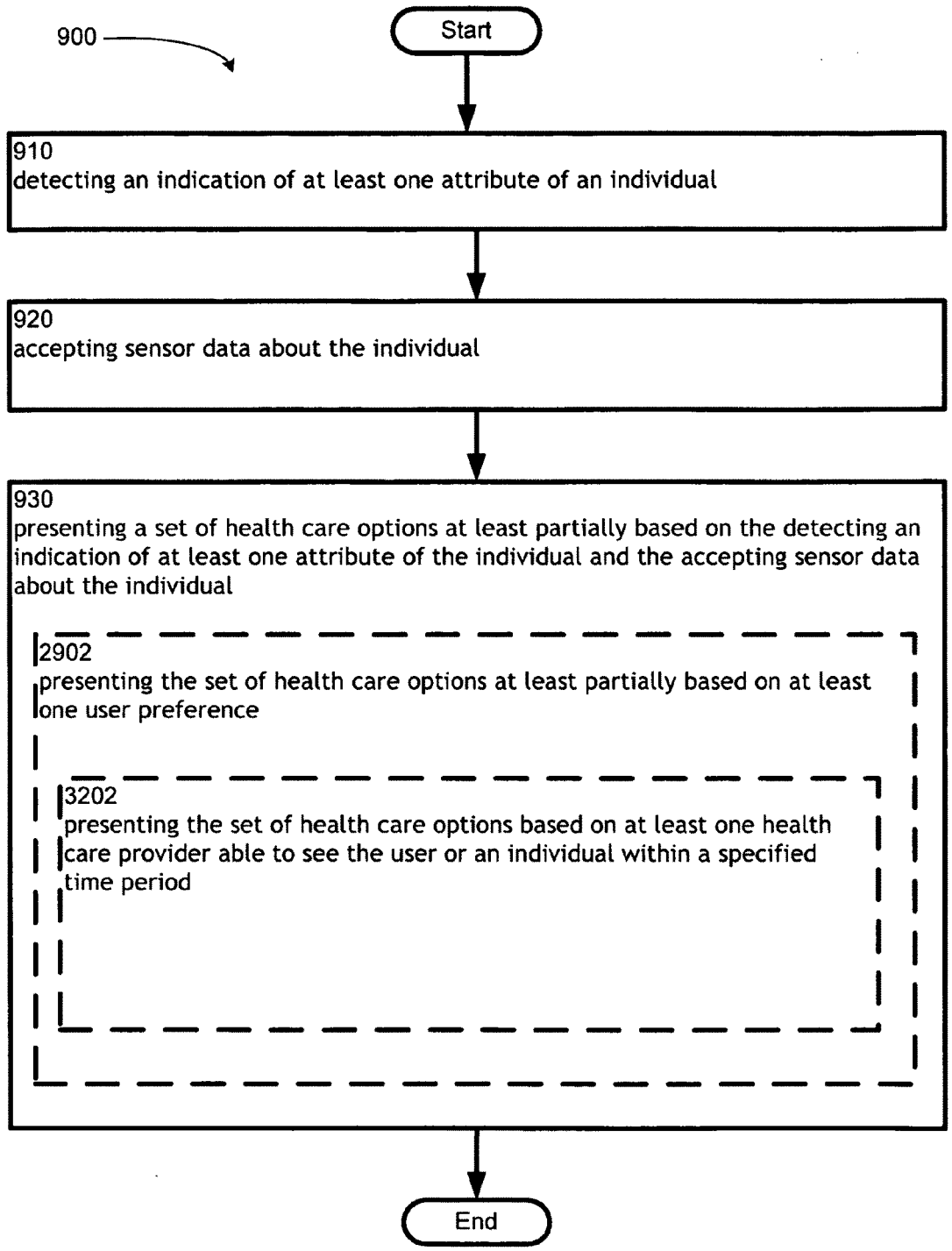
FIG. 32 illustrates an alternative embodiment of the operational flow of FIG. 9.

FIG. 32 illustrates alternative embodiments of the example operational flow 800 of FIG. 8. FIG. 32 illustrates example embodiments where operation 930 may include at least one additional operation. Additional operations may include operation 3202.

Further, operation 3202 illustrates presenting the set of health care options based on at least one health care provider able to see the user or an individual within a specified time period. For example, as shown in FIGS. 4 through 8, time period presenter module 706 can present the set of health care options based on at least one health care provider able to see the user or an individual within a specified time period. In one embodiment, time period presenter module 706 may present information about home care nurses who have immediate availability according to the individual's needs and may present a set of available home care nurses in response to accepting "hospice care" and "immediate availability" as accepted indications of health-related status of an individual. In some instances, time period presenter module 706 may include a computer processor.

Figure 33:
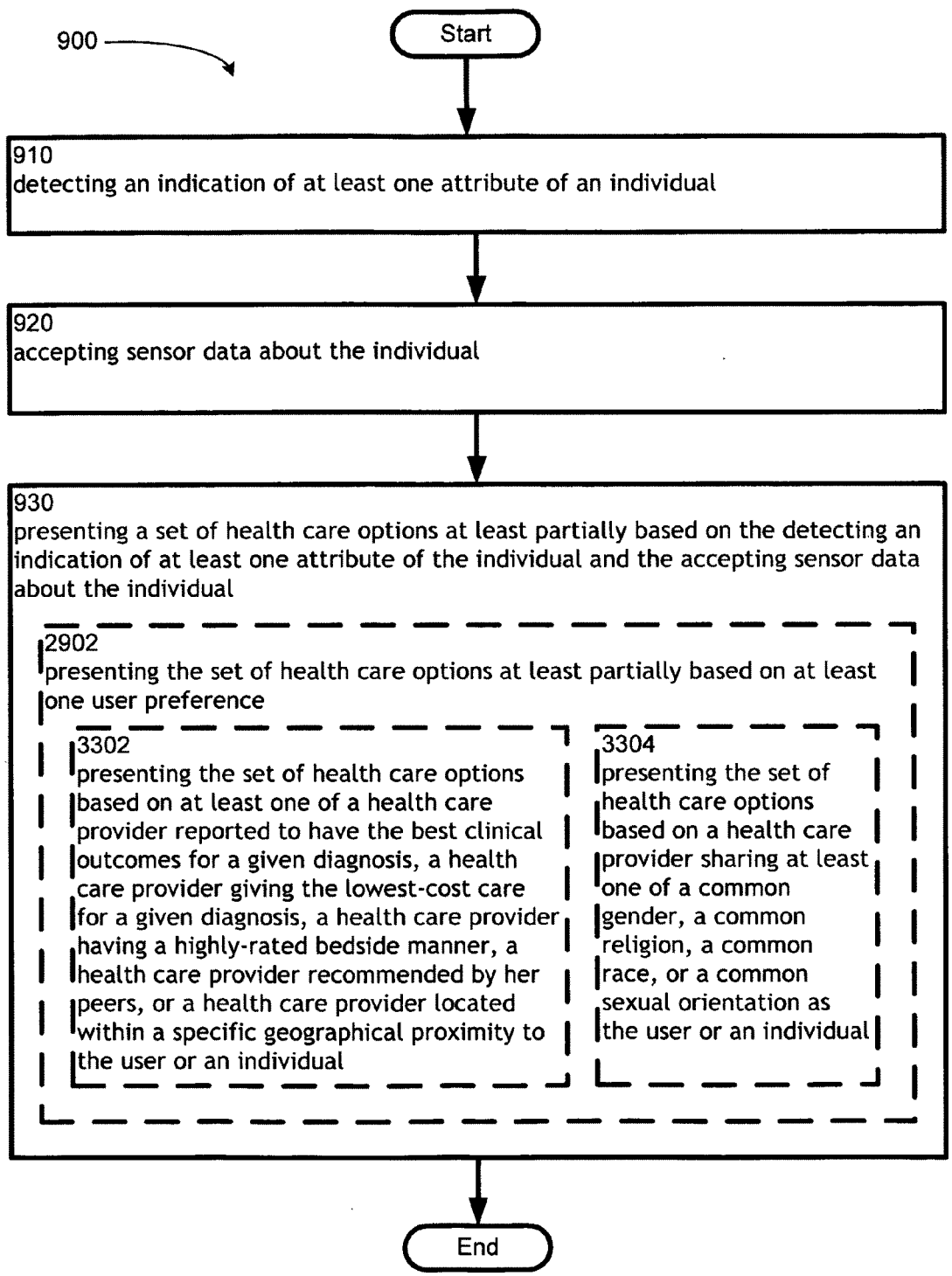
FIG. 33 illustrates an alternative embodiment of the operational flow of FIG. 9.

FIG. 33 illustrates alternative embodiments of the example operational flow 800 of FIG. 8. FIG. 33 illustrates example embodiments where operation 930 may include at least one additional operation. Additional operations may include operation 3302 and/or 3304.

Further, operation 3302 illustrates presenting the set of health care options based on at least one of a health care provider reported to have the best clinical outcomes for a given diagnosis, a health care provider giving the lowest-cost care for a given diagnosis, a health care provider having a highly-rated bedside manner, a health care provider recommended by her peers, or a health care provider located within a specific geographical proximity to the user or an individual. For example, as shown in FIGS. 4 through 8, provider result presenter module 708 can present the set of health care options based on at least one of a health care provider reported to have the best clinical outcomes for a given diagnosis, a health care provider giving the lowest-cost care for a given diagnosis, a health care provider having a highly-rated bedside manner, a health care provider recommended by her peers, or a health care provider located within a specific geographical proximity to the user or an individual. In one embodiment, provider result presenter module 708 may access data relating to hospital rankings for neural disorders, for example the U.S. News and World Report Hospital rankings and present the hospital rankings to a user. In this example, online rankings may show the Mayo Clinic in Rochester, Minn., Mass. General Hospital in Boston, Mass., and Johns Hopkins Hospital in Baltimore, Md. as the top three hospitals for treating neurology disorders in the United States. In some instances, provider result presenter module 708 may include a computer processor.

Further, operation 3304 illustrates presenting the set of health care options based on a health care provider sharing at least one of a common gender, a common religion, a common race, or a common sexual orientation as the user or an individual. For example, as shown in FIGS. 4 through 8, commonality presenter module 710 can present the set of health care options based on a health care provider sharing at least one of a common gender, a common religion, a common race, or a common sexual orientation as the user or an individual. In an embodiment, commonality presenter module 710 can present a set of physicians based on a user's preference for a Jewish doctor based at least in part on the user's religious beliefs as a Jew. In some instances, commonality presenter module 710 may include a computer processor.

Figure 34:
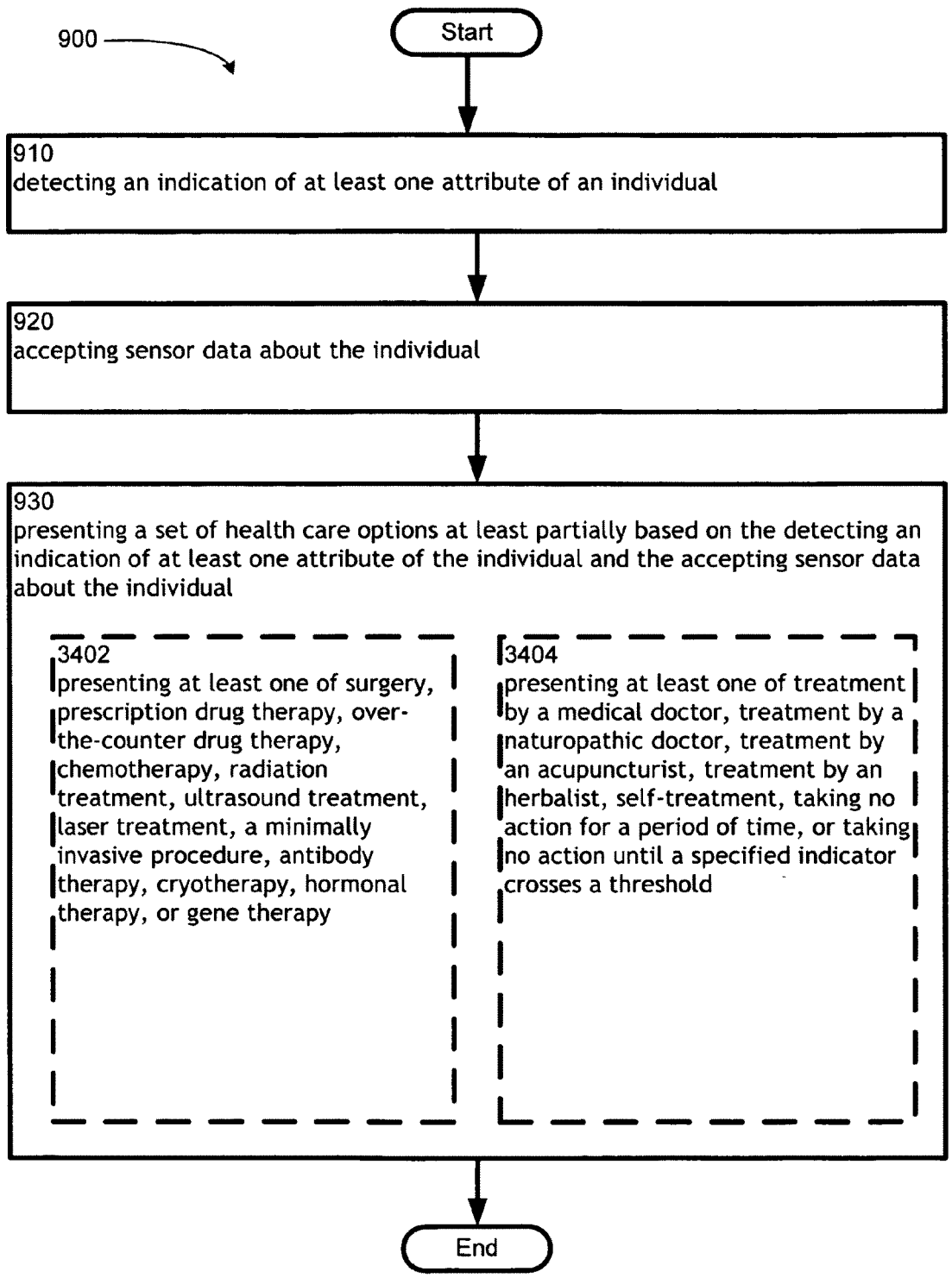
FIG. 34 illustrates an alternative embodiment of the operational flow of FIG. 9.

FIG. 34 illustrates alternative embodiments of the example operational flow 800 of FIG. 8. FIG. 34 illustrates example embodiments where operation 930 may include at least one additional operation. Additional operations may include operation 3402 and/or operation 3404.

Operation 3402 illustrates presenting at least one of surgery, prescription drug therapy, over-the-counter drug therapy, chemotherapy, radiation treatment, ultrasound treatment, laser treatment, a minimally invasive procedure, antibody therapy, cryotherapy, hormonal therapy, or gene therapy. For example, as shown in FIGS. 4 through 8, therapy presenter module 712 can present at least one of surgery, prescription drug therapy, over-the-counter drug therapy, chemotherapy, radiation treatment, ultrasound treatment, laser treatment, a minimally invasive procedure, antibody therapy, cryotherapy, hormonal therapy, or gene therapy. In one embodiment, therapy presenter module 712 may present health services options including, for example, options including prescription drug therapy and surgery based on data received from an array of non-invasive brain sensors that indicate motor neuron disease in an individual. In some instances, therapy presenter module 712 may include a computer processor.

Operation 3404 illustrates presenting at least one of treatment by a medical doctor, treatment by a naturopathic doctor, treatment by an acupuncturist, treatment by an herbalist, self-treatment, taking no action for a period of time, or taking no action until a specified indicator crosses a threshold. For example, as shown in FIGS. 4 through 8, treatment presenter module 714 can present at least one of treatment by a medical doctor, treatment by a naturopathic doctor, treatment by an acupuncturist, treatment by an herbalist, self-treatment, taking no action for a period of time, or taking no action until a specified indicator crosses a threshold. In one embodiment, treatment presenter module 714 may accept "narcolepsy" as an indication of health-related status and determine various health service options, such as treatment by an acupuncturist. In this embodiment, treatment presenter module 714 may present a list of acupuncturists with experience in treating narcolepsy. Virtually any combination of available testing/treatment options may be presented. Additionally, testing/treatment options may be narrowed by user preference. In some instances, treatment presenter module 714 may include a computer processor.

Figure 35:
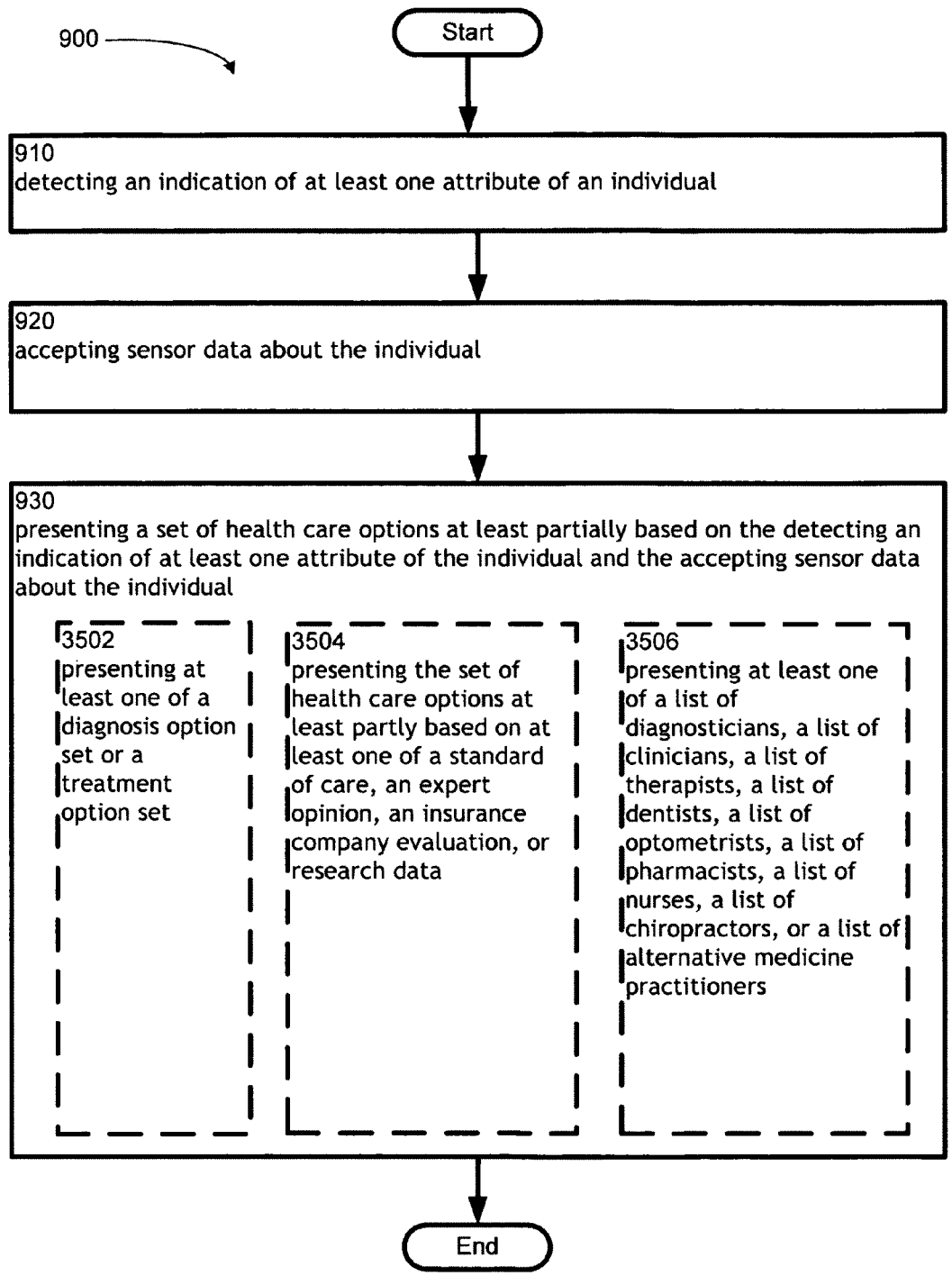
FIG. 35 illustrates an alternative embodiment of the operational flow of FIG. 9.

FIG. 35 illustrates alternative embodiments of the example operational flow 800 of FIG. 8. FIG. 35 illustrates example embodiments where operation 930 may include at least one additional operation. Additional operations may include operation 3502, operation 3504, and/or operation 3506.

Operation 3502 illustrates presenting at least one of a diagnosis option set or a treatment option set. For example, as shown in FIGS. 4 through 8, option set presenter module 716 can presenting at least one of a diagnosis option set or a treatment option set. In one embodiment, diagnosis or testing options may be determined and presented as initial steps in a decision flow diagram, followed by treatment options. In this embodiment, option set presenter module 716 may present the diagnosis and/or treatment options as a decision flow diagram as well as other presentation formats. In some instances, option set presenter module 716 may include a computer processor.

Operation 3504 illustrates presenting the set of health care options at least partly based on at least one of a standard of care, an expert opinion, an insurance company evaluation, or research data. For example, as shown in FIGS. 4 through 8, standard presenter module 718 can present the set of health care options at least partly based on at least one of a standard of care, an expert opinion, an insurance company evaluation, or research data. In one embodiment, standard presenter module 718 may present a set of health service options based on a standard of care database. The standard of care database may include information, such as treatment options that are currently recommended by the medical community and/or approved by one or more insurance companies. In some instances, standard presenter module 718 may include a computer processor.

Operation 3506 illustrates presenting at least one of a list of diagnosticians, a list of clinicians, a list of therapists, a list of dentists, a list of optometrists, a list of pharmacists, a list of nurses, a list of chiropractors, or a list of alternative medicine practitioners. For example, as shown in FIGS. 4 through 8, list presenter module 720 can present at least one of a list of diagnosticians, a list of clinicians, a list of therapists, a list of dentists, a list of optometrists, a list of pharmacists, a list of nurses, a list of chiropractors, or a list of alternative medicine practitioners. In one embodiment, list presenter module 720 can, based on accepted brain sensor data, access a service provider database to determine a list of clinicians (e.g., surgeons). In this embodiment, list presenter module 720 can present a list of clinicians experienced in treating neurological disorders indicated by the accepted brain sensor data. In another example, list presenter module 720 can access a service provider database to provide a list of physicians who are pain specialists and a list of acupuncturists in response to receiving "head pain" as an indication of health-related status. In some instances, list presenter module 720 may include a computer processor.

Figure 36:
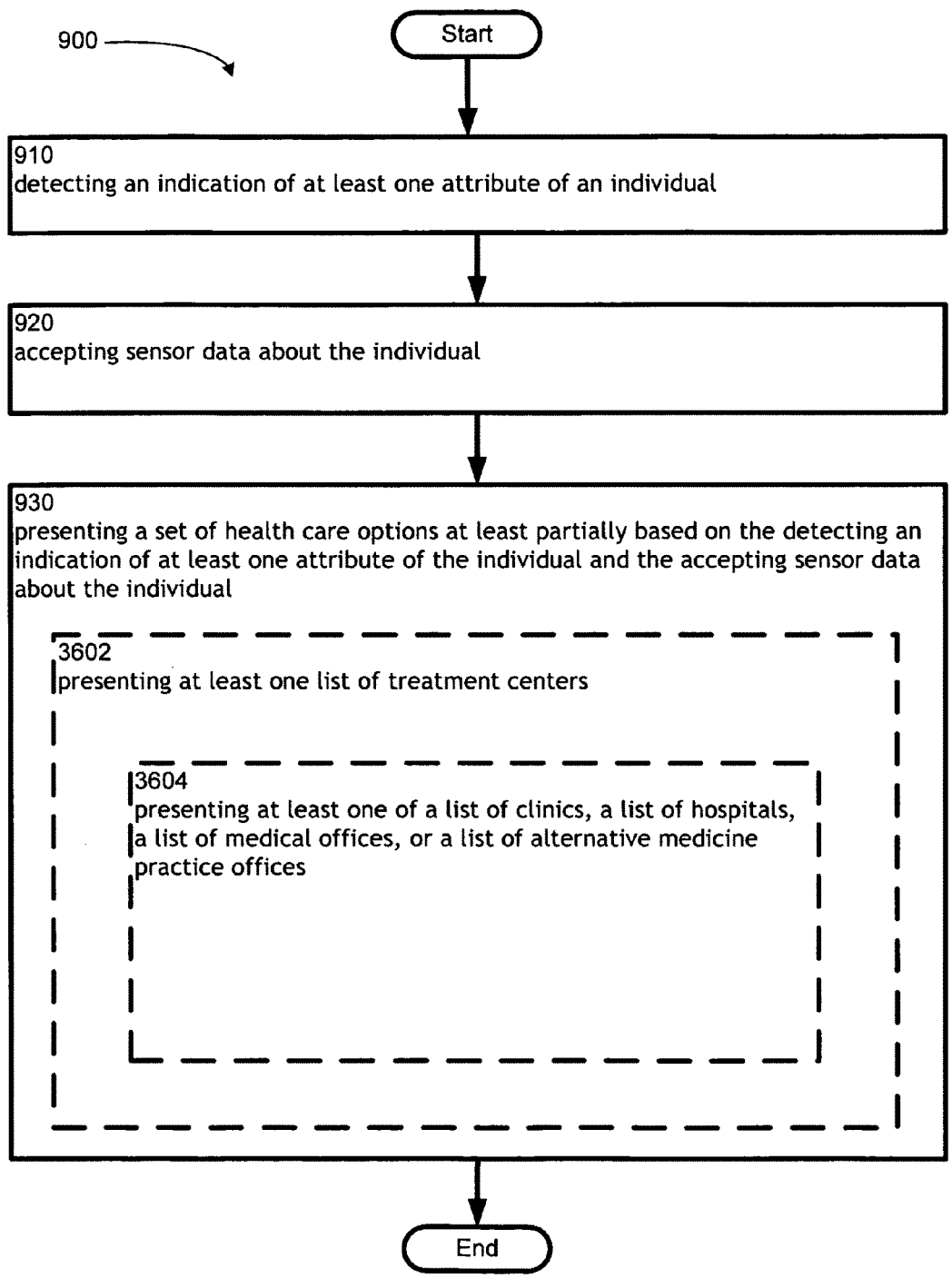
FIG. 36 illustrates an alternative embodiment of the operational flow of FIG. 9.

FIG. 36 illustrates alternative embodiments of the example operational flow 800 of FIG. 8. FIG. 36 illustrates example embodiments where operation 930 may include at least one additional operation. Additional operations may include operation 3602 and/or operation 3604.

Operation 3602 illustrates presenting at least one list of treatment centers. For example, as shown in FIGS. 4 through 8, center presenter module 722 can present at least one list of treatment centers. In one embodiment, center presenter module 722 may present a list of hospitals that perform a given medical procedure to a user at least partially based on data accepted from an array of brain sensors. In some instances, center presenter module 722 may include a computer processor.

Further, operation 3604 illustrates presenting at least one of a list of clinics, a list of hospitals, a list of medical offices, or a list of alternative medicine practice offices. For example, as shown in FIGS. 4 through 8, medical office presenter module 724 can present at least one of a list of clinics, a list of hospitals, a list of medical offices, or a list of alternative medicine practice offices. In one embodiment, medical office presenter module 724 may present a list of dementia treatment clinics for an individual in need of dementia-related health service options. In another example, medical office presenter module 724 may determine a list of epilepsy clinics. In some instances, medical office presenter module 724 may include a computer processor.

Figure 37:
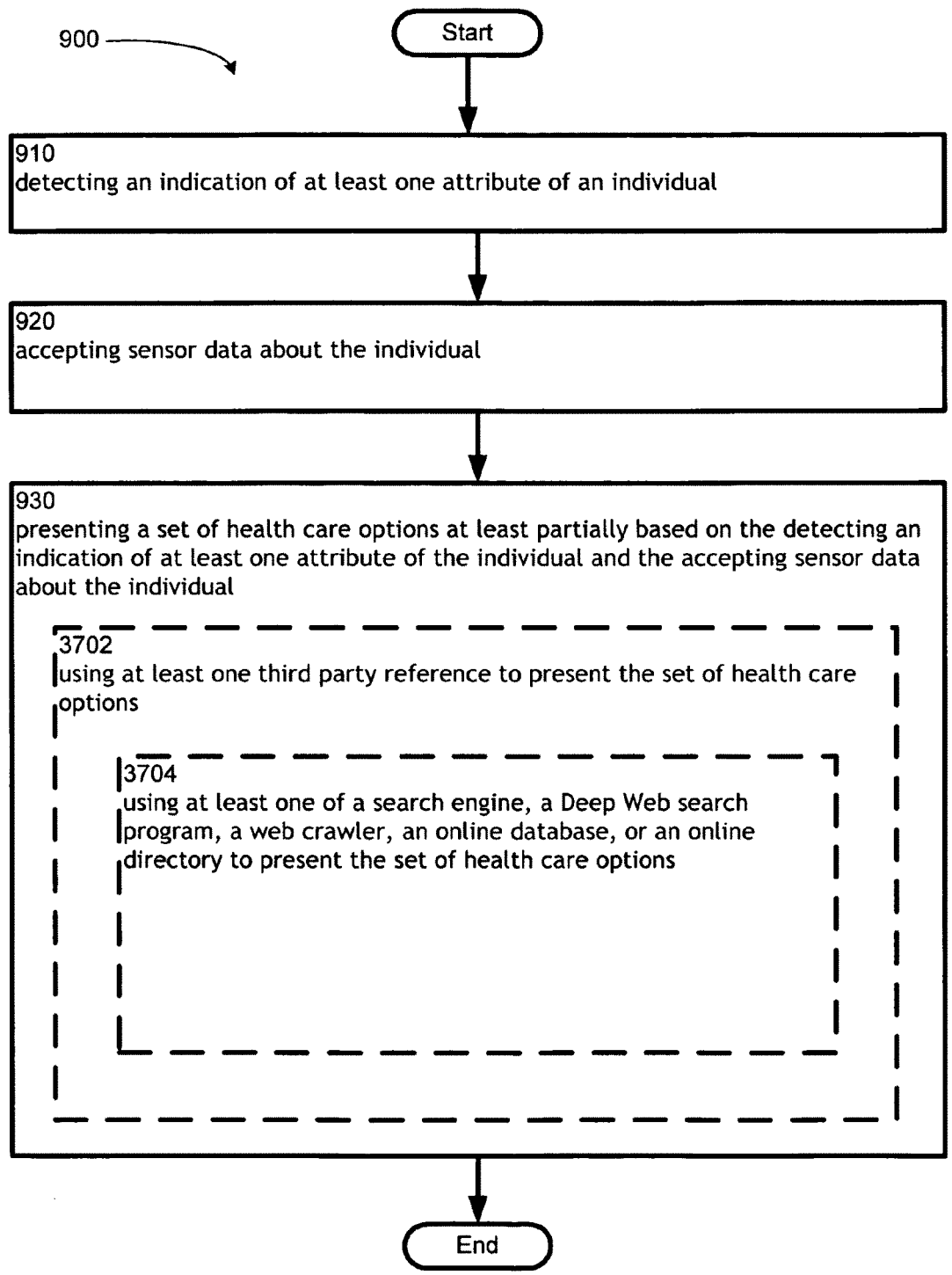
FIG. 37 illustrates an alternative embodiment of the operational flow of FIG. 9.

FIG. 37 illustrates alternative embodiments of the example operational flow 800 of FIG. 8. FIG. 37 illustrates example embodiments where operation 930 may include at least one additional operation. Additional operations may include operation 3702 and/or operation 3704.

Operation 3702 illustrates using at least one third party reference to present the set of health care options. For example, as shown in FIGS. 4 through 8, third party user module 726 can use at least one third party reference to present the set of health care options. In one embodiment, third party user module 726 may use a Physicians' Desk Reference (PDR) database to determine and then present, for example, a set of health-related services options for an individual with traumatic brain injury. In this example, third party user module 726 may use a PDR neurology database to retrieve health-related services options for a patient with traumatic brain injury. In some instances, third party user module 726 may include a computer processor.

Further, operation 3704 illustrates using at least one of a search engine, a Deep Web search program, a web crawler, an online database, or an online directory to present the set of health care options. For example, as shown in FIGS. 4 through 8, computer user module 728 can use at least one of a search engine, a Deep Web search program, a web crawler, an online database, or an online directory to present the set of health care options. In one embodiment, computer user module 728 may use a web crawler to identify a suitable online database, and then a subsequent search function to extract specific data from the online database. For example, if computer user module 728 accepts "Tourette syndrome" as an indication of at least one health-related status of an individual, it may initiate a search of the web for medical research databases containing Tourette syndrome treatment information. A possible result of this search is the medical research database "PubMed." Computer user module 728 next may search the PubMed database for "Tourette syndrome" in order to determine specific treatment information as the at least one health service option. In some instances, computer user module 728 may include a computer processor.

Figure 38:
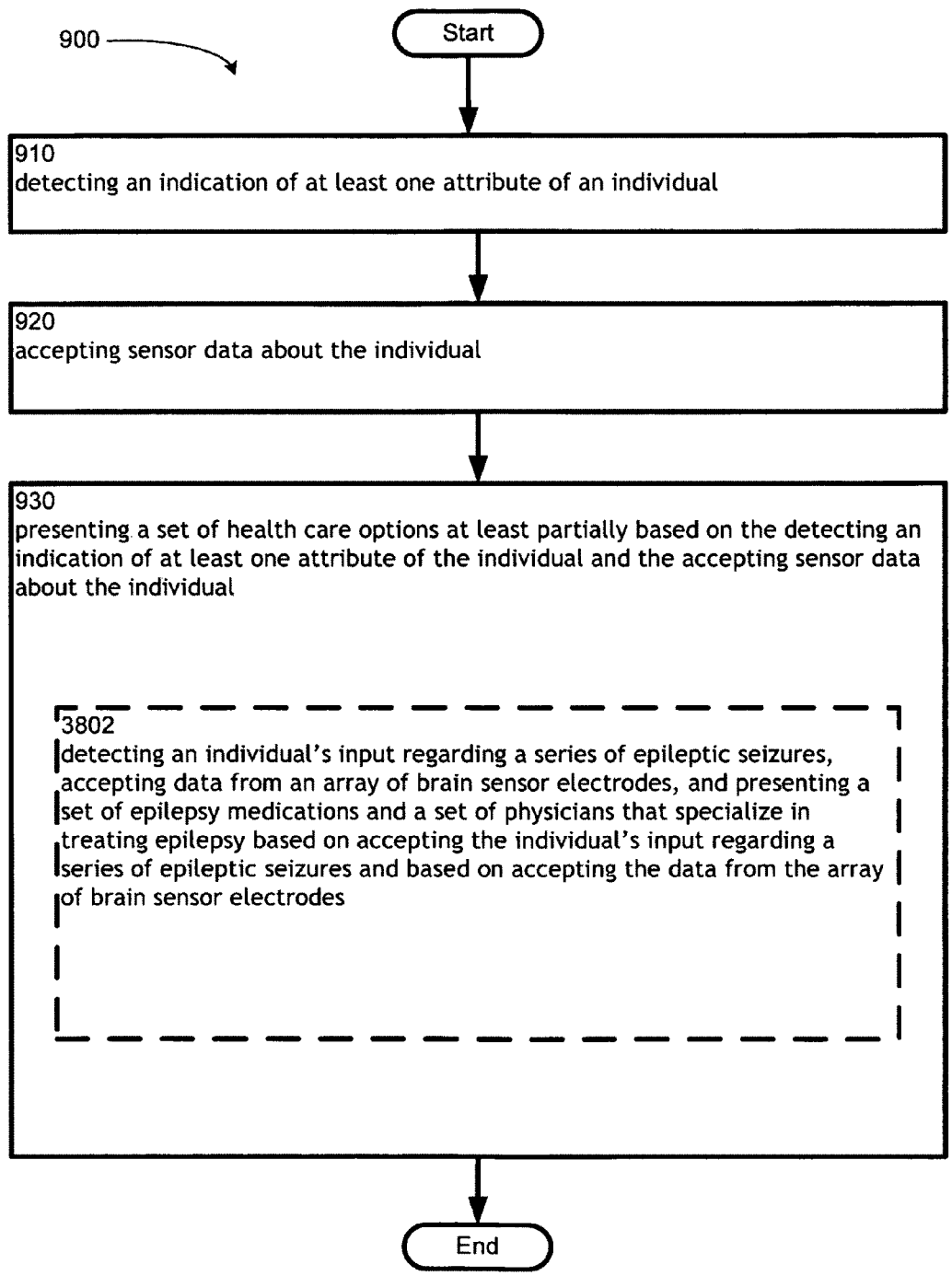
FIG. 38 illustrates an alternative embodiment of the operational flow of FIG. 9.

FIG. 38 illustrates alternative embodiments of the example operational flow 800 of FIG. 8. FIG. 38 illustrates example embodiments where operation 930 may include at least one additional operation. Additional operations may include operation 3802.

Operation 3802 illustrates detecting an individual's input regarding a series of epileptic seizures, accepting data from an array of brain sensor electrodes, and presenting a set of epilepsy medications and a set of physicians that specialize in treating epilepsy based on accepting the individual's input regarding a series of epileptic seizures and based on accepting the data from the array of brain sensor electrodes. For example, as shown in FIGS. 4 through 8, attribute accepter module 602, data accepter module 604, and presenter module 606 can accept an individual's input regarding a series of epileptic seizures, accept data from an array of brain sensor electrodes, and present a set of epilepsy medications and a set of physicians that specialize in treating epilepsy based on accepting the individual's input regarding a series of epileptic seizures and based on accepting the data from the array of brain sensor electrodes. In some instances, attribute accepter module 602 may include a computer processor. In some instances, data accepter module 604 may include a computer processor. In some instances, presenter module 606 may include a computer processor.

FIG. 39 illustrates a partial view of an example computer program product 3900 that includes a computer program 3904 for executing a computer process on a computing device. An embodiment of the example computer program product 3900 is provided using a signal-bearing medium 3902, and may include one or more instructions for detecting an indication of at least one attribute of an individual, one or more instructions for accepting sensor data about the individual, and one or more instructions for presenting a set of health care options at least partially based on the detecting an indication of at least one attribute of the individual and the accepting sensor data about the individual. The one or more instructions may be, for example, computer executable and/or logic-implemented instructions. In one implementation, the signal-bearing medium 3902 may include a computer-readable medium 3906. In one implementation, the signal bearing medium 3902 may include a recordable medium 3908. In one implementation, the signal bearing medium 3902 may include a communications medium 3910.

FIG. 40 illustrates an example system 4000 in which embodiments may be implemented. The system 4000 includes a computing system environment. The system 4000 also illustrates the user 118 using a device 4004, which is optionally shown as being in communication with a computing device 4002 by way of an optional coupling 4006. The optional coupling 4006 may represent a local, wide-area, or peer-to-peer network, or may represent a bus that is internal to a computing device (e.g., in example embodiments in which the computing device 4002 is contained in whole or in part within the device 4004). A storage medium 4008 may be any computer storage media.

The computing device 4002 includes computer-executable instructions 4010 that when executed on the computing device 4002 cause the computing device 4002 to detect an indication of at least one attribute of an individual, accept sensor data about the individual, and present a set of health care options at least partially based on the accepting an indication of at least one attribute of the individual and the accepting sensor data about the individual. As referenced above and as shown in FIG. 40, in some examples, the computing device 4002 may optionally be contained in whole or in part within the device 4004.

In FIG. 40, then, the system 4000 includes at least one computing device (e.g., 4002 and/or 4004). The computer-executable instructions 4010 may be executed on one or more of the at least one computing device. For example, the computing device 4002 may implement the computer-executable instructions 4010 and output a result to (and/or receive data from) the computing device 4004. Since the computing device 4002 may be wholly or partially contained within the computing device 4004, the device 4004 also may be said to execute some or all of the computer-executable instructions 4010, in order to be caused to perform or implement, for example, various ones of the techniques described herein, or other techniques.

The device 4004 may include, for example, a portable computing device, workstation, or desktop computing device. In another example embodiment, the computing device 4002 is operable to communicate with the device 4004 associated with the user 118 to receive information about the input from the user 118 for performing data access and data processing and presenting an output of the user-health test function at least partly based on the user data.

Although a user 140 is shown/described herein as a single illustrated figure, those skilled in the art will appreciate that a user 140 may be representative of a human user, a robotic user (e.g., computational entity), and/or substantially any combination thereof (e.g., a user may be assisted by one or more robotic agents). In addition, a user 140, as set forth herein, although shown as a single entity may in fact be composed of two or more entities. Those skilled in the art will appreciate that, in general, the same may be said of "sender" and/or other entity-oriented terms as such terms are used herein.

Those skilled in the art will appreciate that the foregoing specific exemplary processes and/or devices and/or technologies are representative of more general processes and/or devices and/or technologies taught elsewhere herein, such as in the claims filed herewith and/or elsewhere in the present application.

Those having skill in the art will recognize that the state of the art has progressed to the point where there is little distinction left between hardware, software, and/or firmware implementations of aspects of systems; the use of hardware, software, and/or firmware is generally (but not always, in that in certain contexts the choice between hardware and software can become significant) a design choice representing cost vs. efficiency tradeoffs. Those having skill in the art will appreciate that there are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation; or, yet again alternatively, the implementer may opt for some combination of hardware, software, and/or firmware. Hence, there are several possible vehicles by which the processes and/or devices and/or other technologies described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary. Those skilled in the art will recognize that optical aspects of implementations will typically employ optically-oriented hardware, software, and or firmware.

In some implementations described herein, logic and similar implementations may include software or other control structures suitable to operation. Electronic circuitry, for example, may manifest one or more paths of electrical current constructed and arranged to implement various logic functions as described herein. In some implementations, one or more media are configured to bear a device-detectable implementation if such media hold or transmit a special-purpose device instruction set operable to perform as described herein. In some variants, for example, this may manifest as an update or other modification of existing software or firmware, or of gate arrays or other programmable hardware, such as by performing a reception of or a transmission of one or more instructions in relation to one or more operations described herein. Alternatively or additionally, in some variants, an implementation may include special-purpose hardware, software, firmware components, and/or general-purpose components executing or otherwise invoking special-purpose components. Specifications or other implementations may be transmitted by one or more instances of tangible transmission media as described herein, optionally by packet transmission or otherwise by passing through distributed media at various times.

Alternatively or additionally, implementations may include executing a special-purpose instruction sequence or otherwise invoking circuitry for enabling, triggering, coordinating, requesting, or otherwise causing one or more occurrences of any functional operations described above. In some variants, operational or other logical descriptions herein may be expressed directly as source code and compiled or otherwise invoked as an executable instruction sequence. In some contexts, for example, C++ or other code sequences can be compiled directly or otherwise implemented in high-level descriptor languages (e.g., a logic-synthesizable language, a hardware description language, a hardware design simulation, and/or other such similar mode(s) of expression). Alternatively or additionally, some or all of the logical expression may be manifested as a Verilog-type hardware description or other circuitry model before physical implementation in hardware, especially for basic operations or timing-critical applications. Those skilled in the art will recognize how to obtain, configure, and optimize suitable transmission or computational elements, material supplies, actuators, or other common structures in light of these teachings.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link (e.g., transmitter, receiver, transmission logic, reception logic, etc.), etc.).

In a general sense, those skilled in the art will recognize that the various embodiments described herein can be implemented, individually and/or collectively, by various types of electro-mechanical systems having a wide range of electrical components such as hardware, software, firmware, and/or virtually any combination thereof; and a wide range of components that may impart mechanical force or motion such as rigid bodies, spring or torsional bodies, hydraulics, electro-magnetically actuated devices, and/or virtually any combination thereof. Consequently, as used herein "electro-mechanical system" includes, but is not limited to, electrical circuitry operably coupled with a transducer (e.g., an actuator, a motor, a piezoelectric crystal, a Micro Electro Mechanical System (MEMS), etc.), electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of memory (e.g., random access, flash, read only, etc.)), electrical circuitry forming a communications device (e.g., a modem, communications switch, optical-electrical equipment, etc.), and/or any non-electrical analog thereto, such as optical or other analogs. Those skilled in the art will also appreciate that examples of electro-mechanical systems include but are not limited to a variety of consumer electronics systems, medical devices, as well as other systems such as motorized transport systems, factory automation systems, security systems, and/or communication/computing systems. Those skilled in the art will recognize that electro-mechanical as used herein is not necessarily limited to a system that has both electrical and mechanical actuation except as context may dictate otherwise.

In a general sense, those skilled in the art will recognize that the various aspects described herein which can be implemented, individually and/or collectively, by a wide range of hardware, software, firmware, and/or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of memory (e.g., random access, flash, read only, etc.)), and/or electrical circuitry forming a communications device (e.g., a modem, communications switch, optical-electrical equipment, etc.). Those having skill in the art will recognize that the subject matter described herein may be implemented in an analog or digital fashion or some combination thereof.

Those skilled in the art will recognize that at least a portion of the devices and/or processes described herein can be integrated into a data processing system. Those having skill in the art will recognize that a data processing system generally includes one or more of a system unit housing, a video display device, memory such as volatile or non-volatile memory, processors such as microprocessors or digital signal processors, computational entities such as operating systems, drivers, graphical user interfaces, and applications programs, one or more interaction devices (e.g., a touch pad, a touch screen, an antenna, etc.), and/or control systems including feedback loops and control motors (e.g., feedback for sensing position and/or velocity; control motors for moving and/or adjusting components and/or quantities). A data processing system may be implemented utilizing suitable commercially available components, such as those typically found in data computing/communication and/or network computing/communication systems.

Those skilled in the art will recognize that it is common within the art to implement devices and/or processes and/or systems, and thereafter use engineering and/or other practices to integrate such implemented devices and/or processes and/or systems into more comprehensive devices and/or processes and/or systems. That is, at least a portion of the devices and/or processes and/or systems described herein can be integrated into other devices and/or processes and/or systems via a reasonable amount of experimentation. Those having skill in the art will recognize that examples of such other devices and/or processes and/or systems might include—as appropriate to context and application—all or part of devices and/or processes and/or systems of (a) an air conveyance (e.g., an airplane, rocket, helicopter, etc.), (b) a ground conveyance (e.g., a car, truck, locomotive, tank, armored personnel carrier, etc.), (c) a building (e.g., a home, warehouse, office, etc.), (d) an appliance (e.g., a refrigerator, a washing machine, a dryer, etc.), (e) a communications system (e.g., a networked system, a telephone system, a Voice over IP system, etc.), (f) a business entity (e.g., an Internet Service Provider (ISP) entity such as Comcast Cable, Qwest, Southwestern Bell, etc.), or (g) a wired/wireless services entity (e.g., Sprint, Cingular, Nextel, etc.), etc.

In certain cases, use of a system or method may occur in a territory even if components are located outside the territory. For example, in a distributed computing context, use of a distributed computing system may occur in a territory even though parts of the system may be located outside of the territory (e.g., relay, server, processor, signal-bearing medium, transmitting computer, receiving computer, etc. located outside the territory).

A sale of a system or method may likewise occur in a territory even if components of the system or method are located and/or used outside the territory.

Further, implementation of at least part of a system for performing a method in one territory does not preclude use of the system in another territory.

All of the above U.S. patents, U.S. patent application publications, U.S. patent applications, foreign patents, foreign patent applications and non-patent publications referred to in this specification and/or listed in any Application Data Sheet, are incorporated herein by reference, to the extent not inconsistent herewith.

One skilled in the art will recognize that the herein described components (e.g., operations), devices, objects, and the discussion accompanying them are used as examples for the sake of conceptual clarity and that various configuration modifications are contemplated. Consequently, as used herein, the specific exemplars set forth and the accompanying discussion are intended to be representative of their more general classes. In general, use of any specific exemplar is intended to be representative of its class, and the non-inclusion of specific components (e.g., operations), devices, and objects should not be taken limiting.

With respect to the use of substantially any plural and/or singular terms herein, those having skill in the art can translate from the plural to the singular and/or from the singular to the plural as is appropriate to the context and/or application. The various singular/plural permutations are not expressly set forth herein for sake of clarity.

The herein described subject matter sometimes illustrates different components contained within, or connected with, different other components. It is to be understood that such depicted architectures are merely exemplary, and that in fact many other architectures may be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled," to each other to achieve the desired functionality, and any two components capable of being so associated can also be viewed as being "operably couplable," to each other to achieve the desired functionality. Specific examples of operably couplable include but are not limited to physically mateable and/or physically interacting components, and/or wirelessly interactable, and/or wirelessly interacting components, and/or logically interacting, and/or logically interactable components.

In some instances, one or more components may be referred to herein as "configured to," "configurable to," "operable/operative to," "adapted/adaptable," "able to," "conformable/conformed to," etc. Those skilled in the art will recognize that "configured to" can generally encompass active-state components and/or inactive-state components and/or standby-state components, unless context requires otherwise.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of the subject matter described herein. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

With respect to the appended claims, those skilled in the art will appreciate that recited operations therein may generally be performed in any order. Also, although various operational flows are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A system, comprising:
 a device that includes at least one brain activity surrogate marker sensor, the device configured with:
 means for detecting a gaze of at least one individual;
 means for accepting brain activity surrogate marker sensor data associated with the individual from the at least one brain activity surrogate marker sensor including at least one indication of abnormal gaze based at least partially on the circuitry for detecting the gaze of the individual;
 means for detecting at least one abnormal movement associated with the at least one individual;
 means for determining whether the at least one indication of abnormal gaze of the individual and the at least one abnormal movement associated with the at least one individual are indicative of an epilepsy diagnosis; and
 means for presenting a set of epilepsy medications and a set of physicians that specialize in treating epilepsy at least partially based on the determining whether the at least one indication of abnormal gaze of the individual and the at least one abnormal movement associated with the at least one individual are indicative of an epilepsy diagnosis.

2. A system, comprising:
a device that includes at least one brain activity surrogate marker sensor the device configured with:
circuitry for detecting a gaze of at least one individual;
circuitry for accepting brain activity surrogate marker sensor data associated with the individual from the at least one brain activity surrogate marker sensor including at least one indication of abnormal gaze based at least partially on the circuitry for detecting the gaze of the individual;
circuitry for detecting at least one abnormal movement associated with the at least one individual;
circuitry for determining whether the at least one indication of abnormal gaze of the individual and the at least one abnormal movement associated with the at least one individual are indicative of an epilepsy diagnosis; and
circuitry for presenting a set of epilepsy medications and a set of physicians that specialize in treating epilepsy at least partially based on the determining whether the at least one indication of abnormal gaze of the individual and the at least one abnormal movement associated with the at least one individual are indicative of an epilepsy diagnosis.

3. The system of claim 2, wherein the circuitry for detecting the gaze of at least one individual comprises:
circuitry for detecting at least one mental attribute associated with the at least one individual based at least partially on the detected gaze of the at least one individual.

4. The system of claim 3, wherein the circuitry for detecting at least one mental attribute associated with the at least one individual based at least partially on the detected gaze of the at least one individual comprises:
circuitry for detecting at least one mental diagnosis associated with at least one individual.

5. The system of claim 2, wherein the circuitry for accepting brain activity surrogate marker sensor data associated with the individual from the at least one brain activity surrogate marker sensor comprises:
circuitry for accepting brain sensor data.

6. The system of claim 5, wherein the circuitry for accepting brain sensor data comprises:
circuitry for accepting data from at least one neuroprosthetic or at least one brain-computer interface.

7. The system of claim 5, wherein the circuitry for accepting brain sensor comprises:
circuitry for accepting data from at least one electrocorticography electrode.

8. The system of claim 5, wherein the circuitry for accepting brain sensor comprises:
circuitry for accepting data from at least one wireless brain sensor.

9. The system of claim 2, wherein the circuitry for accepting brain activity surrogate marker sensor data associated with the individual from the at least one brain activity surrogate marker sensor comprises:
circuitry for accepting at least one of oxygen sensor data, electricity sensor data, chemical sensor data, or temperature sensor data.

10. The system of claim 2, wherein the circuitry for presenting a set of epilepsy medications and a set of physicians that specialize in treating epilepsy at least partially based on the determining whether the at least one indication of abnormal gaze of the individual and the at least one abnormal movement associated with the at least one individual are indicative of an epilepsy diagnosis comprises:
circuitry for presenting at least one of surgery, prescription drug therapy, over-the-counter drug therapy, chemotherapy, radiation treatment, ultrasound treatment, laser treatment, a minimally invasive procedure, antibody therapy, cryotherapy, hormonal therapy, or gene therapy.

11. The system of claim 2, wherein the circuitry for presenting a set of epilepsy medications and a set of physicians that specialize in treating epilepsy at least partially based on the determining whether the at least one indication of abnormal gaze of the individual and the at least one abnormal movement associated with the at least one individual are indicative of an epilepsy diagnosis comprises:
circuitry for presenting the set of epilepsy medications and a set of physicians that specialize in treating at least partially based on at least one of a standard of care, an expert opinion, an insurance company evaluation, or research data.

12. The system of claim 2, wherein the circuitry for presenting a set of epilepsy medications and a set of physicians that specialize in treating epilepsy at least partially based on the determining whether the at least one indication of abnormal gaze of the individual and the at least one abnormal movement associated with the at least one individual are indicative of an epilepsy diagnosis comprises:
circuitry for presenting at least one of a list of diagnosticians, a list of clinicians, a list of therapists, a list of dentists, a list of optometrists, a list of pharmacists, a list of nurses, a list of chiropractors, or a list of alternative medicine practitioners.

13. The system of claim 2, wherein the circuitry for presenting a set of epilepsy medications and a set of physicians that specialize in treating epilepsy at least partially based on the determining whether the at least one indication of abnormal gaze of the individual and the at least one abnormal movement associated with the at least one individual are indicative of an epilepsy diagnosis comprises:
circuitry for presenting at least one list of treatment centers.

14. The system of claim 2, wherein the circuitry for presenting a set of epilepsy medications and a set of physicians that specialize in treating epilepsy at least partially based on the determining whether the at least one indication of abnormal gaze of the individual and the at least one abnormal movement associated with the at least one individual are indicative of an epilepsy diagnosis comprises:
circuitry for using at least one third party reference to present the set of health care options.

15. A method implemented on a device that includes at least one brain activity surrogate marker sensor, comprising:
detecting a gaze of at least one individual;
accepting brain activity surrogate marker sensor data associated with the individual from the at least one brain activity surrogate marker sensor including at least one indication of abnormal gaze based at least partially on the circuitry for detecting the gaze of the individual;
detecting at least one abnormal movement associated with the at least one individual;
determining whether the at least one indication of abnormal gaze of the individual and the at least one abnormal movement associated with the at least one individual are indicative of an epilepsy diagnosis; and presenting a set of epilepsy medications and a set of physicians that specialize in treating epilepsy at least partially based on the determining whether the at least one indication of abnormal gaze of the individual and the at least one abnormal movement associated with the at least one individual are indicative of an epilepsy diagnosis.

16. A system, comprising:
a device that includes at least one brain activity surrogate marker sensor, the device including at least one or more non-transitory signal-bearing media including at least:
one or more instructions for detecting a gaze of at least one individual;
one or more instructions for accepting brain activity surrogate marker sensor data associated with the individual from the at least one brain activity surrogate marker sensor including at least one indication of abnormal gaze based at least partially on the circuitry for detecting the gaze of the individual;
one or more instructions for detecting at least one abnormal movement associated with the at least one individual;
one or more instructions for determining whether the at least one indication of abnormal gaze of the individual and the at least one abnormal movement associated with the at least one individual are indicative of an epilepsy diagnosis; and
one or more instructions for presenting a set of epilepsy medications and a set of physicians that specialize in treating epilepsy at least partially based on the determining whether the at least one indication of abnormal gaze of the individual and the at least one abnormal movement associated with the at least one individual are indicative of an epilepsy diagnosis.

17. The system of claim 16, wherein the one or more non-transitory signal-bearing media include a computer-readable medium, a recordable medium, or a communications medium.

18. A system, comprising:
a device that includes at least one brain activity surrogate marker sensor; and instructions that when executed on the device cause the device to:
detect a gaze of at least one individual;
accept brain activity surrogate marker sensor data associated with the individual from the at least one brain activity surrogate marker sensor including at least one indication of abnormal gaze based at least partially on the circuitry for detecting the gaze of the individual;
detect at least one abnormal movement associated with the at least one individual;
determine whether the at least one indication of abnormal gaze of the individual and the at least one abnormal movement associated with the at least one individual are indicative of an epilepsy diagnosis; and
present a set of epilepsy medications and a set of physicians that specialize in treating epilepsy at least partially based on the determining whether the at least one indication of abnormal gaze of the individual and the at least one abnormal movement associated with the at least one individual are indicative of an epilepsy diagnosis.

19. The system of claim 2, wherein the circuitry for presenting a set of epilepsy medications and a set of physicians that specialize in treating epilepsy at least partially based on the determining whether the at least one indication of abnormal gaze of the individual and the at least one abnormal movement associated with the at least one individual are indicative of an epilepsy diagnosis comprises:
circuitry for determining at least one proposed treatment associated with the individual based at least partially on at least one indication that the abnormal gaze of the individual is associated with one or more additional markers of at least one health condition; and
circuitry for detecting at least one health care option associated with the at least one proposed treatment.

20. The system of claim 4, wherein the circuitry for detecting at least one mental diagnosis associated with at least one individual comprises:
circuitry for detecting at least one of an indication of anxiety, depression, fear, inattention, a mood disturbance, a phobia, or a psychological test result associated with the individual.

21. The system of claim 2, wherein the circuitry for presenting a set of epilepsy medications and a set of physicians that specialize in treating epilepsy at least partially based on the determining whether the at least one indication of abnormal gaze of the individual and the at least one abnormal movement associated with the at least one individual are indicative of an epilepsy diagnosis comprises:
circuitry for presenting a sequence of a plurality of diagnostic options.

22. The system of claim 2, wherein the brain activity surrogate marker sensor data is used in conjunction with brain activity measurements to present the set of health care options.

23. The system of claim 2, wherein the brain activity surrogate marker sensor data includes at least one of: a skin response to a stimulus; a face pattern indicative of at least one of approval, disapproval, or emotional state; eye movements or pupil movements indicating visual attention to an object; or voice stress patterns indicative of a mental state.

24. The system of claim 2, wherein the brain activity surrogate marker sensor data includes an indicator of attention, approval, disapproval, recognition, cognition, memory, or trust in response to a stimulus, other than measurement of brain activity associated with the stimulus.

25. The system of claim 2, further comprising:
circuitry for receiving a bid from a treatment provider to treat the individual.

26. The system of claim 2, wherein the circuitry for detecting the gaze of at least one individual comprises:
circuitry for detecting eye movements of at least one individual.

27. The system of claim 2, wherein the circuitry for detecting the gaze of at least one individual comprises:
at least one camera coupled with at least one user device.

28. The system of claim 2, wherein the circuitry for accepting brain activity surrogate marker sensor data associated with the individual from the at least one brain activity surrogate marker sensor including at least one indication of abnormal gaze based at least partially on the circuitry for detecting the gaze of the individual comprises:
circuitry for detecting eye movements of at least one individual; and
circuitry for detecting at least one indication the eye movements of the at least one individual are abnormal to previously detected eye movements of the at least one individual.

29. The system of claim 2, wherein the circuitry for determining at least one abnormal movement associated with the at least one individual comprises:

circuitry for receiving at least one touch input from at least one user of at least one user device.

\* \* \* \* \*

UNITED STATES PATENT AND TRADEMARK OFFICE
CERTIFICATE OF CORRECTION

| | | |
|---|---|---|
| PATENT NO. | : 9,911,165 B2 | Page 1 of 1 |
| APPLICATION NO. | : 12/657980 | |
| DATED | : March 6, 2018 | |
| INVENTOR(S) | : Shawn P. Firminger et al. | |

It is certified that error appears in the above-identified patent and that said Letters Patent is hereby corrected as shown below:

Column 48, Line 58, Claim 1:
"partially on the circuitry for detecting the gaze of the . . ." change to --partially on the means for detecting the gaze of the--

Column 50, Line 63, Claim 15:
"on the circuitry for detecting the gaze of the individual;" change to --on the detecting the gaze of the individual;--

Signed and Sealed this
Nineteenth Day of June, 2018

Andrei Iancu
*Director of the United States Patent and Trademark Office*